(12) United States Patent
Sugunan et al.

(10) Patent No.: US 10,945,503 B2
(45) Date of Patent: Mar. 16, 2021

(54) SYSTEMS, DEVICES AND METHODS FOR STYLING HAIR

(71) Applicant: Mirakel Technologies, Inc., Cambridge, MA (US)

(72) Inventors: Suman Lal Chirammal Sugunan, New York, NY (US); Pradeep Paul Panengad, Singapore (SG)

(73) Assignee: MIRAKEL TECHNOLOGIES, INC., Cambridge, MA (US)

( * ) Notice: Subject to any disclaimer, the term of this patent is extended or adjusted under 35 U.S.C. 154(b) by 803 days.

(21) Appl. No.: 15/228,262

(22) Filed: Aug. 4, 2016

(65) Prior Publication Data

US 2017/0071312 A1    Mar. 16, 2017

Related U.S. Application Data

(63) Continuation of application No. PCT/US2015/015825, filed on Feb. 13, 2015.
(Continued)

(51) Int. Cl.
| | |
|---|---|
| *A45D 1/06* | (2006.01) |
| *A45D 2/00* | (2006.01) |
| *A45D 6/00* | (2006.01) |
| *A45D 7/04* | (2006.01) |
| *A61Q 5/06* | (2006.01) |

(Continued)

(52) U.S. Cl.
CPC .............. *A45D 7/04* (2013.01); *A45D 1/06* (2013.01); *A45D 1/14* (2013.01); *A45D 2/001* (2013.01); *A45D 6/00* (2013.01); *A45D 7/00* (2013.01); *A45D 19/00* (2013.01); *A61K 8/19* (2013.01); *A61K 8/731* (2013.01); *A61K 8/88* (2013.01); *A61Q 5/06* (2013.01); *A45D 2019/0091* (2013.01); *A61K 2800/43* (2013.01); *A61K 2800/83* (2013.01)

(58) Field of Classification Search
CPC ......... A45D 7/04; A61K 2800/83; A61Q 5/06
See application file for complete search history.

(56) References Cited

U.S. PATENT DOCUMENTS

| | | | | |
|---|---|---|---|---|
| 2,028,051 A | * | 1/1936 | Durham | ................... A45D 4/06 132/206 |
| 5,743,278 A | * | 4/1998 | Ookura et al. | ......... A45D 2/001 |

(Continued)

*Primary Examiner* — Salil Jain
(74) *Attorney, Agent, or Firm* — Morgan, Lewis & Bockius LLP

(57) ABSTRACT

Devices and methods for styling hair, and in particular, to devices and methods for styling hair using electrolysis are described herein. A method for styling hair includes arranging a section of hair between a first electrode and a second electrode. The section of hair is contacted with an electrolyte before being arranged between the first and second electrodes, after being arranged between the first and second electrodes, and/or concurrently with being arranged between the first and second electrodes. The method further includes causing the first electrode to have a first negative potential, and causing the second electrode to have a second potential, such that the absolute value of the first negative potential is greater than the absolute value of the second potential, and such that the difference in electrical potential between the first electrode and the second electrode creates an electrolysis zone between the first electrode and the second electrode.

27 Claims, 46 Drawing Sheets

Related U.S. Application Data

(60) Provisional application No. 61/940,086, filed on Feb. 14, 2014, provisional application No. 61/989,987, filed on May 7, 2014.

(51) Int. Cl.
*A45D 19/00* (2006.01)
*A45D 7/00* (2006.01)
*A45D 1/14* (2006.01)
*A61K 8/19* (2006.01)
*A61K 8/73* (2006.01)
*A61K 8/88* (2006.01)

(56) References Cited

U.S. PATENT DOCUMENTS

| | | | | |
|---|---|---|---|---|
| 8,596,285 | B1* | 12/2013 | Ramaprasad | A45D 7/06 |
| 2010/0215608 | A1* | 8/2010 | Dorr | A61Q 5/06 |
| | | | | 424/70.15 |
| 2013/0089769 | A1* | 4/2013 | Proctor | H01G 11/28 |
| | | | | 429/127 |
| 2013/0306100 | A1* | 11/2013 | Wandke et al. | D06M 10/02 |

* cited by examiner

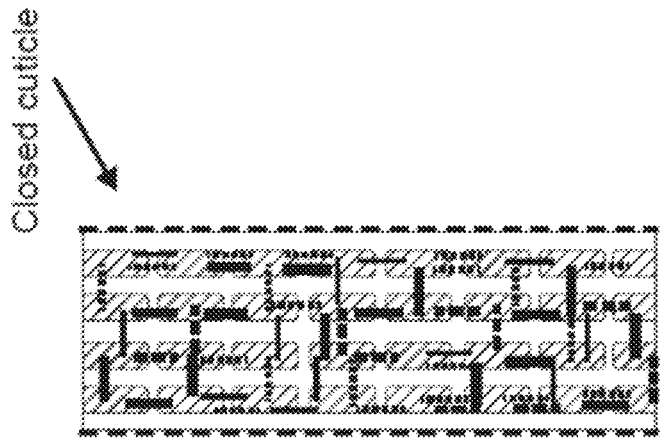
FIG. 6C Closed cuticle
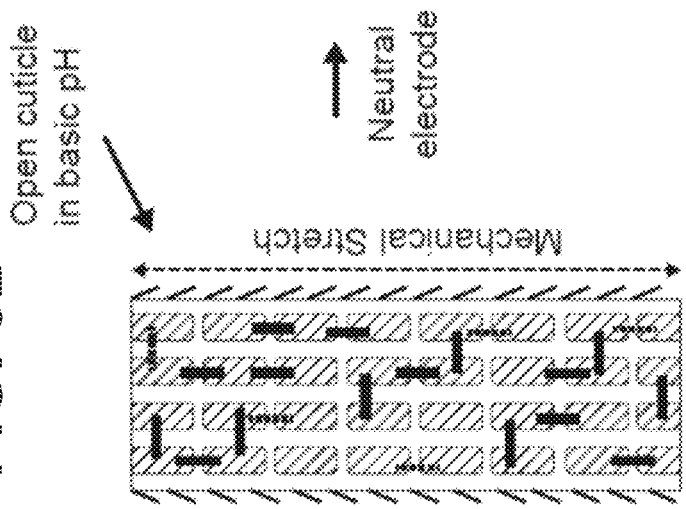
FIG. 6B Open cuticle in basic pH
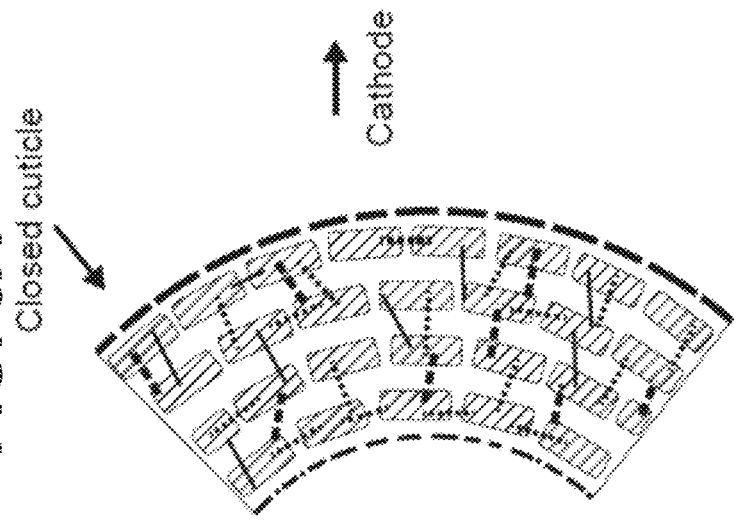
FIG. 6A Closed cuticle

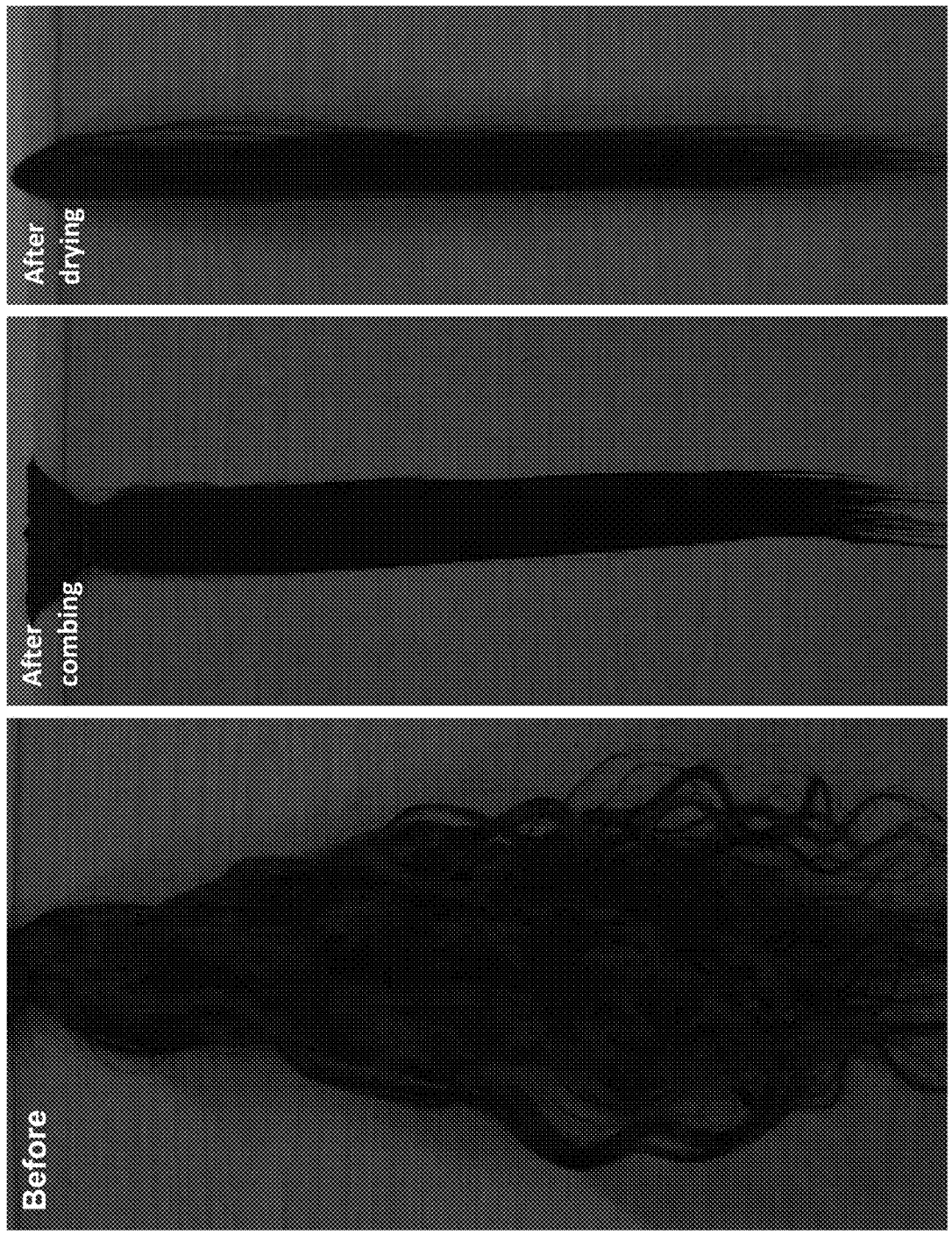

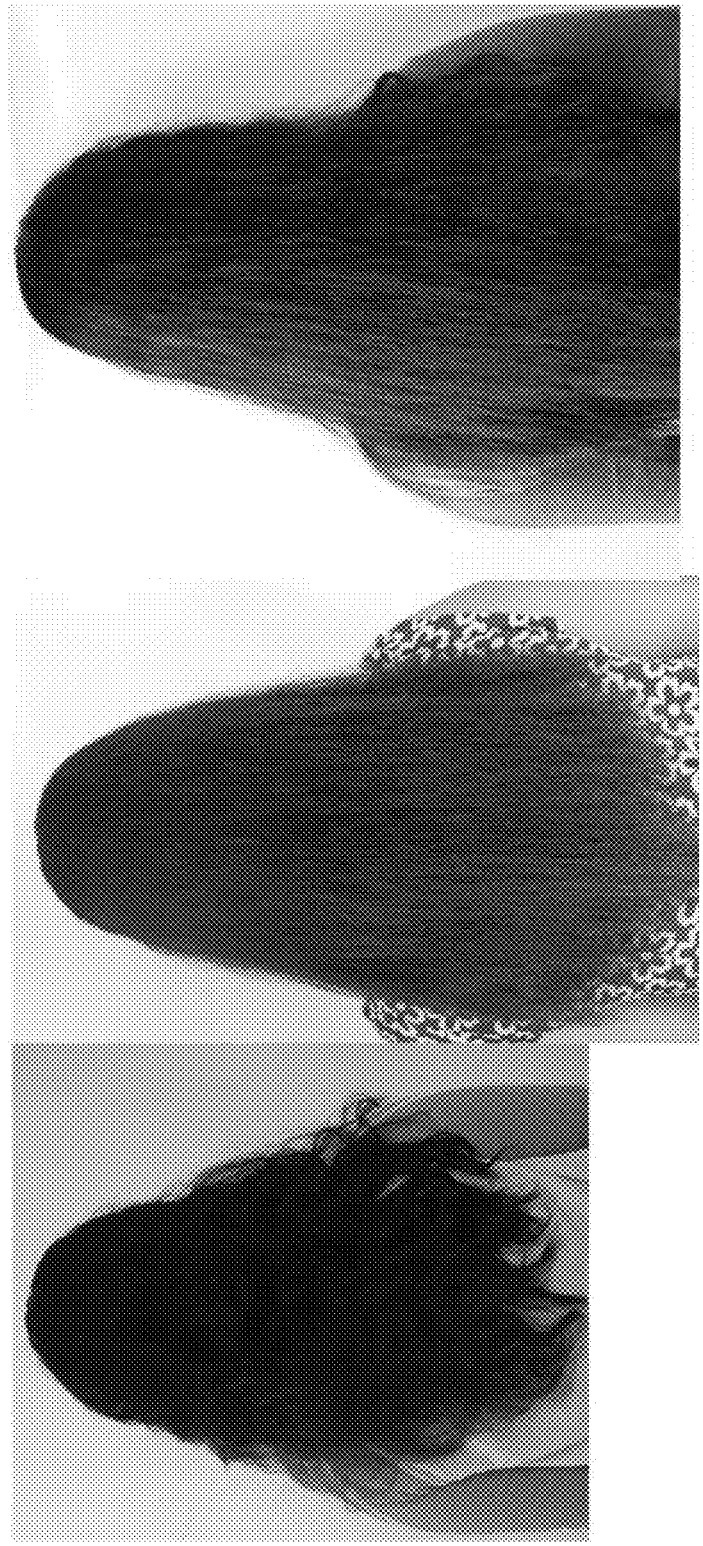

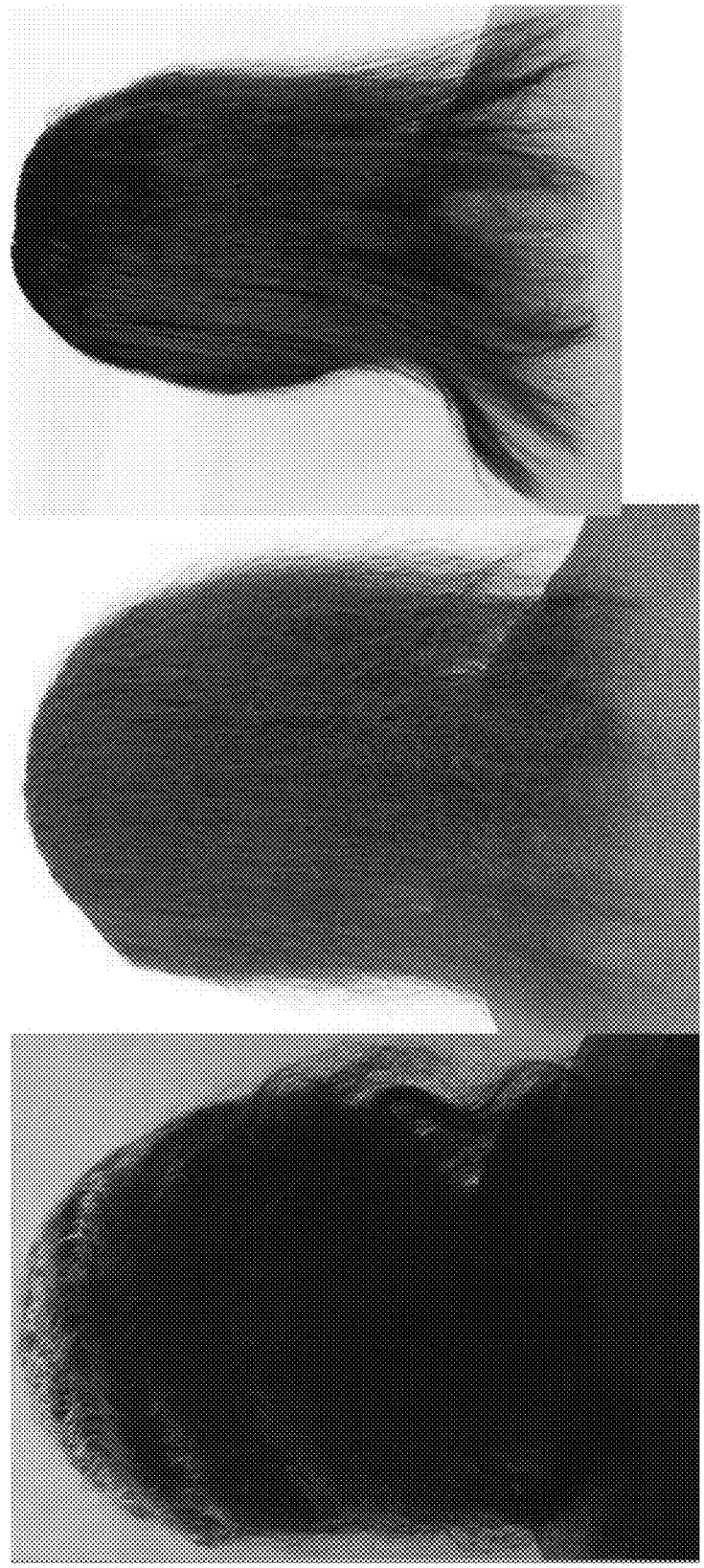

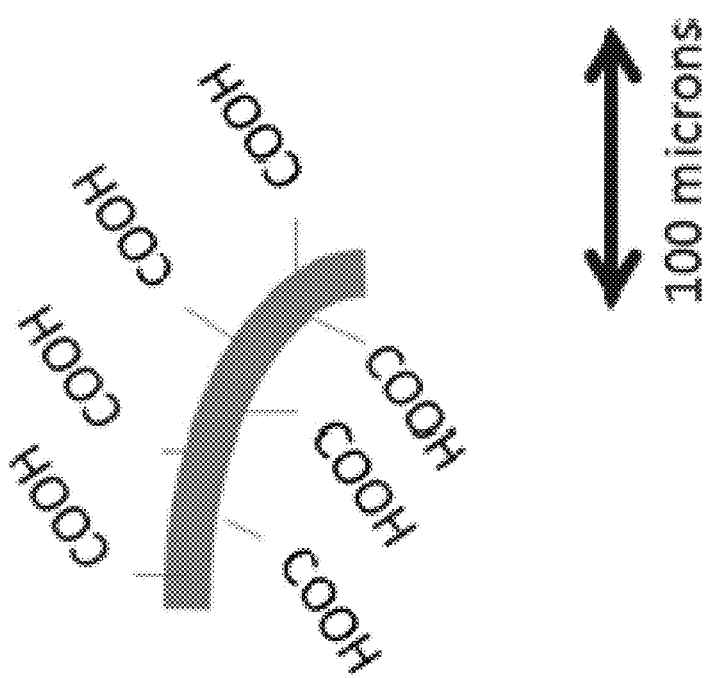

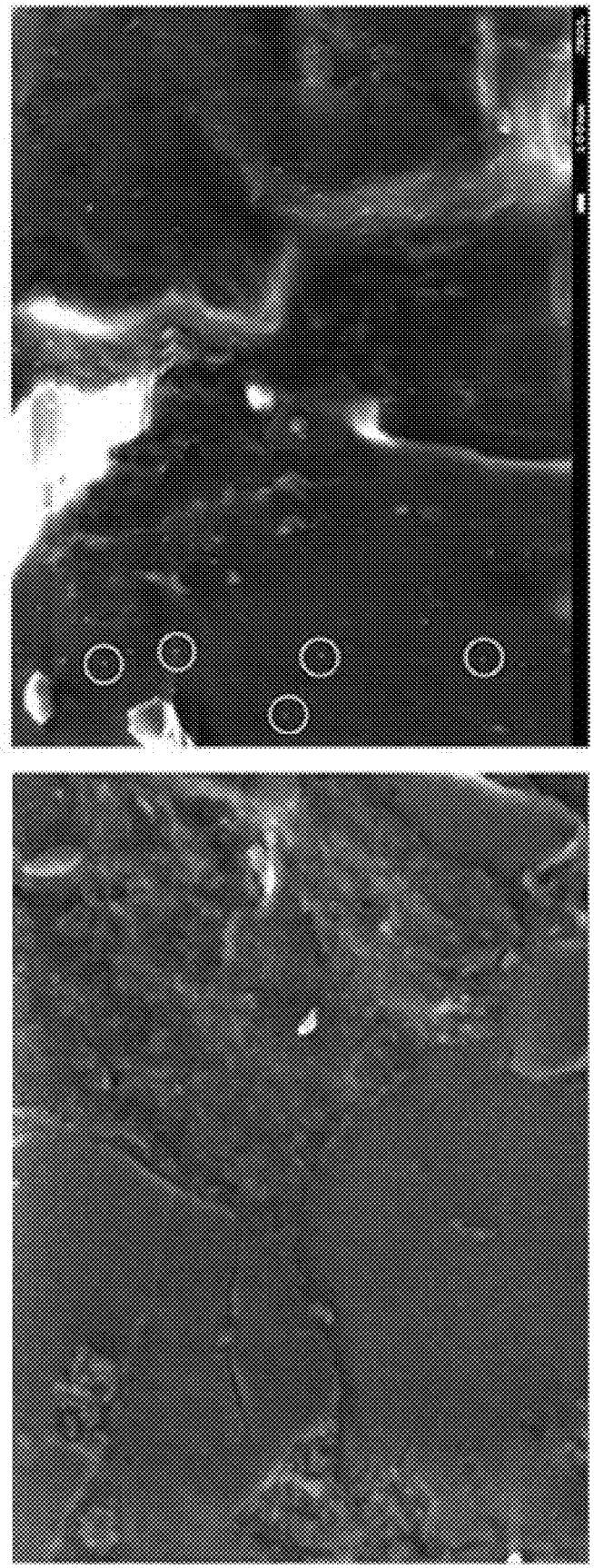

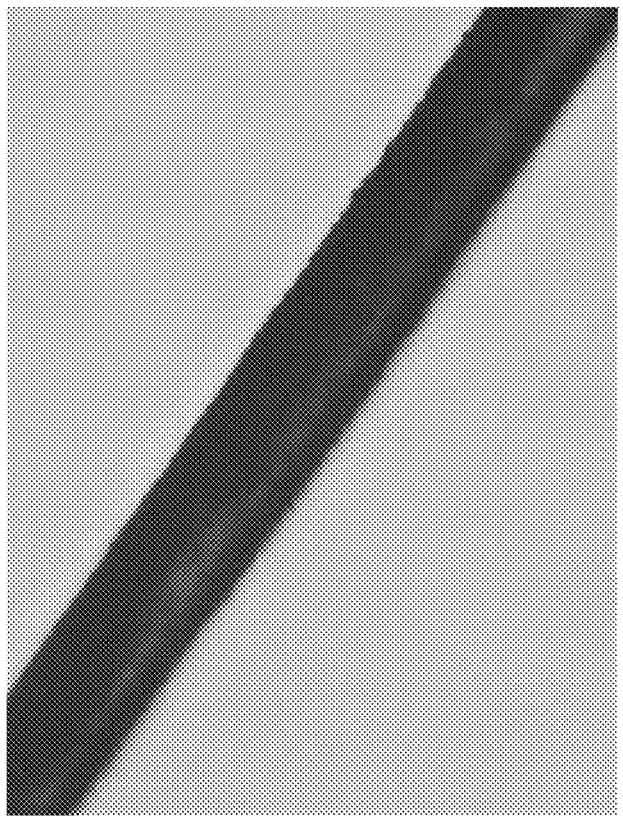
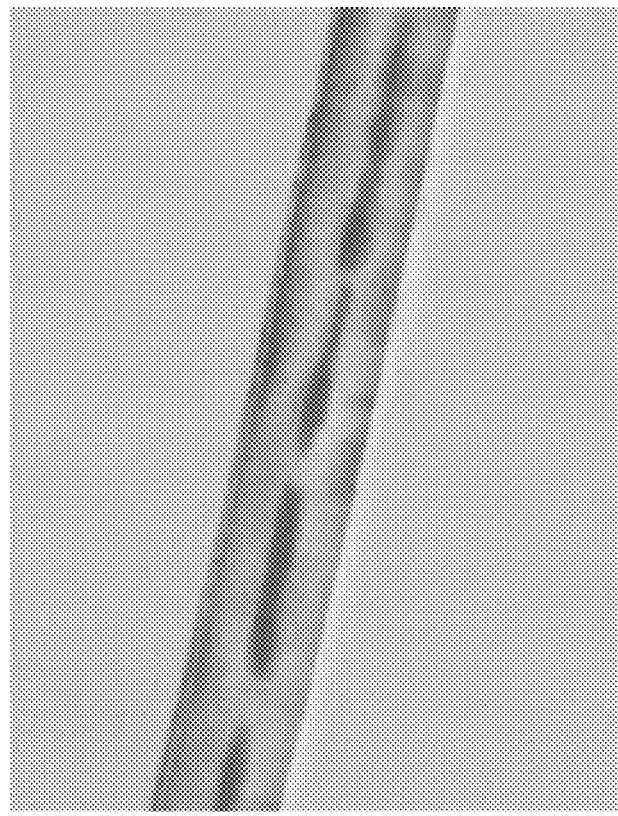

SYSTEMS, DEVICES AND METHODS FOR STYLING HAIR

CROSS REFERENCE TO RELATED APPLICATIONS

This application is a continuation of International Patent Application No. PCT/US2015/15825, filed Feb. 13, 2015, entitled "Systems, Devices And Methods For Styling Hair," which claims priority to and benefit of U.S. Provisional Patent Application No. 61/940,086, filed Feb. 14, 2014, entitled "Systems, Devices and Methods for Styling Hair," and of U.S. Provisional Patent Application No. 61/989,987, filed May 7, 2014, entitled "Electrolyte Formulations for Styling Hair Using Electrolysis," the disclosures of which are hereby incorporated by reference in their entirety.

BACKGROUND

Embodiments described herein relate generally to devices and methods for styling hair, and in particular, to devices and methods for styling hair using electrolysis.

Hair is made of a protein keratin which is rich in sulfur containing amino acids. The keratin protein matrix in the hair is held together by millions of disulfide bonds that provide the strength and stability of the hair. The disulfide bonds located on the surface of the hair have the maximum leverage in determining the shape of the hair. The distribution of the disulfide bonds with respect to the axis of the hair can dictate the "straightness" or "curliness" of the hair. The disulfide bonds act as a scaffold and can be repositioned to alter the condition and/or orientation of the hair. Known conventional methods for styling hair, for example, "hair rebonding," "relaxers," and "perming techniques" use heat, chemicals, or both to break the disulfide bonds, shape the hair into the desired form, for example, straight or curly, and subsequently rebond the disulfide bonds, such that the hair retains the reshaped form for some period of time.

SUMMARY

Embodiments described herein relate generally to devices and methods for styling hair, and in particular, to devices and methods for styling hair using electrolysis. In some embodiments, a method for styling hair includes arranging a section of hair between a first electrode and a second electrode. The section of hair is contacted with an electrolyte before being arranged between the first and second electrodes, after being arranged between the first and second electrodes, and/or concurrently with being arranged between the first and second electrodes. The method further includes causing the first electrode to have a first negative potential, and causing the second electrode to have a second potential, such that the absolute value of the first negative potential is greater than the absolute value of the second potential, and such that the difference in electrical potential between the first electrode and the second electrode creates an electrolysis zone between the first electrode and the second electrode.

BRIEF DESCRIPTIONS OF THE DRAWINGS

FIG. 6A shows the distribution of disulfide, ionic, and hydrogen bonds in an untreated portion of hair. FIG. 6B shows the distribution of the bonds in the portion of hair after exposure to an alkaline environment produced by a first electrode biased at a negative voltage. FIG. 6C shows the distribution of the bonds in the portion of hair after exposure to a neutral environment near a second electrode having a negative voltage.

Figure 7:
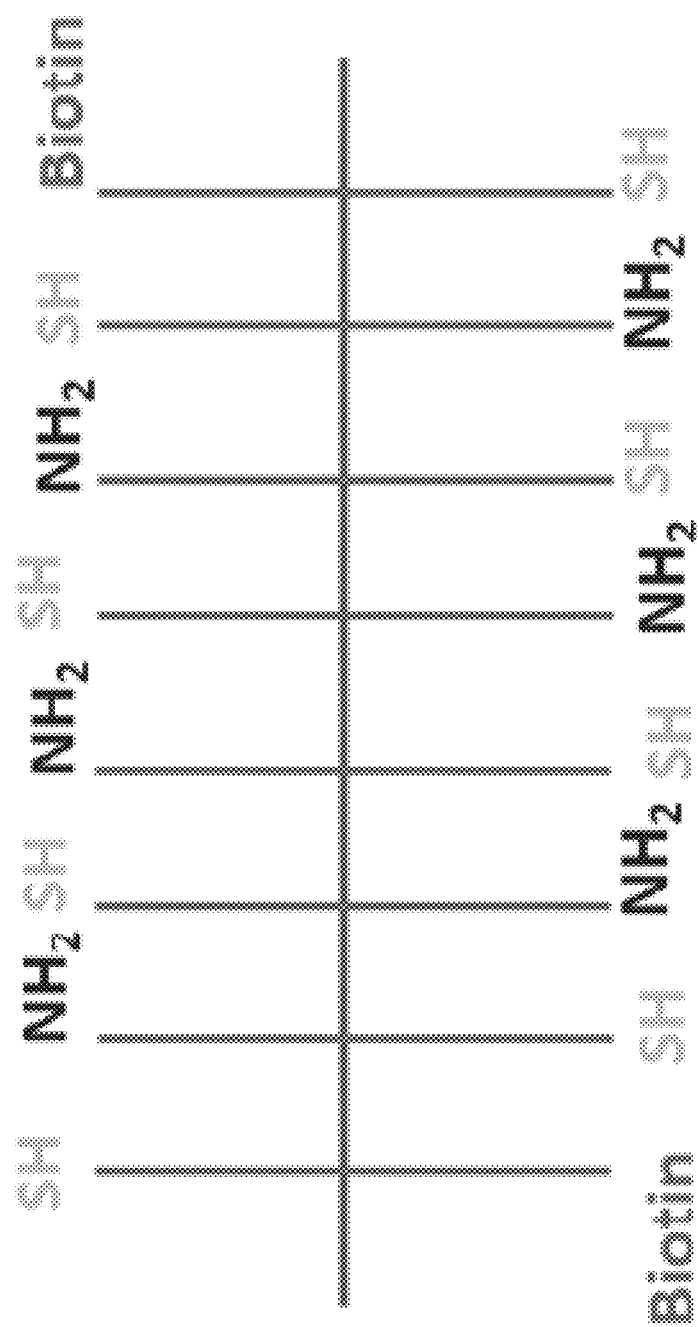

FIG. 7 shows a multifunctional polymer molecule that includes a plurality of sulfhydryl groups, amine groups and biotin tags.

Figure 1:
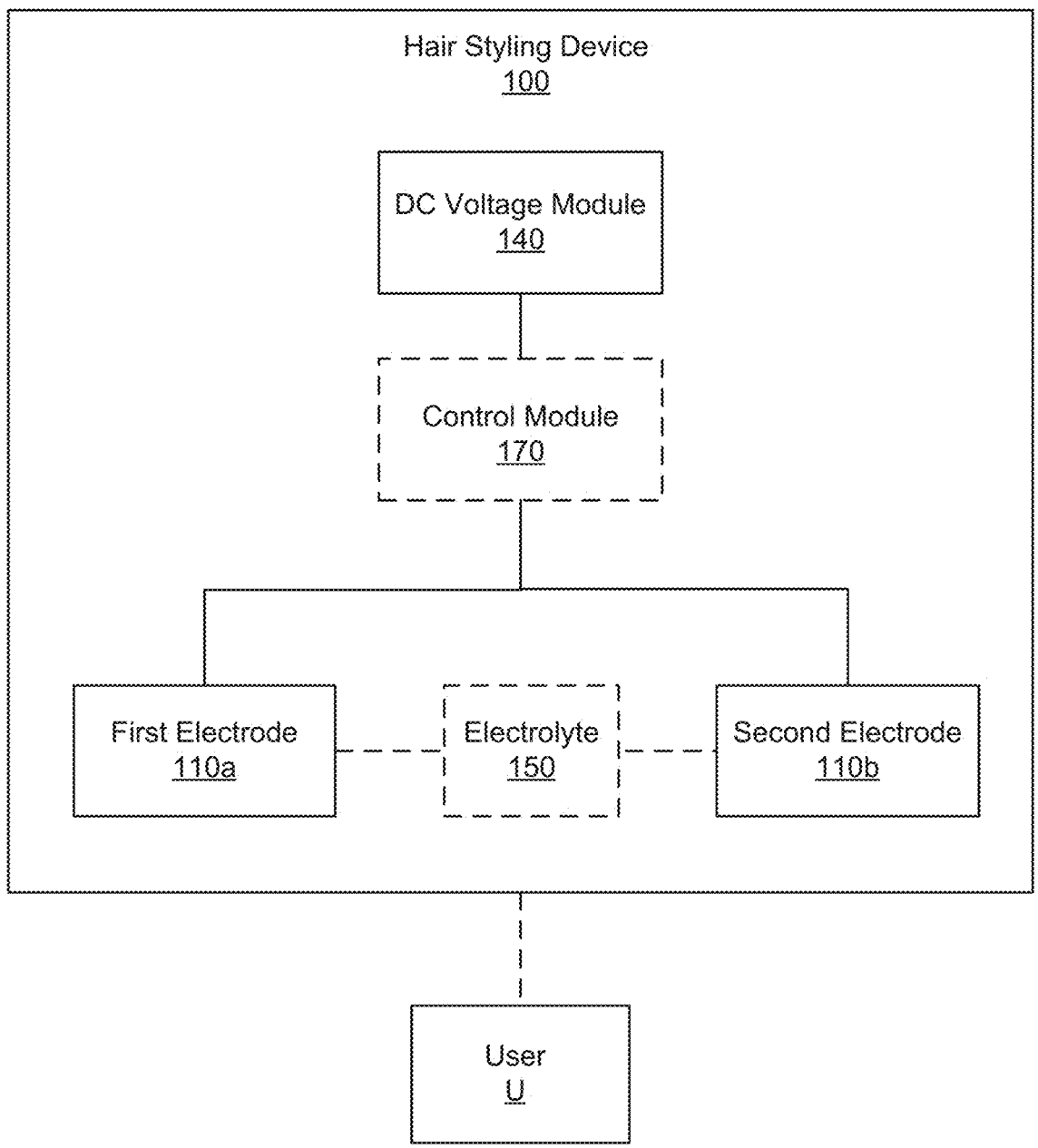
FIG. 1 shows a schematic block diagram of a hair styling device, according to an embodiment.
Figure 8:
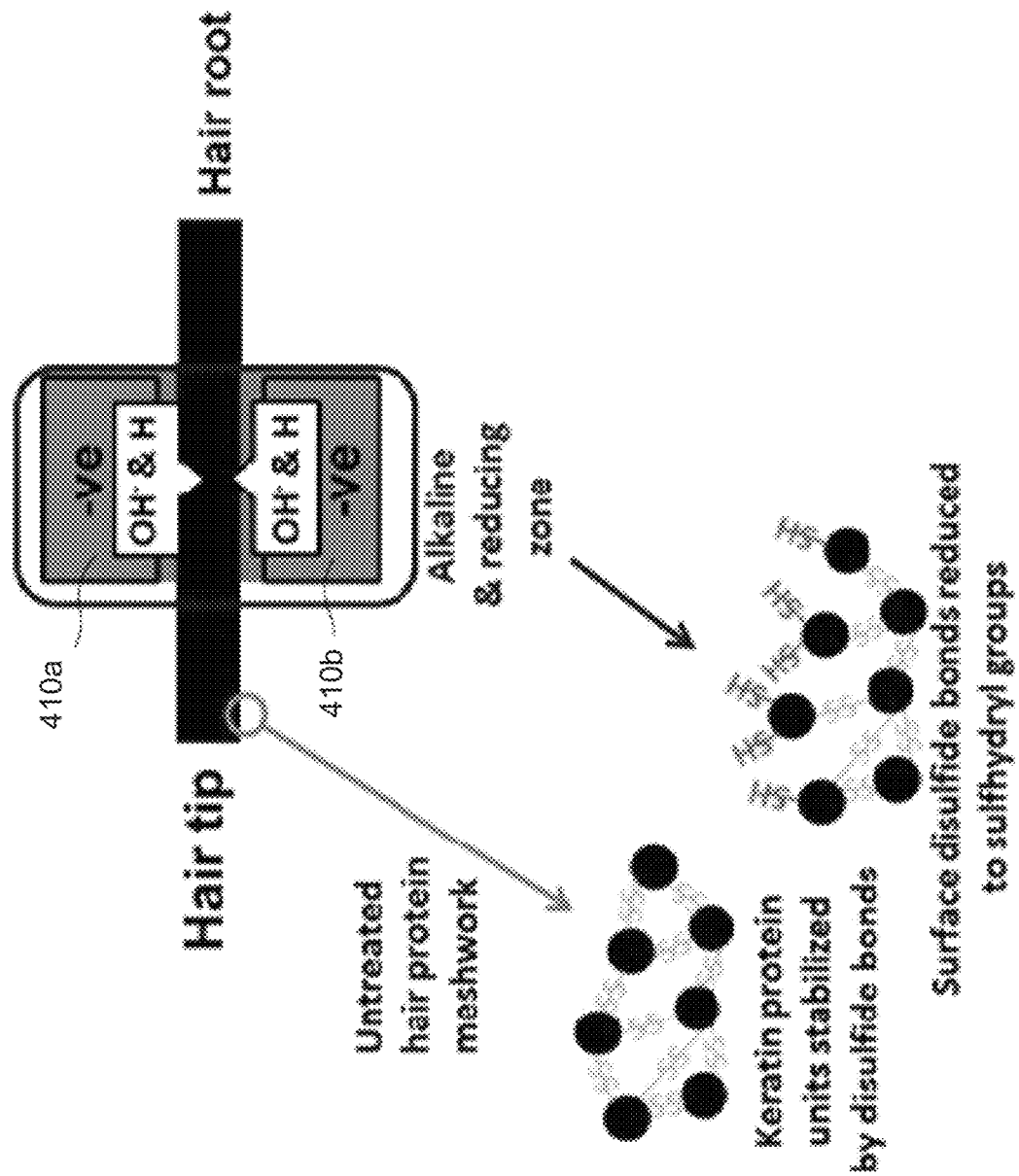

FIG. 8 shows a mechanism of incorporating additives into hair using the hair styling device of FIG. 1 according to an embodiment.

Figure 9:
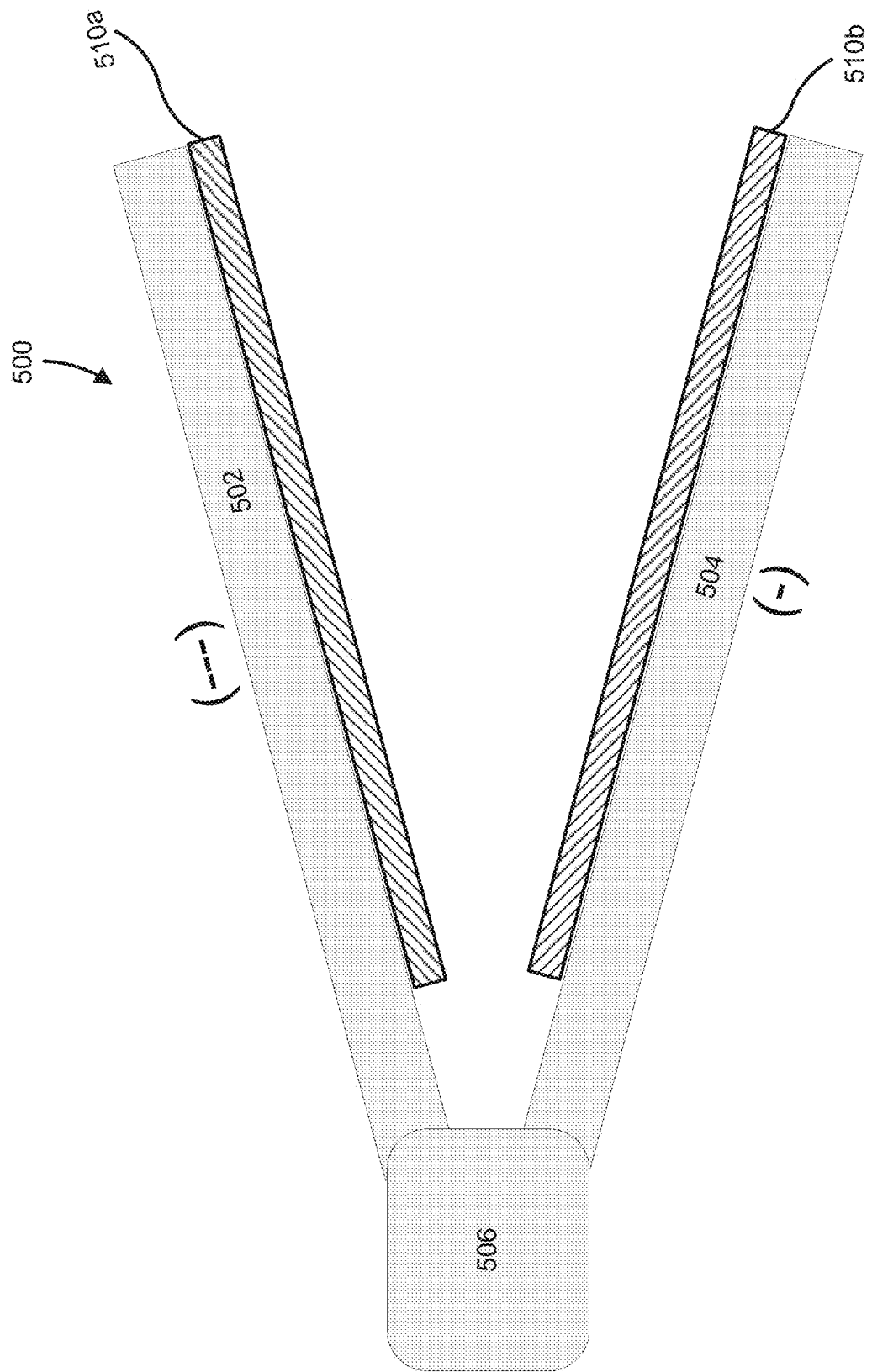

FIG. 9 is a schematic illustration of a side view of a hair styling device, in a first configuration, according to an embodiment.

Figure 10:
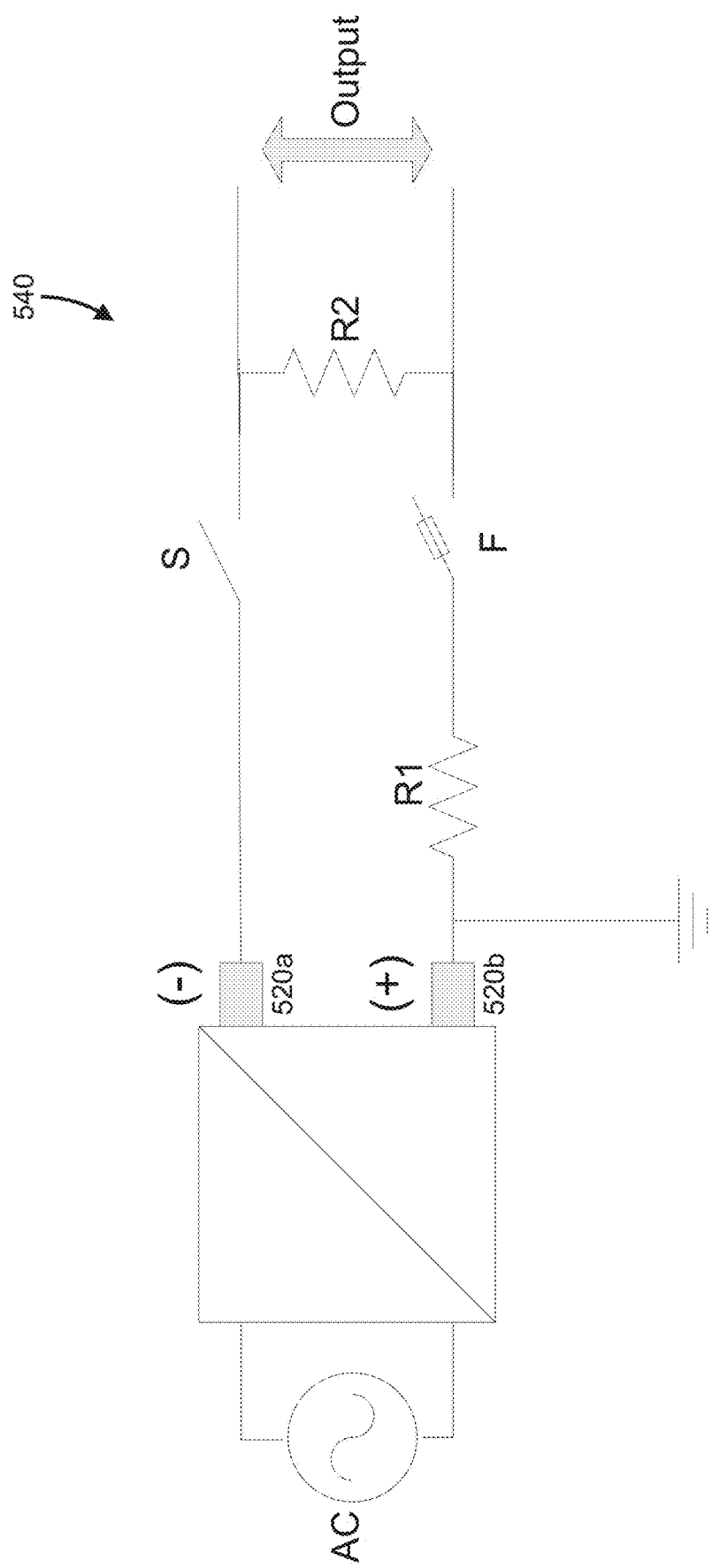

FIG. 10 shows a schematic illustration of a DC voltage module circuit, according to an embodiment.

Figure 11:
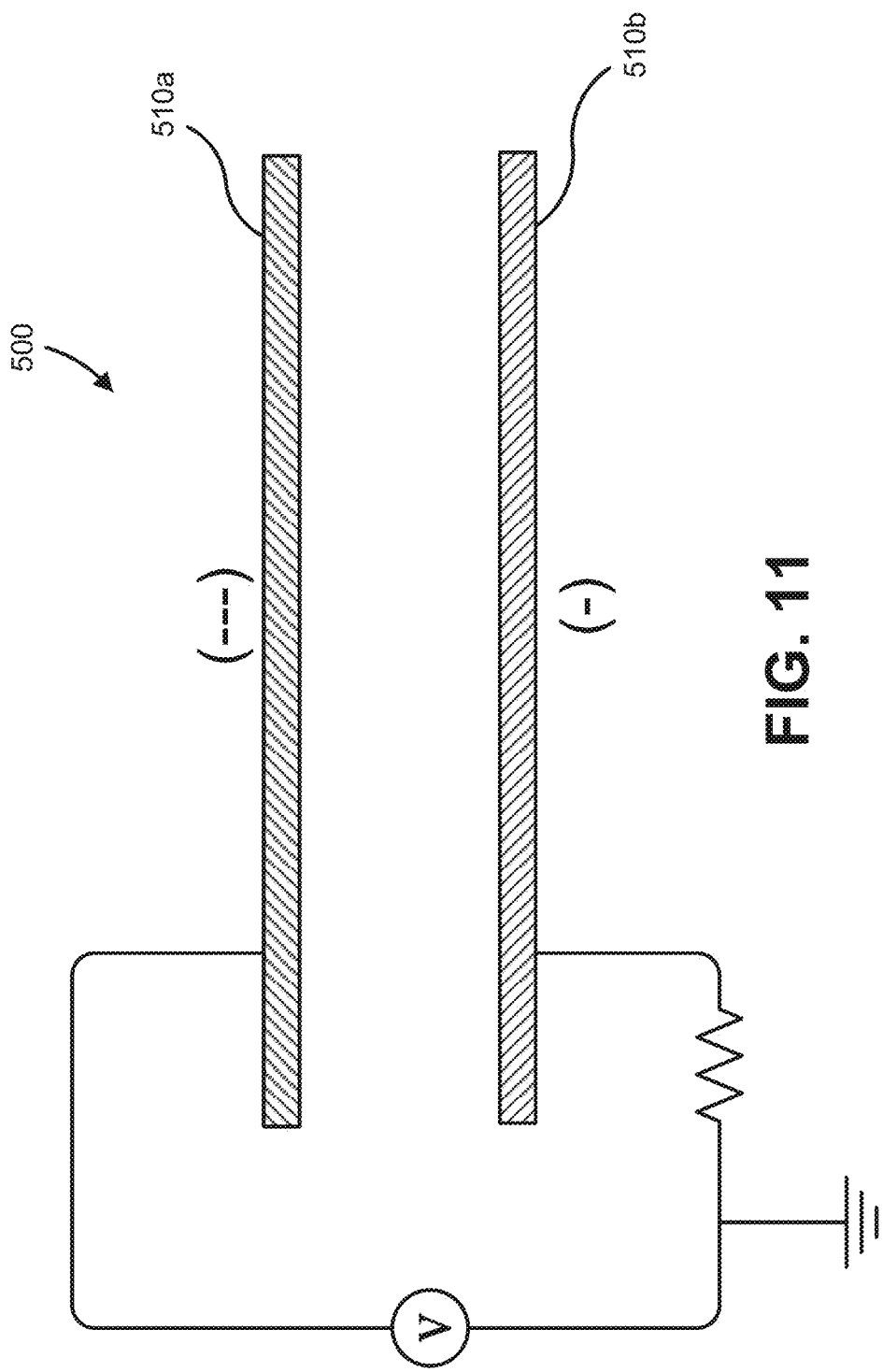

FIG. 11 is a schematic illustration of a side view of a first electrode and a second electrode of a hair styling device, according to an embodiment.

Figure 12:
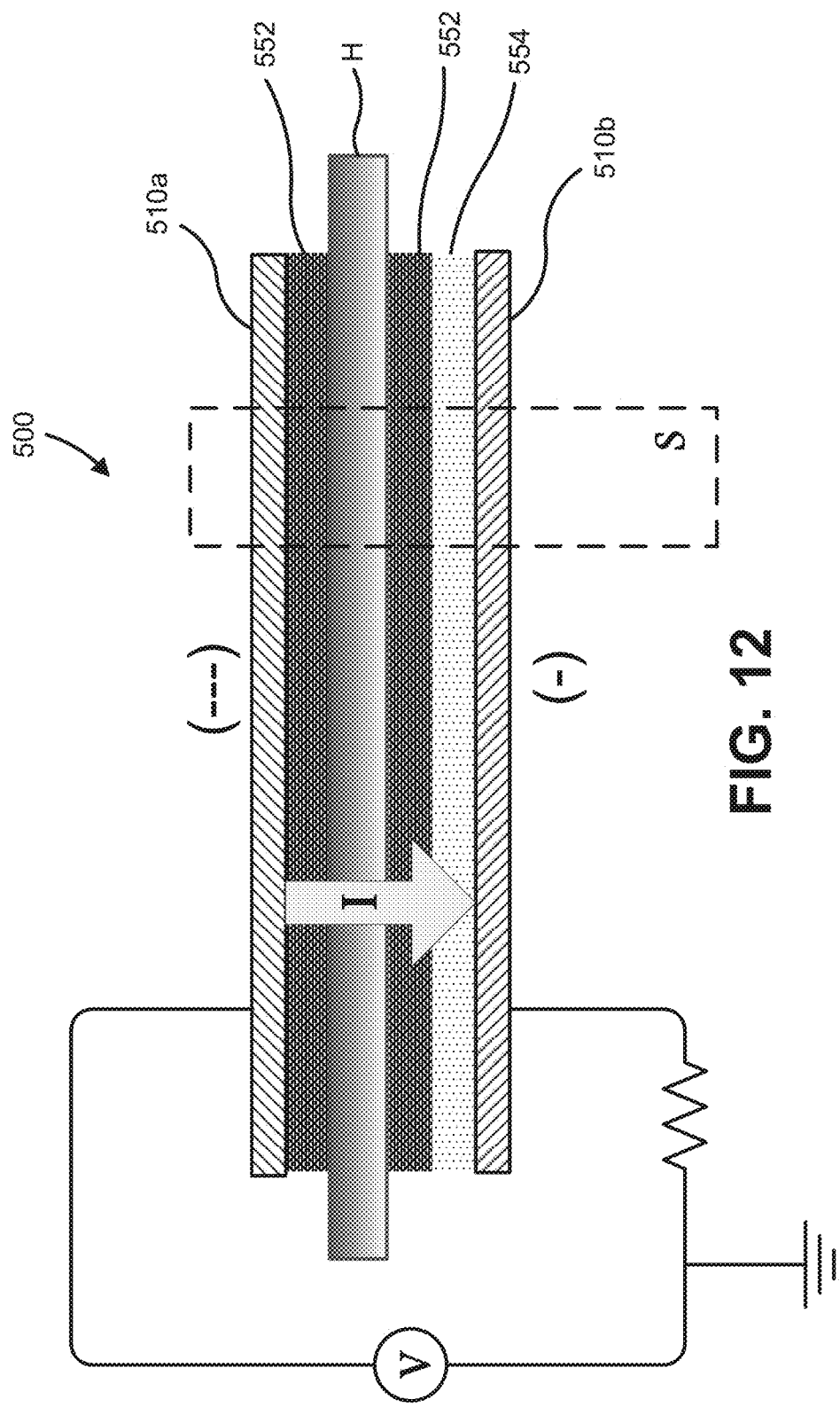

FIG. 12 is a schematic illustration of a side view of the first electrode and the second electrode of the hair styling device of FIG. 11, having an electrolyte and a segment of hair disposed therebetween and a current flowing therebetween, according to an embodiment.

Figure 13:
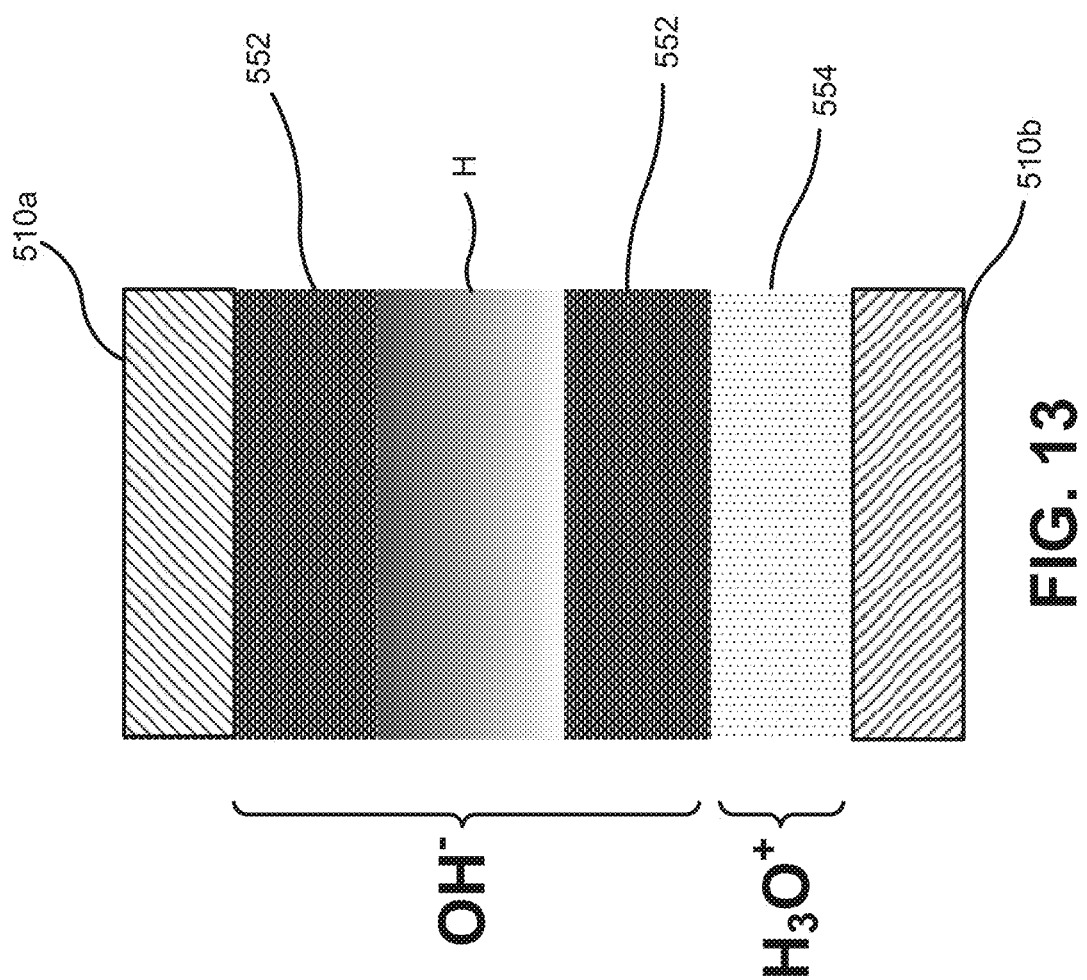

FIG. 13 is a cross-sectional view of the region marked "S" in FIG. 12, showing the locations of the first electrode, the second electrode, the alkaline zone, and the segment of hair.

Figure 14:
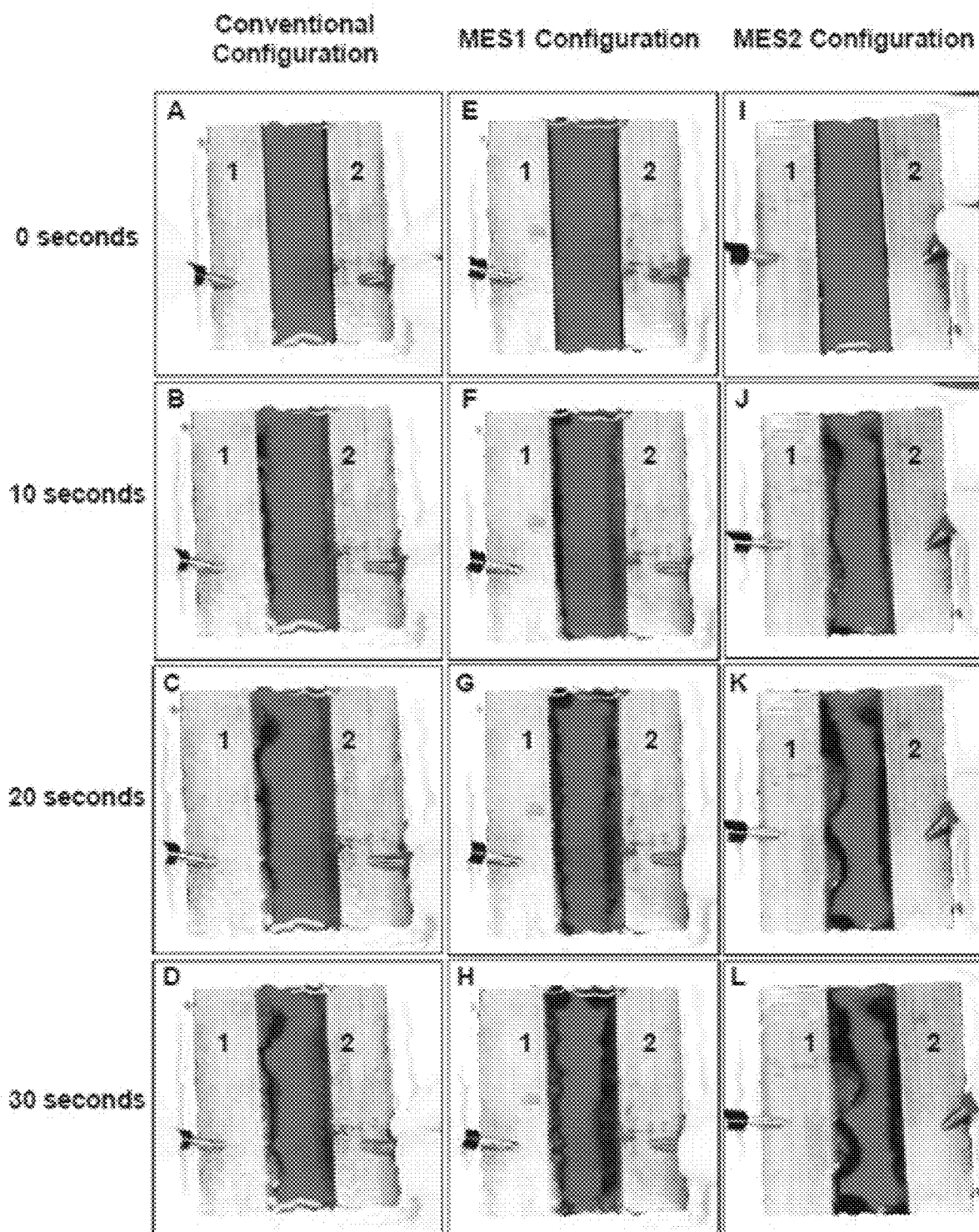

FIG. 14 shows acidic and alkaline zones produced between a first electrode and a second electrode at various voltages and polarities. Panels A-D show the pH at various locations in an electrolysis zone produced between the first electrode biased at a negative voltage and the second electrode having a positive voltage at 0 seconds, 10 seconds, 20 seconds, and 30 seconds after applying the biasing voltages, respectively. Panels E-H show the pH at various locations in an electrolysis zone produced between the first electrode biased at a negative voltage and the second electrode maintained at ground at 0 seconds, 10 seconds, 20 seconds, and 30 seconds, after applying the biasing voltages, respectively. Panels I-L show the pH at various locations in an electrolysis zone produced between the first electrode biased at a first negative voltage and the second electrode having a second negative voltage substantially less than the first negative potential at 0 seconds, 10 seconds, 20 seconds, and 30 seconds after applying the biasing voltages, respectively.

Figure 15:
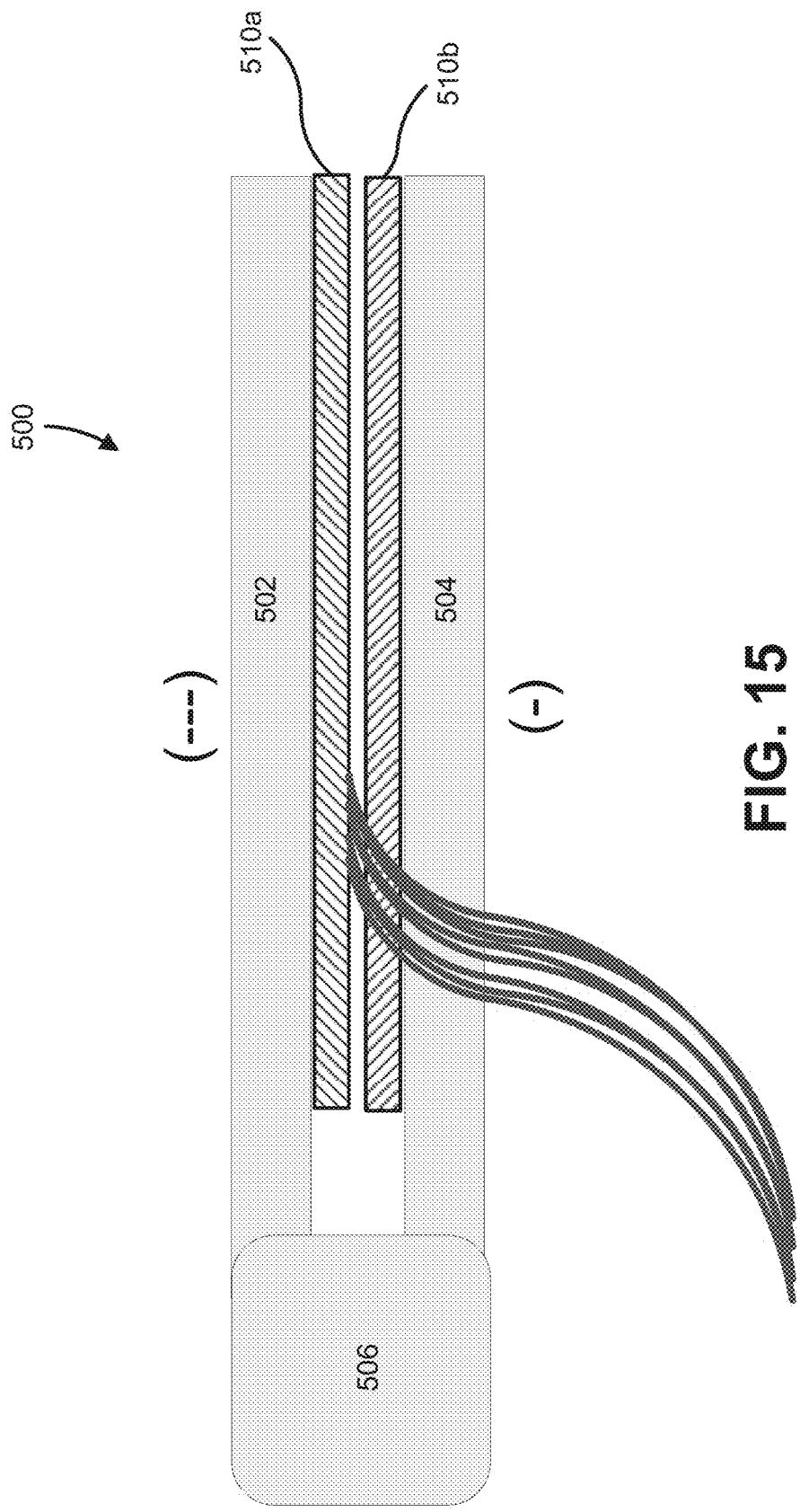

FIG. 15 is a side view of the hair styling device of FIG. 11 in a second configuration, according to an embodiment.

Figure 16:
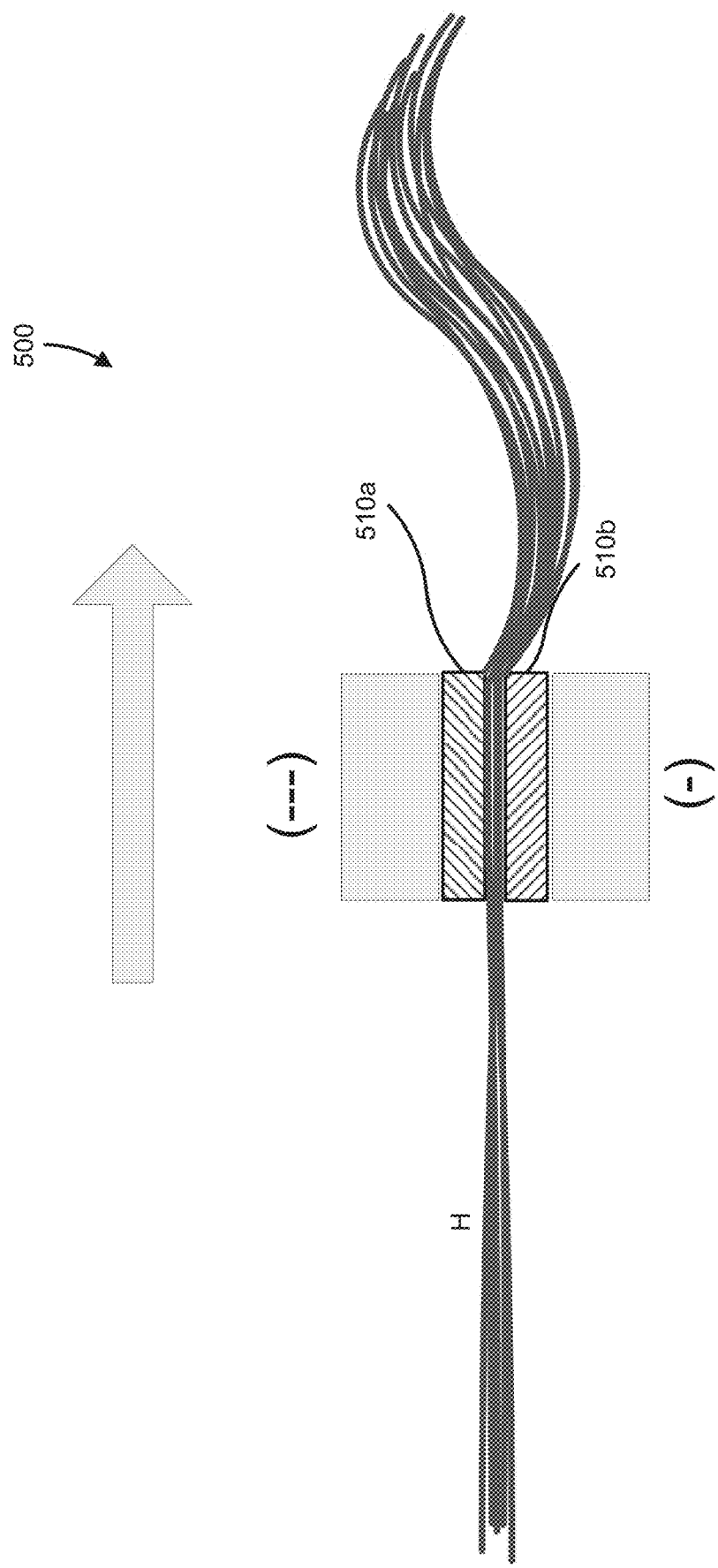

FIG. 16 is an end view of the hair styling device of FIG. 15 in the second configuration, according to an embodiment.

Figure 17:
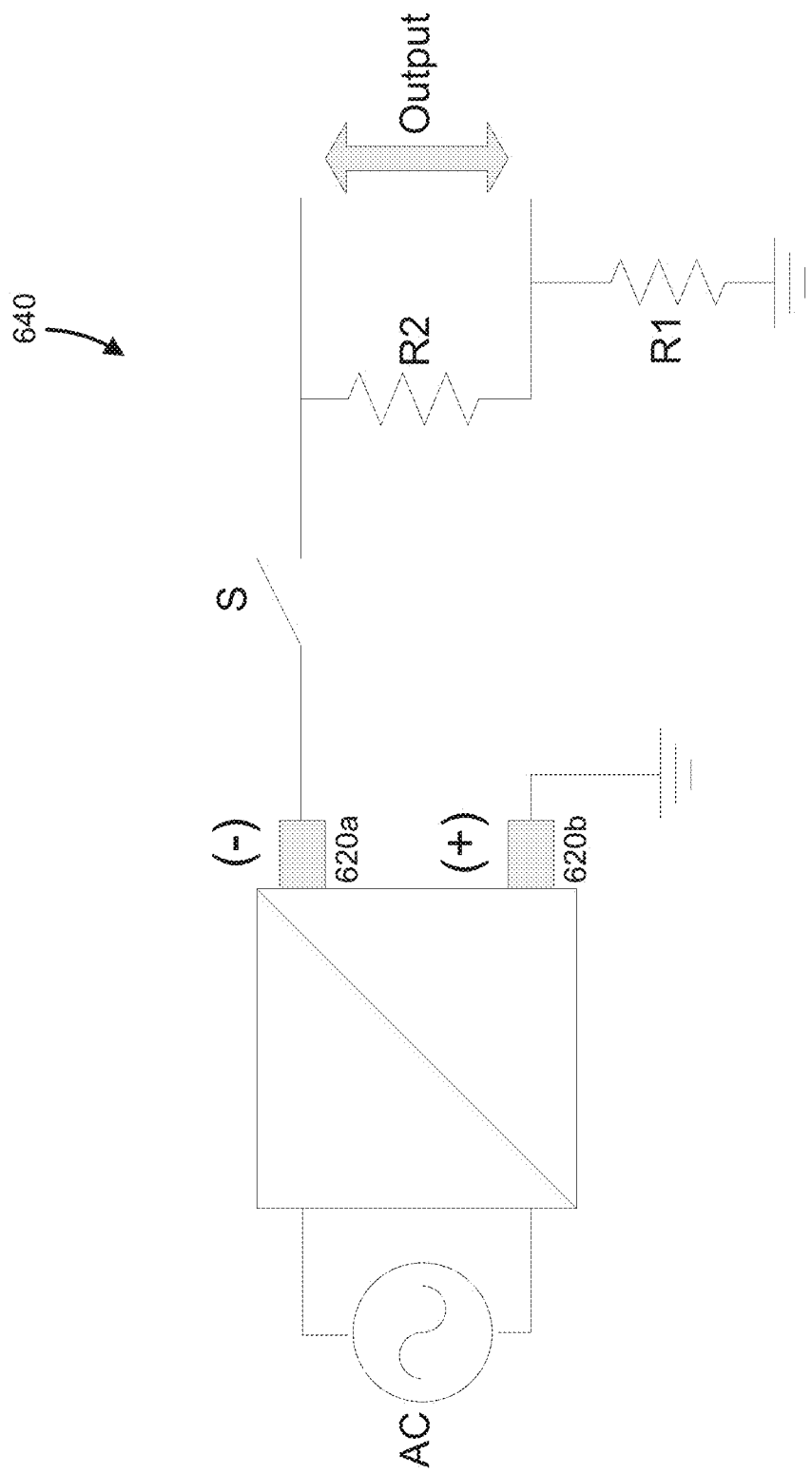

FIG. 17 shows a schematic illustration of a DC voltage module circuit, according to an embodiment.

Figure 18:
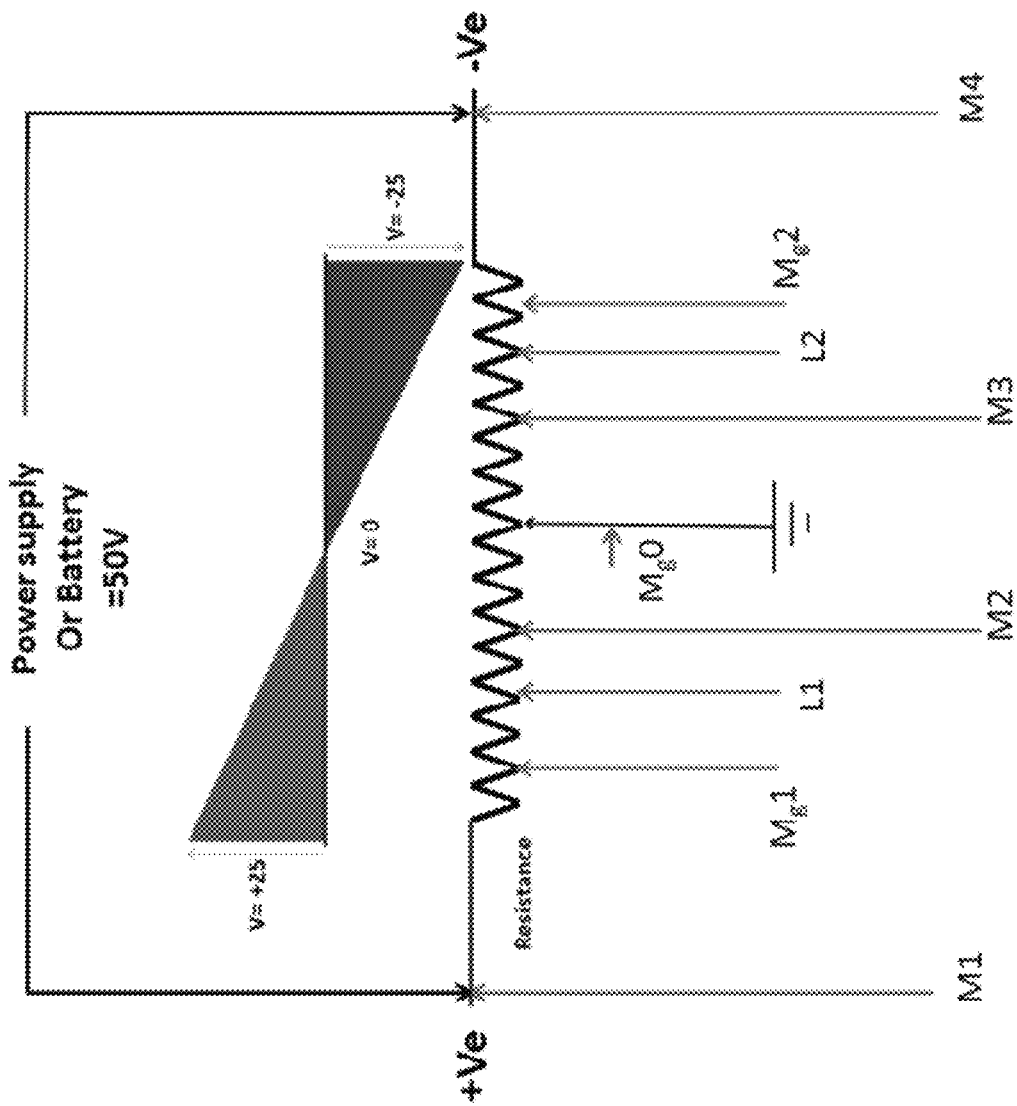

FIG. 18 shows various configurations of biasing voltages and charge that can be implemented by a control module on electrodes included in the hair styling device of FIG. 1.

Figure 19:
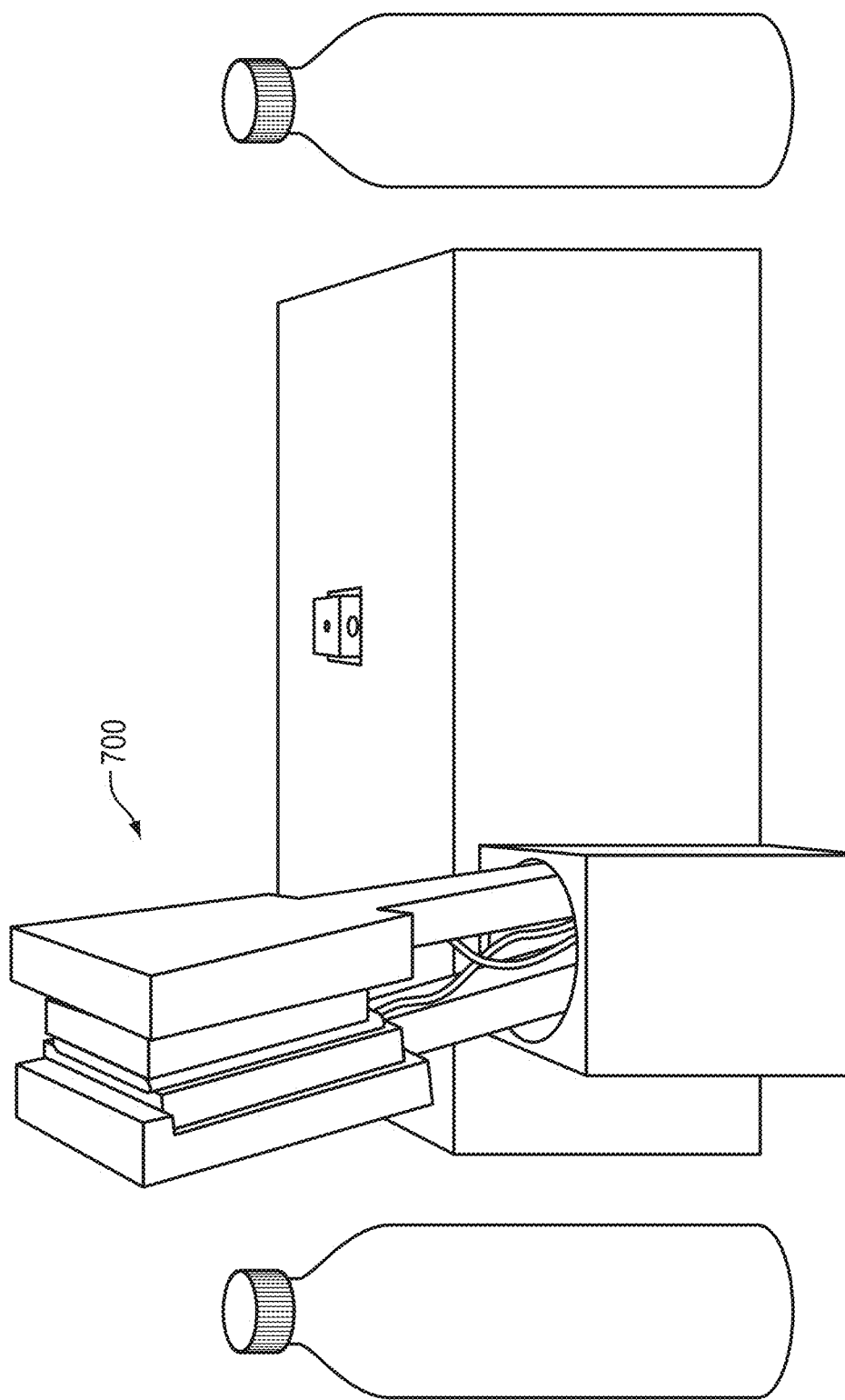

FIG. 19 is a hair styling device kit, according to an embodiment.

Figure 20:
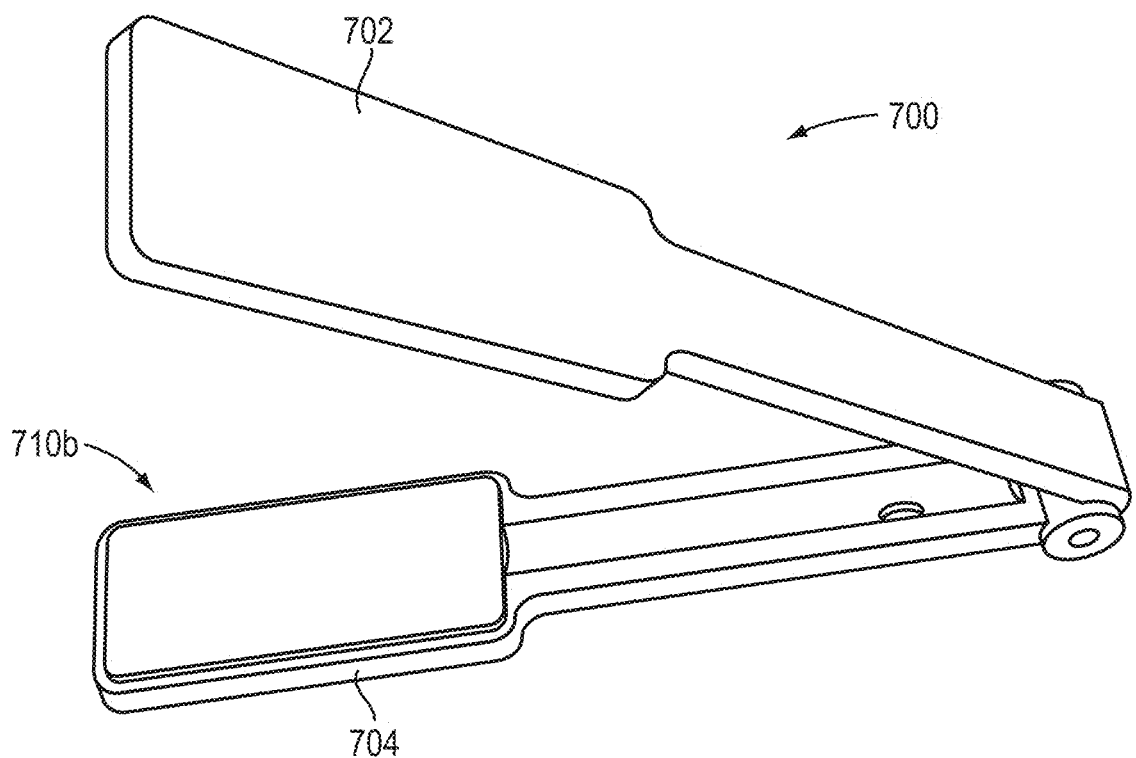

FIG. 20 shows a hair styling device, according to an embodiment.

Figure 21:
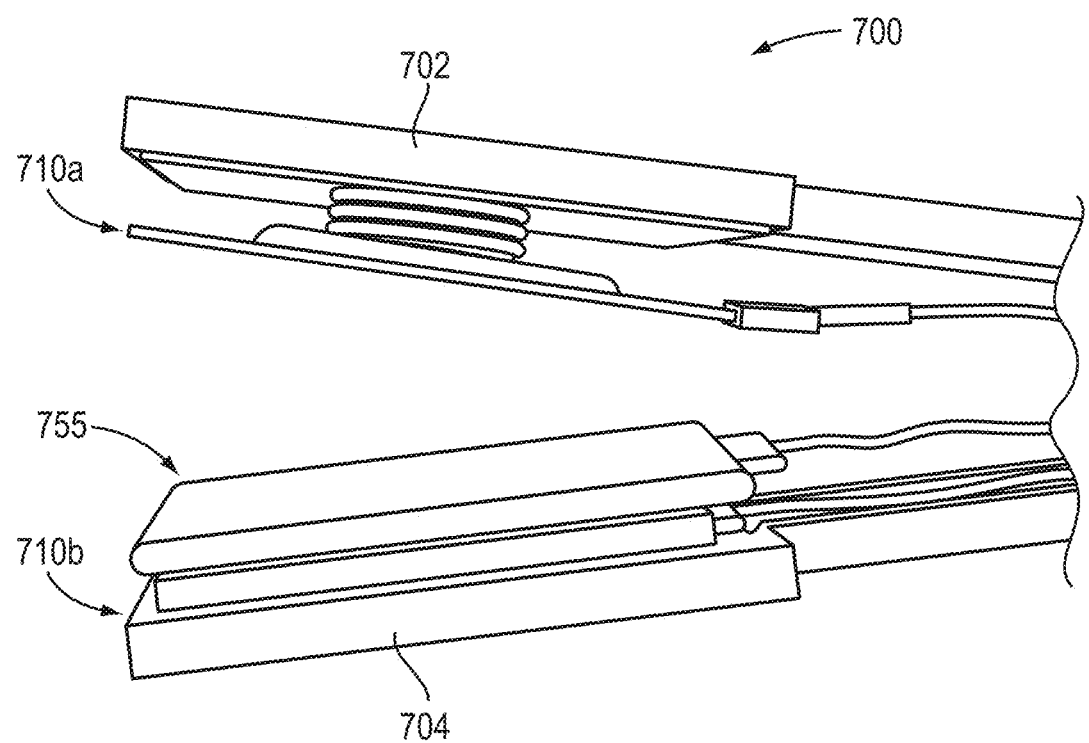

FIG. 21 is a partial view of the hair styling device of FIG. 20, in a first configuration.

Figure 22:
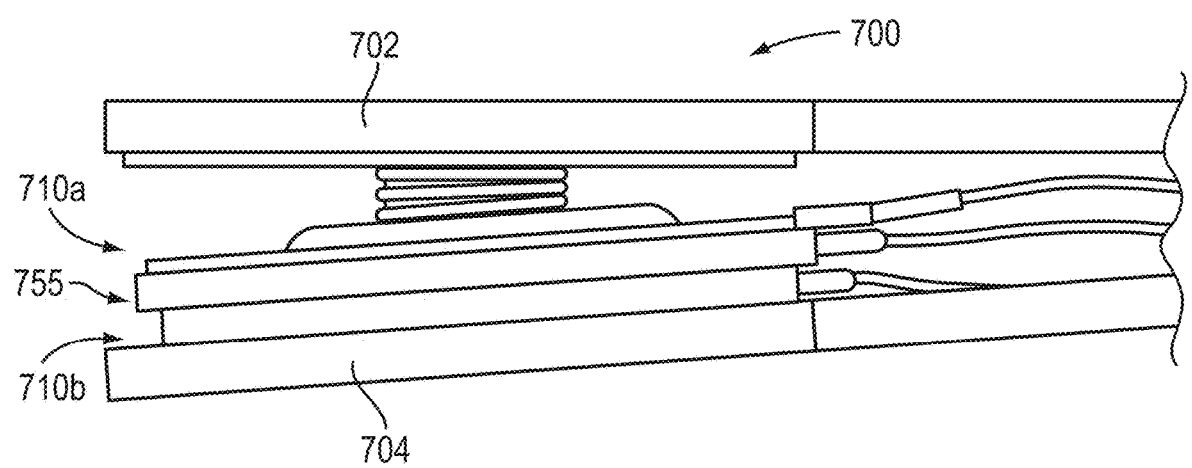

FIG. 22 is a partial view of the hair styling device of FIG. 20, in a second configuration.

Figure 23A:
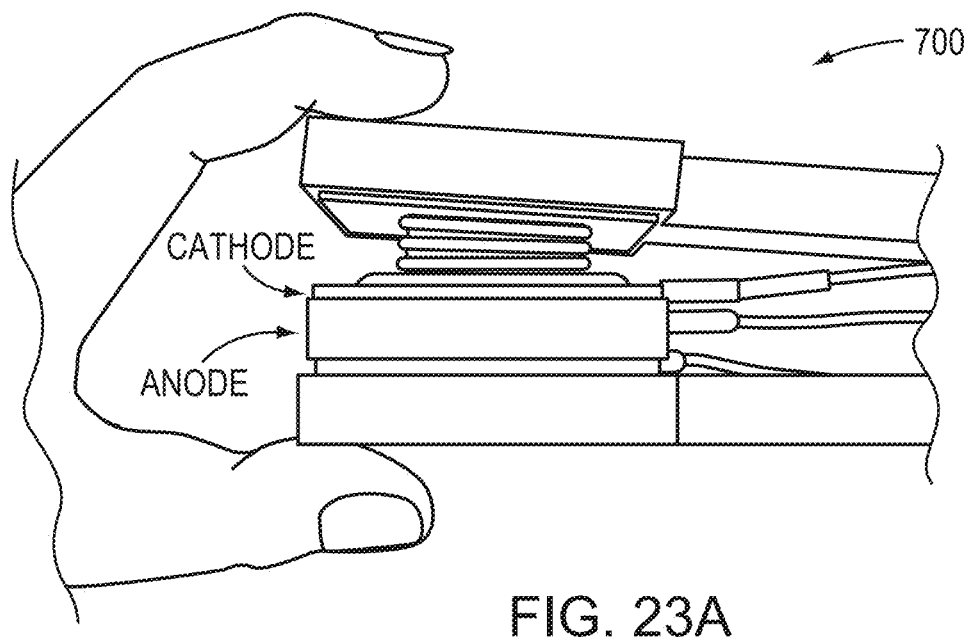

FIG. 23A is a partial view of the hair styling device of FIG. 20, in the second configuration.

Figure 23B:
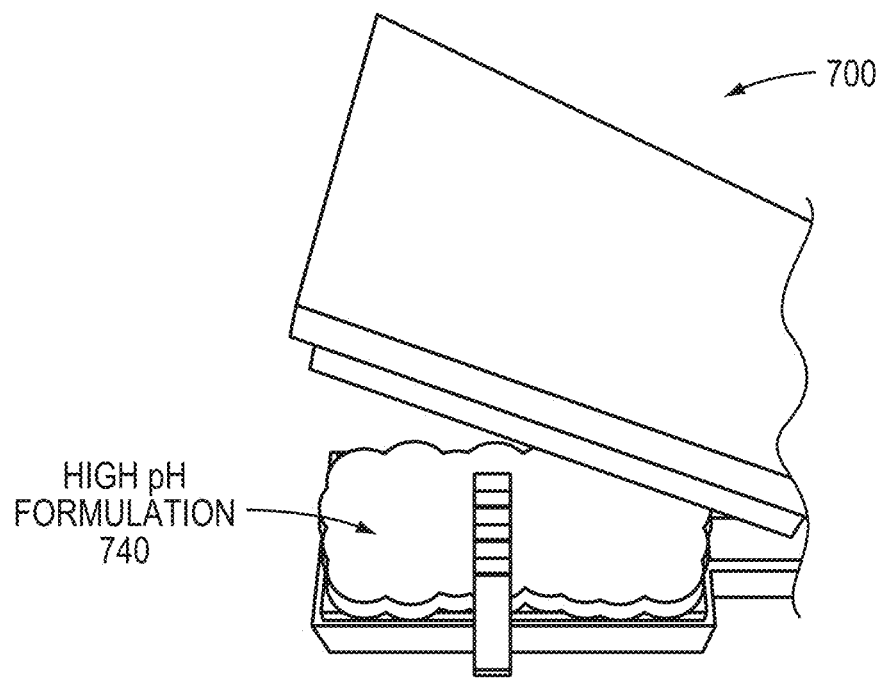

FIG. 23B is a partial view of the hair styling device of FIG. 20, in the first configuration and showing an electrolyte formulation disposed thereon.

Figure 24:
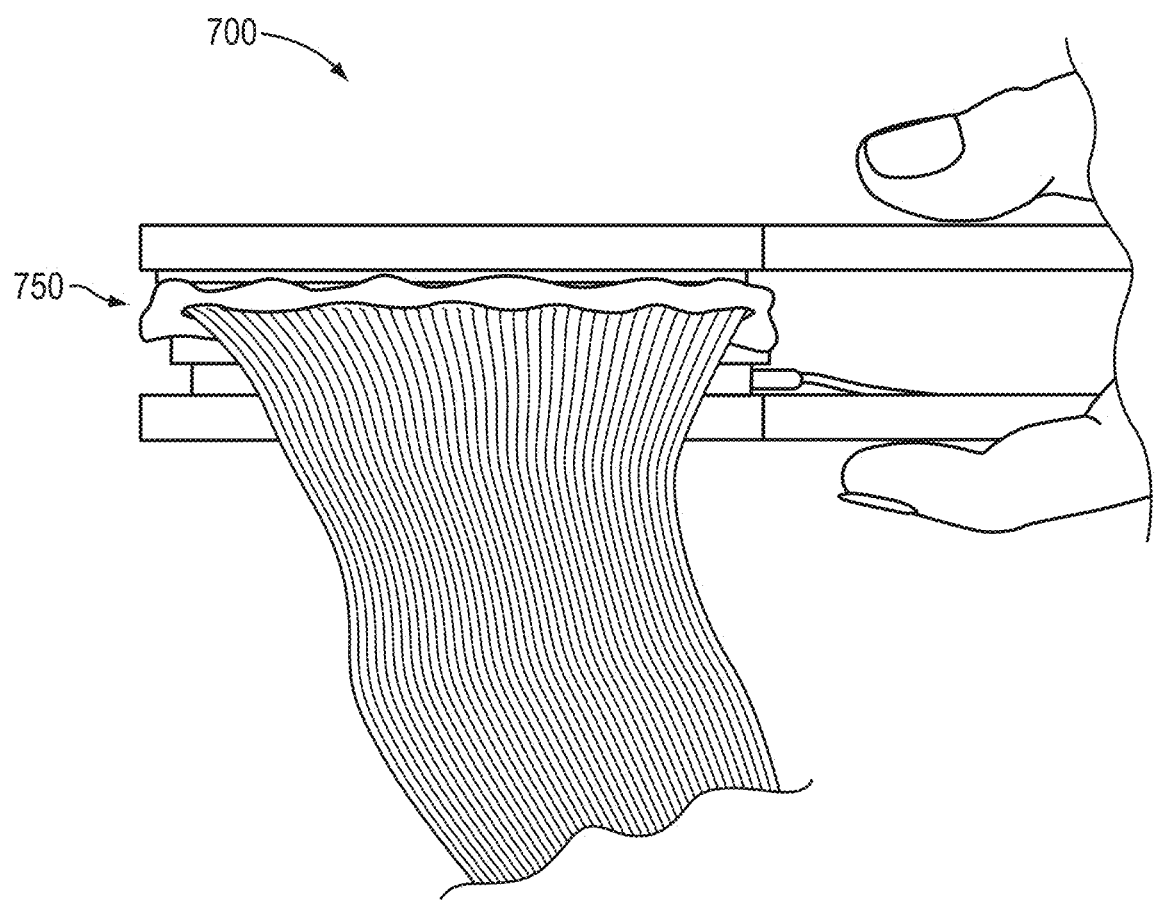

FIG. 24 is a partial view of the hair styling device of FIG. 20, in the second configuration and in use.

Figure 25:
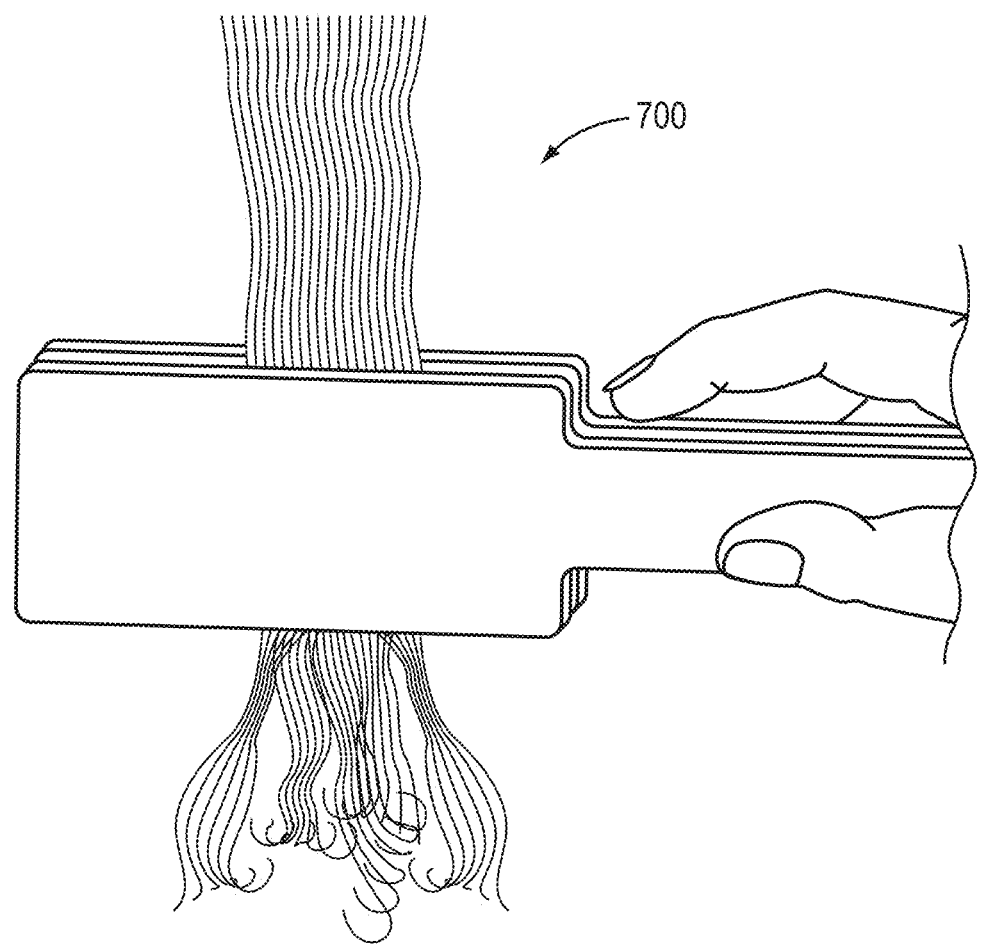

FIG. 25 is a partial view of the hair styling device of FIG. 20, in the second configuration and in use.

Figure 26:
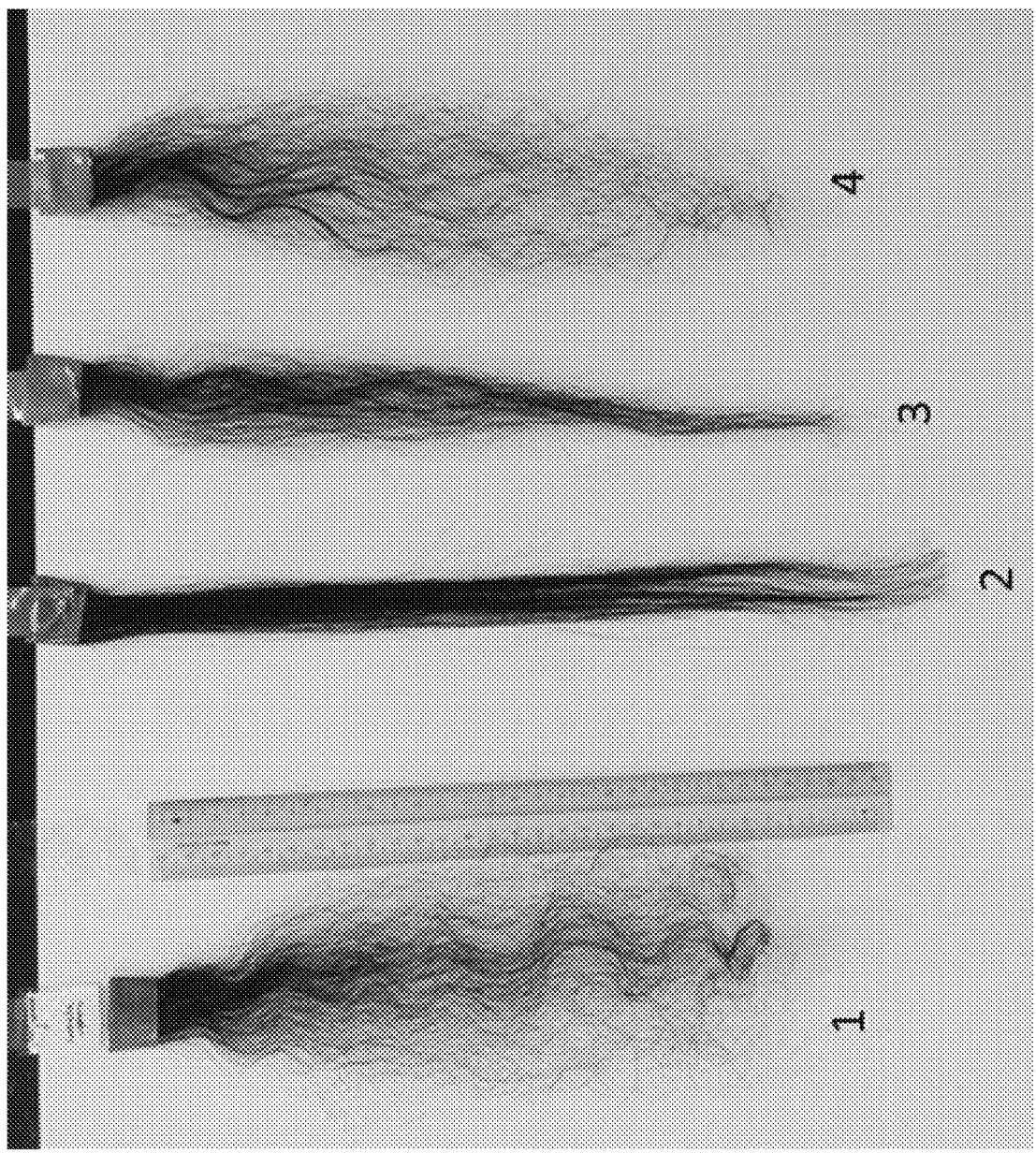

FIG. 26 shows various samples of bundles of naturally wavy hair straightened using various straightening treatments.

Figure 27:

FIG. 27 shows various samples of bundles of naturally wavy hair straightened using a hair styling device according to an embodiment of the present disclosure.

FIG. 28A shows a bundle of unstraightened hair, FIG. 28B shows the hair straightened using a hair styling device according to the present disclosure, and FIG. 28C shows the bundle of straightened hair of FIG. 28B after drying.

FIGS. 29A-40C show results of testing the hair styling device of the present disclosure are provided. Subjects were treated as described below, with sections of hair being (1) left untreated, (2) treated with a device of, and according to a method of, the present disclosure, (3) washed/dried, and/or (4) straightened with a regular "flat iron."

Figure 41A:
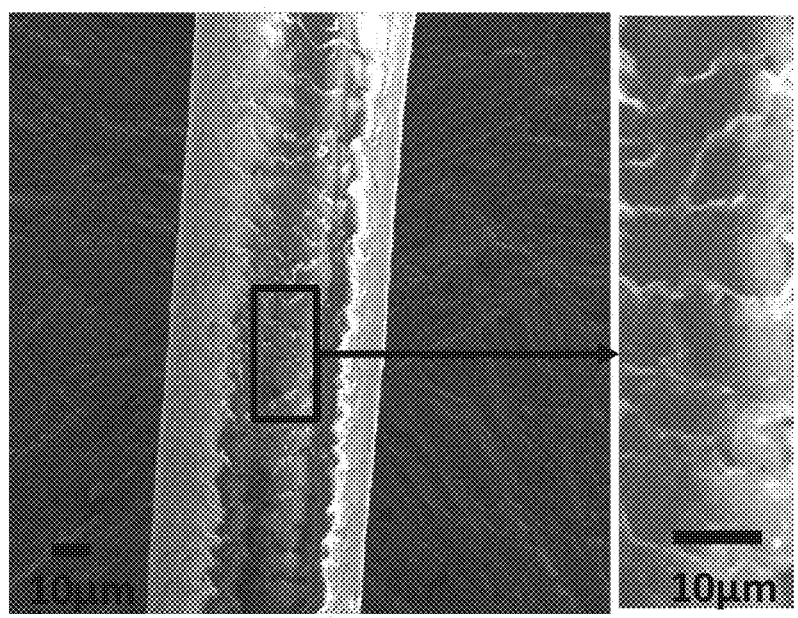
Figure 41B:
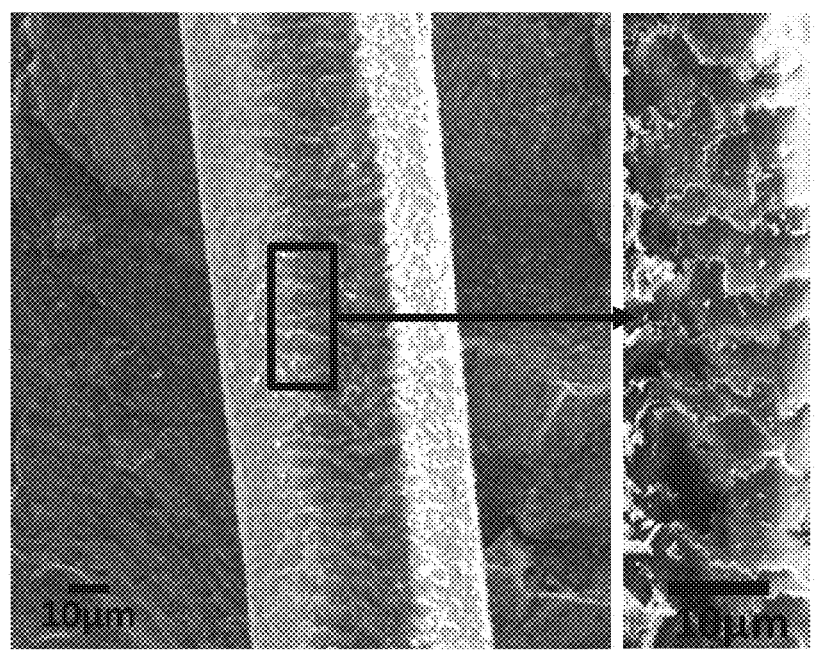

FIG. 41A shows a scanning electron microscopy (SEM) micrograph of a strand of untreated hair. FIG. 41B shows the strand of hair exposed to the alkaline environment of a cathode.

FIG. 42 shows a portion of a cellulose microparticle that includes a plurality of conjugated carboxylic groups which induce a negative charge on the microparticle.

FIG. 43A shows an SEM micrograph of a portion of untreated hair. FIG. 43B shows an SEM micrograph of the strand of hair with gold nanoparticles coupled to multifunctional polymer molecules incorporated into the hair using electrolysis.

Figure 44:

FIG. 44 shows a portion of a strand of hair that includes a plurality of cellulose microparticles electrostatically coupled to multifunctional polymer molecules incorporated into the hair using electrolysis.

Figure 45:
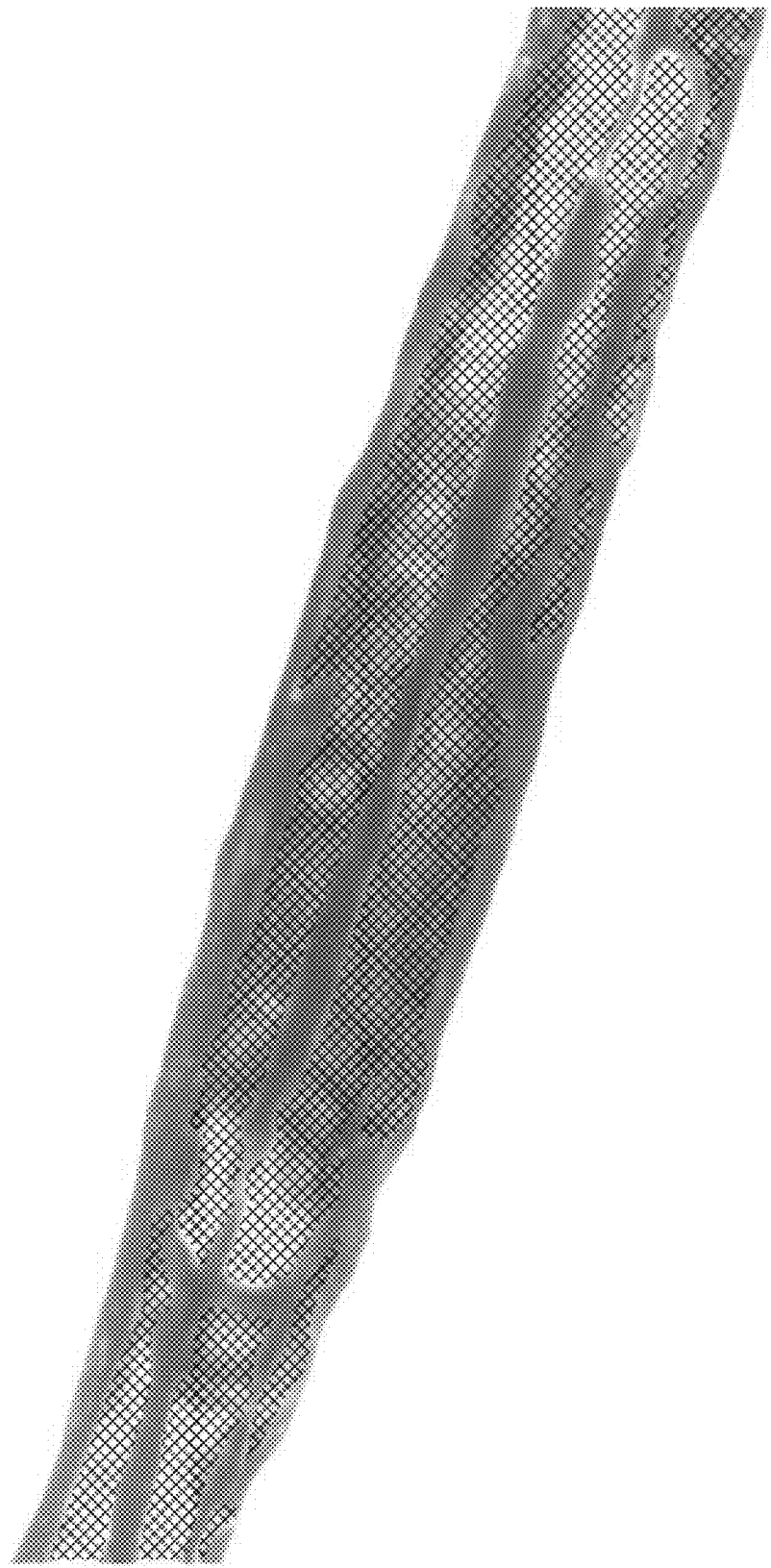

FIG. 45 shows a portion of a strand of hair that includes a plurality of cellulose microparticles electrostatically coupled to multifunctional polymer molecules incorporated into the hair using electrolysis and is further colored green with water based color.

FIG. 46A shows a portion of a strand of naturally white hair that was immersed in a colored pigment solution and washed. FIG. 46B shows a colored pigment incorporated into a naturally white hair using electrolysis.

DETAILED DESCRIPTION

Embodiments described herein relate generally to devices and methods for styling hair, and in particular, to devices and methods for styling hair using electrolysis. Conventional methods that use chemicals and/or heat for styling hair have several disadvantages. For example, the heat and/or chemicals can cause significant damage to the hair-root and scalp, can take a long time to perform, can raise safety concerns, and often require the assistance of a professional hair dresser which can be expensive.

Thus there is a need for new hair styling technologies that can allow hair styling without the use of heat and/or chemicals, and be simple enough to be used by untrained users.

Human hair includes a dense network of the protein keratin that is bound together by disulfide bonds, hydrogen bonds, and ionic bonds. These bonds, particularly the disulfide bonds can be decomposed in alkaline pH and reducing environment, for example, in an electrolyte near the negative electrode with or without or a reducing agent. The disulfide bonds can be urged to reform by oxidation in a neutralizing, alkaline or an acidic pH, for example, in the electrolyte near the other grounded, less negative or positive electrode respectively, as described herein. In this manner, the hair can be styled, for example, curved hair can be straightened or any other styling operation described herein can be performed. Exposing the hair to high alkaline pH produced by electrolysis alone is sufficient to achieve breaking of the disulfide bonds and forming of the lanthionization bonds at these sites. Hair styling devices and methods for styling hair using electrolysis described herein can be used to produce a highly localized alkaline or acidic "electrolysis zone" in an electrolyte. Hair can be exposed to the alkaline and/or acidic zones produced in the electrolyte to alter the sulfhydryl, ionic and/or hydrogen bonds included in the hair, and thereby style the hair using electrolysis.

In some embodiments, a method for styling hair includes arranging a section of hair between a first electrode and a second electrode. The section of hair is contacted with an electrolyte before being arranged between the first and second electrodes, after being arranged between the first and second electrodes, and/or concurrently with being arranged between the first and second electrodes. The method further includes causing the first electrode to have a first negative potential, and causing the second electrode to have a second potential, such that the absolute value of the first negative potential is greater than the absolute value of the second potential, and such that the difference in electrical potential between the first electrode and the second electrode creates an electrolysis zone between the first electrode and the second electrode.

In some embodiments, a method of styling hair using a hair styling device having a first electrode electrically coupled to a DC power module and a second electrode includes disposing hair between the first electrode and the second electrode, disposing an electrolyte on the hair, causing the first electrode to have a first potential and the second electrode to have and a second potential. The absolute value of the first potential is different than the absolute value of the second potential and is sufficient to produce a current between the first electrode and the second electrode of at least 1.5 amperes.

In some embodiments, an apparatus of the present disclosure includes a first generally flat electrode, a second generally flat electrode, and a connector coupled to the first electrode and the second electrode. The connector is configured to provide relative movement of the first and second electrodes relative to each other between a first configuration in which the first electrode is spaced a first distance from the second electrode such that a section of hair can be arranged between the first electrode and the second electrode, and a second configuration in which the first electrode is spaced a second non-zero distance from the second electrode, the second distance being less than the first distance. The apparatus also includes a power supply electrically coupled to the first electrode and operable to provide a first negative potential at the first electrode. The second electrode is disposed and configured to be electrically coupled to at least one of the power supply and a ground, and operable to provide a second negative potential at the second electrode. The first electrode and the second electrode are operable to create an electrical potential difference therebetween, and to create a substantially alkaline zone in an electrolyte disposed between the first and second electrodes.

In some embodiments, a system of the present disclosure includes a first electrode, a DC voltage module electrically coupled to the first electrode and configured to provide a first potential at the first electrode, and a second electrode spaced from the first electrode. The second electrode is disposed and configured to be electrically coupled to a ground, and operable to provide a second potential at the second electrode. The absolute value of the second potential is less than the absolute value of the first potential.

In some embodiments, a system of the present disclosure includes a first electrode and a DC voltage module configured to electrically couple the first electrode to a power supply. The voltage regulation module is operable to provide a first negative potential at the first electrode when the DC voltage module is electrically coupled to the power supply. An absolute value of the second potential is less than an absolute value of the first potential. The system also comprises a second electrode that is electrically coupled to a ground such that an absolute value of the second potential is less than an absolute value of the first potential.

In some embodiments, a method of styling hair as disclosed herein is performed using a hair styling device that includes a first electrode disposed on a first elongate member and a second electrode disposed on a second elongate member, the and the hair styling device being movable between a first configuration in which the first electrode and the second electrode are spaced a first distance from each other, and a second configuration in which the first electrode and the second electrode are spaced a second distance from each other, the second distance less than the first distance. The method comprises disposing an electrolyte on a section of hair, disposing the hair styling device in the first configuration, disposing the section of hair between the first electrode and the second electrode when the hair styling device is in the first configuration, moving the hair styling device to the second configuration, causing the first electrode to have a first negative potential, and causing the second electrode to have a second potential. The absolute value of the first negative potential is greater than the absolute value of the second potential, and the difference in electrical potential between the first electrode and the second electrode induces a current between the first electrode and the second electrode of at least about 1.5 amperes.

As used herein, the terms "about" and "approximately" generally mean plus or minus 10% of the value stated, for example about 1 ampere would include 0.9 amperes to 1.1 amperes, about 10 amperes would include 9 amperes to 11 amperes, etc.

As used herein, the term "bias" can refer to a voltage at a location in a circuit brought about by a connection to a power supply and/or a ground, or a voltage induced at a location in a circuit as a result of another location in the circuit being electrically tied to a power supply and/or ground.

Conventional electrolytic cells are configured to include a cathode and an anode such that a reducing zone is produced proximate to the cathode, and an oxidizing zone is produced proximate to the anode within the electrolyte, with a pH neutral zone disposed between the acidic and the alkaline electrolysis zones. By contrast, embodiments of the hair styling device described herein can be configured to include a first electrode and a second electrode configured to produce reducing zones proximate to their respective surfaces and/or extending from a surface of the first electrode toward or to a surface of the second electrode. In some embodiments, an alkaline electrolysis zone can be produced in the vicinity of a negatively charged electrode. In some embodiments, a wide alkaline electrolysis zone can be produced between two negatively charged electrodes by providing a first electrode which is biased at a higher negative voltage than the second electrode. When electrolysis happens between two negative electrodes with the first electrode having a higher negative potential than the second electrode, the first electrode produces a reducing environment by generating hydrogen and the second electrode generates an oxidizing environment by generating oxidizing elements or molecules. The reducing environment may occupy a substantially larger volume between the electrodes than does the oxidizing environment. In other embodiments, only a cathode or an anode is employed, and is paired with a ground electrode (e.g., an electrode maintained at zero volts). In such configurations, a predominantly alkaline electrolysis zone (when the electrolytic cell includes a cathode) or a predominantly acidic electrolysis zone (when the electrolytic cell includes an anode) is produced within the electrolyte, such that the alkaline or the acidic electrolysis zone spans almost the entire distance between the two electrodes. In still other embodiments, a wide acidic electrolysis zone can be produced between two positively charged electrodes by providing a first electrode which is biased at a higher positive voltage than the second electrode.

Electrolysis is the process of passing a direct electrical current through a liquid, for example, an aqueous electrolyte. This can be achieved by contacting two electrodes having a liquid disposed therebetween and biasing one or both electrodes at a negative voltage to produce a difference in electrical potential. At a negatively charged electrode (e.g., a "cathode"), water molecules included in the aqueous electrolyte decompose to produce $H^+$ and $OH^-$ (i.e., "in situ"). The $H^+$ can be consumed by reduction to hydrogen gas such that a region surrounding the cathode has a highly reducing and alkaline pH (e.g., a pH of about 12-14). In some embodiments, both electrodes of the hair styling device can be negatively charged (i.e., biased or configured to have a negative electrical potential), and thus both electrodes may have an alkaline region adjacent to their respective charged surfaces. As such, all or substantially all of the region between a first negatively charged electrode and a second negatively charged electrode, as defined by their respective charged surfaces, may comprise a uniform, substantially uniform, or non-uniform alkaline "electrolysis zone." In some embodiments, an electrode can be positively charged, in which case water molecules of the liquid decompose to produce $H^+$ and $OH^-$. The $OH^-$ can be consumed by oxidation to oxygen gas, the free $H^+$ ions combine with a water molecule to produce $H_3O^+$ (hydronium) ions, such that a region proximate to the anode has a highly acidic and oxidizing pH (e.g., a pH of about 1-4).

In some embodiments, electrical voltages can be applied to a first electrode and a second electrode, which are in contact with an electrolyte solution, for example, a sodium chloride aqueous solution or any other electrolyte (e.g., salt-containing) solution described herein. This can urge the electrolyte to undergo electrolysis at a suitable voltage and current and produce an electrolysis zone between the first electrode and the second electrode. The first electrode can be negatively charged, such that the electrolytic breakdown of the electrolyte produces H$^+$ and OH$^-$ ions "in situ" at the first electrode (the cathode), and the region surrounding the first electrode has a highly reducing and alkaline and/or basic environment (e.g., a pH of about 12-14). The second electrode can have a negative potential (e.g., electrically coupled to ground), and a lower pH than the region surrounding the first electrode (e.g., a pH of about 1 at or near the surface of the second electrode) or a potential of at or near zero volts (i.e., grounded). In some embodiments, a small amount of positive charge can be induced on a grounded second electrode due to the negative potential on the first electrode. Either configuration allows the OFF ions to travel through the electrolyte to the second electrode such that the alkaline zone spans substantially the entire width between the first electrode and the second electrode. In some embodiments, the OFF ions can be neutralized at the second electrode to produce H$_2$O and O$_2$ gas with a very low amount of free H$^+$ ions. In some embodiments, a wide alkaline electrolysis zone is be produced by biasing the first electrode at a first negative voltage and having a second negative voltage at the second electrode. The first negative voltage can be substantially more negative than the second negative voltage such that the wide alkaline electrolysis zone spans substantially the entire distance between the first electrode and the second electrode. When the voltages are removed from the electrodes, the electrolysis zone can disappear almost immediately.

In some embodiments, a first electrode and a second electrode can be brought in close proximity to hair, for example, human hair to produce the electrolysis zone in the vicinity of the hair. This can urge the hair to undergo physical changes. For example, when exposed to an alkaline electrolysis zone, the hair swells. Without being bound by any particular theory, the swelling of the hair can be attributed to the breakdown of the disulfide bonds that fasten the hair proteins together. For example, an untreated portion of a hair may include a plurality of disulfide bonds, ionic bonds and hydrogen bonds randomly distributed in the hair. After exposure to an alkaline electrolysis zone, for example, having a pH of about 13 or about 14, produced by a cathode (i.e., a negatively charged electrode), the distribution of bonds within the hair can change, for example because the reducing environment of the alkaline electrolysis zone can open the cuticle of the hair and break a substantial portion of the disulfide bonds and, when coupled with mechanical stretching (e.g., straightening) of the portion of the hair by the electrodes, can achieve straightening of the hair. Many of the disulfide bonds can undergo lanthionization as well. A small portion of the disulfide bonds can, however, persist. If subsequently exposed to a neutral pH environment, the disulfide bonds, the ionic and/or the hydrogen bonds can reform, and the cuticle can close. In this manner, the portion of the hair can be styled. For example, exposing hair to an alkaline environment can cause it to transition from a wavy or curly shape into a straight or substantially straightened shape.

On the other hand, when a portion of hair is exposed to an acidic electrolysis zone, the hair contracts, possibly because of reformation of bonds, new bonds, and/or crosslinking which can fasten the hair proteins together. Thus, whether an electrolysis zone (or region thereof) produced between the first electrode and the second electrode is alkaline or acidic can determine a corresponding reconfiguration of the location and/or structure of all the bonds stabilizing the hair structure (i.e., the location of the disulfide bonds included in the hair) and, thereby, restyle the hair. For example, exposing hair to an acidic environment can cause it to transition from frizzy to smooth. Furthermore, the dense keratin network of hair can readily open up when exposed to an alkaline pH. This can allow permeation of the hair with various molecules, for example, colors, dyes, anti-frizz agents, oils, straighteners, moisturizers, shape memory materials or any other molecules used for styling hair.

In some embodiments, an electrolyte container/reservoir, such as an absorbent "pad," is included in the hair styling device and can be configured to receive and/or contain a volume of electrolyte and fluidically communicate electrolyte between the first electrode and the second electrode. A DC voltage module is included in the hair styling device and is configured to provide electrical power directly to at least one of the electrodes. In some embodiments, the first electrode and/or the second electrode can be electronically coupled to the DC voltage module via a control module to adjust/vary a setting of the hair styling device corresponding to a selected applied voltage. The hair styling device is configured to electrolytically decompose the sulfhydryl bonds included in a portion of the hair of a user that is disposed between the first electrode and the second electrode, and thereby style the hair of the user.

FIG. 1 shows a schematic illustration of a hair styling device 100 according to an embodiment. The hair styling device 100 includes a first electrode 110a, a second electrode 110b, a DC voltage module 140, optionally an electrolyte 150, and optionally a control module 170. The first electrode 110a and the second electrode 110b (collectively referred to as the "electrodes 110") are configured to interact with the hair of the user U and style the hair using electrolysis. The hair styling device 100 can be used by a user U to style the hair of the user U or of another individual (e.g. the user U can be a hair stylist using the device 100 on a customer's hair), for example to straighten, curl, attach nanoparticles to, color, highlight, moisturize, thicken, control frizz, alter glossiness, deodorize, augment moldability, add fragrance to, or bleach hair.

The electrodes 110 can be made of a conductive material, for example, graphite, platinum, aluminum, copper, stainless steel, alloys, other metals, ceramics, any other suitable conductive material, and or a combination thereof. In some embodiments, the electrodes 110 can also be coated with a corrosion resistant material, for example, gold, platinum, aluminum, any other corrosion resistant material or combination thereof. The electrodes 110 can be substantially flat electrodes, for example, plate type electrodes. In some embodiments, the surface of the electrodes 110 can include features, for example, contours, ridges, or any other features configured to aid in styling the hair of a user. The electrodes 110 can be spaced apart by a distance (not shown) that defines an electrolysis zone. In some embodiments, any one of the electrodes 110 can include a masking layer disposed over the electrode 110 to create a separation layer between the electrode 110 and the hair, within the hair styling device 100. In some embodiments, the first electrode 110a and/or the second electrode 110b includes an absorbent pad, sponge, or other porous material that serves as an electrolyte reservoir and can contain a volume of electrolyte for use (e.g., for the continuous supply of electrolyte) during electrolysis. The absorbent pad can be positioned such that during use the absorbent pad is disposed between the first electrode 110a and the second electrode 110b. In some embodiments, the pad serves to "mask" the surface of the second electrode 110b (or the surface of the electrode having the higher potential) such that any acidic region adjacent to the second electrode 110b does not contact the hair, but the hair can still be exposed to an alkaline electrolyte and the OH— ions for styling. In such embodiments, hair may be disposed adjacent to or on the absorbent pad during use. The absorbent pad can be configured to prevent contact between the first electrode 110a and the second electrode 110b. In some embodiments, an electrolyte reservoir may not be required.

In some embodiments, the first electrode 110a and the second electrode 110b can be disposed on respective flat bases or "elongate members." The first electrode 110a and the second electrode 110b may be connected via a connector (such as a hinge or other mechanical connection) and configured for relative movement with respect to one another. For example, the electrodes 110 can be moveable into a first configuration and a second configuration, where the first electrode 110a and the second electrode 110b are spaced closer together in the second configuration than in the first configuration. The electrodes 110 can be disposed parallel or substantially parallel to each other and separated by a distance (e.g., through the use of mechanical standoffs and/or by virtue of the thickness of an electrolyte reservoir, such as an absorbent pad, disposed therebetween) that at least partially defines the electrolysis zone. In such embodiments, a cover portion can be included in the hair styling device 100. The cover portion can be substantially flat and configured to be moved between an open configuration and a closed configuration such that in the closed configuration, the cover portion is disposed parallel to and in proximity of the electrodes 110. In this manner, the cover portion can be used to clamp the hair of the user U disposed on the electrodes 110, between the electrodes 110 and the cover portion. In some embodiments, mating electrodes can be disposed on a surface of the cover portion proximal to the electrodes 110. The mating electrodes can be configured to mate with the working electrodes 110 when the cover portion is in the closed position. For example, the cover portion can be moved in the second configuration such that the hair of the user disposed on the electrodes 110 is clamped between the electrodes 110 and the mating electrodes. The second pair of mating electrodes can have substantially the same potentials as the electrodes 110, such that an electrolyte zone is generated on both sides of the hair clamped between the electrodes 110 and the mating electrodes. In this manner, a stronger electrolysis zone can be produced around the hair for more efficient styling of the hair. In some embodiments, the hair styling device 100 can also include a frame (not shown), for example, a plastic or polycarbonate frame for housing at least a portion of the electrodes 110. The frame can include features to house a temporary, disposable reservoir (not shown) for holding the electrolyte, for example the pad as discussed above. In some embodiments, the frame can also include fluidic channels for communicating the electrolyte from an electrolyte reservoir to a temporary reservoir.

In some embodiments, any one of the electrodes 110, for example, the first electrode 110a, can be substantially cylindrical (e.g., having a circular cross-section). In some embodiments, the second electrode 110b can be a hollow cylinder, shaped and sized to coaxially slide over the first electrode 110a such that a gap remains between the first electrode 110a and the second electrode 110b. The user U can wrap her hair over the first electrode 110a and then slide the second electrode 110b over the hair. Current can be passed in the presence of the electrolyte 150, to perform electrolysis to curl the hair. In some embodiments, the coaxial electrodes 110 can be immersed in an electrolyte. In some embodiments, the electrolyte can be applied to the hair of the user beforehand. In some embodiments, the first electrode 110a can be in the form of a cylinder and the second electrode 110b can be in the form of a ribbon electrode. The user U can wrap the hair around the first electrode 110a and then wrap the second electrode 110b, i.e. the ribbon electrode around the hair. In the presence of the electrolyte, electrolysis can be performed to style (e.g., curl) the hair. In some embodiments, the hair styling device 100 can include a suction mechanism, for example, a vacuum to "suck" the hair into a space between the electrodes 110 to style the hair. In some embodiments, the electrodes 110 can be in the form of a roller brush. In some embodiments, the electrodes 110 can be in the form of combs.

The DC voltage module 140 can be configured to bias one or both of the electrodes 110. The DC voltage module 140 can be coupled directly to the first electrode 110a and/or the second electrode 110b (e.g., via electrical wiring and/or components). Module 140 also can include a power supply, such as a battery, or other means to connect to an external power supply (such as a wall outlet). The DC voltage module is configured, by way of its architecture and components, to provide electrical potential to one or both of the electrodes 110. In some embodiments, the DC voltage module 140 can include a plurality of rechargeable batteries, for example, li-ion coin cells, 9 volt cells, D cells, or any other suitable cells, disposed in series within a sealed container, for example, a cylindrical container to form the power supply (not shown).

In some embodiments, the DC voltage module 140 can be configured to supply a potential of at least about +/−5 or 6V, about +/−11 to 13 V, about +/−24 V, or as much as about +/−50V, to one of the first electrode 110a and the second electrode 110b, and can be rated for a current of up to about 13 A. The DC voltage module 140 and associated circuitry can further be configured to supply a difference in electrical potential between the first electrode and the second electrode of at least about 5 or volts ("V"), or at least about 10 V, or at least about 12 V, or in the range of about 5 V to about 20 V. In some embodiments, the DC voltage module 140 is configured such that a voltage at the second electrode 110b is about −12V (for example, when the voltage at the first electrode 110a is about −24V, thus amounting to a 12 V difference in potential). In some embodiments, the DC voltage module 140 can include capacitors, resistors, inductors, switches, relays, fuses, and/or the like.

The DC voltage module 140 and associated circuitry also can be configured such that, during use, a current between the first electrode 110a and the second electrode 110b is at least about 1.5 amperes ("A"), or about 4.5 or 5 A to about 6 or 8 A, or may be in the range of about 2 A to about 12 A, or may be as high as about 10 A. In some embodiments, the DC voltage module 140 can include a magnetic field fluctuation producing source that may induce electric current and electrolysis in the hair. In some embodiments, the DC voltage module 140 includes two power supplies, e.g. including one or more batteries and/or the means to connect to an external power supply (such as a wall outlet).

The DC voltage module 140 can also include a housing (not shown) to house a power supply. In some embodiments, the voltage module housing can be in the form of a hollow cylinder that is sealed using end caps (not shown). At least one of the end caps can include electrical couplings for coupling the DC voltage module 140 to an optional control module 170. At least one of the end caps can also include a plurality of switches, such that the switches can be toggled in a predetermined combination for power supply from battery, battery charging, or direct power supply from an external source, for example, a docking unit.

The electrolyte 150 can be a solution of water and a salt. The salt concentration (i.e., molarity, "M") is preferably relatively high, such that a desired level of anion is present within the electrolyte during use. The higher salt concentration can increase the conductivity of the electrolyte and, in turn, can increase the OH— ion concentration. Higher salt concentrations and conductivity can result in higher currents during use. For example, the salt concentration can be about 2M, or greater than about 2M, or about 3M, or from about 1M to about 5M, or at least about 2.5M, or from about 2.5M to about 3.5M, or from about 2M to about 3M, or from about 1.8M to about 2.5M. The maximum molar concentration may depend on the solubility of the particular salt. The salt can be any suitable salt which is safe for human exposure, for example, sodium bicarbonate, sodium chloride (NaCl), sodium carbonate, sodium sulfate, sodium iodide (NaI), magnesium sulfate, magnesium chloride, calcium chloride, potassium chloride, potassium iodide, potassium sulfate, potassium bicarbonate, potassium carbonate, sodium acetate, sodium citrate, sodium phosphate, chromium chloride, aluminum chloride, Epsom salt, any other suitable salt or combination thereof.

In some embodiments, the electrolyte includes a solvent (e.g., water), a salt (e.g., NaCl), and at least one of: a chlorine formation inhibitor (to prevent the formation of chlorine during electrolysis, e.g., NaI), an electrolysis foam booster, a wetting agent, a humectant, a hydrophobic agent, ascorbic acid, and a surfactant. In some embodiments, the electrolyte 150 comprises: about 43.7% water as an electrolyte solvent, about 16.7% sodium chloride (NaCl) to enhance electrolysis and/or to stabilize dynamically generated OH— ions as sodium hydroxide (NaOH), about 8.5% sodium iodide (chlorine formation inhibitor), about 4.8% cocamidopropyl betaine to boost electrolysis foam and/or to serves as a hair wetting agent, about 6.6% glycerol to act as a humectant, decrease evaporation and/or maintain fluidity, about 2% coconut oil as a hydrophobic agent, about 1.6% mineral oil as a hydrophobic agent, about 4% silicone oil as a hydrophobic agent, about 2% petroleum jelly as a hydrophobic agent, and about 10.1% PEG 40-hydrogenated castor oil to serve as a surfactant for dissolving the hydrophobic agents or to obtain a desired consistency.

In some embodiments, a solid electrolyte or a gel electrolyte, disposed between the first electrode 110a and the second electrode 110b, is used instead of an aqueous electrolyte.

Electrolytes of the instant disclosure are formulated to facilitate electrolysis and/or provide a specific styling function for styling hair using embodiments of the hair styling device described herein, or any other hair styling device. For example, in some embodiments, the electrolyte can be formulated to provide an alkaline pH, for example, to create and/or enhance an alkaline pH zone, or to facilitate the production of an alkaline pH zone produced between a first biased electrode and a second electrode. In some embodiments, the electrolyte 150 produces a relatively high alkaline pH between a negatively charged electrode (e.g., the first electrode 110a) and an electrode that is electrically coupled to ground (e.g., the second electrode 110b). For example, the electrolyte 150 can be formulated to produce, during use, a pH in the region adjacent the first electrode that is greater than about 10, and often greater than about 12. Higher pH values can facilitate faster and/or more effective styling of the hair, and therefore the pH in the regions adjacent the first electrode can be as high as 14. In some embodiments, the electrolyte 150 can include hydroxides of metals such as aluminum, magnesium, calcium and other metals that have very low solubility in water or neutral pH salt solutions, but can readily dissolve in the presence of free $H^+$ ions in the electrolyte 150. Due to their poor solubility in neutral aqueous solutions they do not contribute to the alkaline pH when mixed into the electrolyte 150 even though such salts include hydroxide molecules in their molecular structure. Furthermore, such salts also neutralize any free $H^+$ ions present in the electrolyte 150. Salts can be included in the electrolyte 150 in the form of a solution, a suspension, nanoparticles, or colloids. Examples of such salts include but are not limited to aluminum hydroxide, magnesium hydroxide, calcium hydroxide, aluminum carbonate, magnesium carbonate, calcium carbonate, bismuth sub salicylate (PEPTO-BISMOL®), and sodium alginate.

In some embodiments, the DC voltage module 140 may be electrically coupled to at least one of the first electrode 110a and the second electrode 110b via an optional control module 170. The optional control module 170 can include electronic components and/or accessories for controlling (e.g., varying, for example by way of an adjustable interface that can be adjusted or set by a user) the voltage across the electrodes 110, and/or the direction or amount of current. The control module can include a variable resistor (not shown), for example, a rheostat or potentiometer, a directional switch, for example, a DPDT switch (not shown), and/or other control circuitry. The variable resistor can, for example, be a dial type resistor that can be used to manually adjust the voltage difference across and current flow between the electrodes 110 and thereby control the intensity of electrolysis. The directional switch can be used to reverse or change the polarity on the first electrode 110a and the second electrode 110b such that either one of the first electrode 110a and the second electrode 110b can be used as the anode or the cathode, or so that either of the electrodes is electrically connected to an output of voltage module 140.

In some embodiments, the first electrode 110a can be biased at a negative voltage by the DC voltage module 140, by way of its electrical connection thereto via a first electrical connector, and can serve as a cathode. The second electrode 110b can be electrically coupled to ground (e.g., via a resistor), for example by way of a second electrical connector, and thus have a voltage that is also negative but lower in absolute value than the negative voltage at the first electrode 110a, and can serve as an anode. Thus, the polarity (i.e., negative or positive voltage value) of the first electrode 110a and the second electrode 110b (the cathode and the anode) can be the same (e.g., both negative). The resistor can be disposed between the second electrode 110b and the second electrical connector.

The absolute value of the voltage at the first electrode 110a is different from the absolute value of the voltage level at the second electrode 110b. For example, the absolute value of the voltage at the first electrode 110a can be substantially greater than the absolute value of the voltage level at the second electrode 110b (e.g., a difference of 12 V). Depending on the absolute value of the voltage at the first electrode, the absolute value of the voltage at the second electrode can be less than half the absolute value of the first potential. In some embodiments, the difference in electrical potential between the first electrode 110a and the second electrode 110b is at least about 5 V or 6 V, or at least about 10 V to about 12 V, or in even in the range of about 5 V to about 20 V.

The voltage of the first electrode 110a depends on the output of DC voltage module 140, and may be in the range of about −6 V to about −50 V. In some embodiments, the absolute voltage of the second electrode 110b is less than 1 V; and other embodiments it may be about 10-15 volts less than but have the same polarity as that of the first electrode. In some embodiments, the voltages and/or polarity can be reversed such that the first electrode 110a functions as an anode and the second electrode 110b functions as a cathode, where the cathode refers to the electrode having the lowest voltage.

A suitable electrolyte can be disposed in the space between the electrodes 110. This can be accomplished, for example, by applying electrolyte to a pad disposed on one of the electrodes 110, or by applying the electrolyte 150 to a section of hair and disposing the section of hair between the electrodes 110. Due to the difference in voltage between the first electrode 110a and the second electrode 110b, the spacing between the electrodes 110 with respect to one another, and the type of electrolyte disposed between them, an electrolysis zone is created between the first electrode 110a and the second electrode 110b. The electrolysis zone can be substantially alkaline or "basic" (i.e., a reducing zone) and span most or all of the distance between the first electrode 110a and the second electrode 110b. The electrolysis zone can have a pH of at least about 10, or about 12, or as much as 14, and can be in the vicinity of at least one of the first electrode 110a and the second electrode 110b. In some embodiments, the electrolysis zone is non-uniform, and comprises a large alkaline zone extending from the first electrode 110a as well as a relatively small acidic zone adjacent the second electrode 110b and, for example, having a pH of less than about 6, or between 1 and 3. In such embodiments, a further region or interface can exist between the alkaline zone and the acidic zone that is substantially neutral in pH.

An absorbent pad can be disposed on the second electrode 110b such that the section of hair, when received between the first electrode 110a and the second electrode 110b, is substantially confined to the alkaline zone and not in contact or substantially not in contact with the acidic zone and, optionally, also not in contact or substantially not in contact with the neutral zone, even when an acidic electrolysis zone is present in the vicinity of (or at the surface of) the second electrode 110b. In some embodiments, the pH of electrolyte contacting the section of hair disposed between the first electrode 110a and the second electrode 110b is at least about 13.

During use, the hair styling device can be positioned such that the first electrode 110a and the second electrode 110a are disposed about (i.e., on opposing side of) a section of hair to be styled. The hair can be in contact with electrolyte 150 and disposed at least partially within an electrolysis zone between the first electrode 110a and the second electrode 110a, the electrolysis zone resulting from an applied voltage of the DC voltage module 140. The hair styling device 100 can be moved across the section of hair such that successive regions of a section of hair are styled by exposure to the electrolysis zone.

In some embodiments, a process of the disclosure is as follows: person's (e.g., a client's) hair is washed and/or towel dried so that it is still damp prior to application of the hair styling device 100. The hair is then sectioned, and electrolyte 150 formulation is dispensed onto dry electrodes 110 of the hair styling device 100. A user U can then position one of the sections of hair on one of the electrodes 110 and bring the first electrode 110a and the second electrode 110b into proximity to one another such that they clamp about the section of hair. The user U can the wait and observe until electrolysis begins, for example evidenced by bubble formation between the electrodes 110 (e.g., thereby achieving a pH of about 14 between the electrodes 110). The user U can then slide the hair styling device 100 across the section of hair in a "stroke" (e.g., from a root end of the hair section to an end of the hair section). The user U can apply a plurality of strokes (for example 5 strokes or less) to the section of hair, for example until the section of hair is visibly straight. The user U may replenish the electrolyte 150 formulation on at least one of the electrodes 110 as needed to maintain electrolyte volume. Once styling is complete, the hair styling device 100 can be removed from the section of hair. After styling (i.e., after the hair styling device 100 has been removed from the section of hair), a number of additional processing steps can be performed. For example, the section of hair can be washed with water and conditioner or serum. Additionally or alternatively, the section of hair can be washed with neutralizing shampoo and washed off, followed by a condition step. Next, the section of hair can be blow-dried and flat ironed.

In some embodiments, the electrolysis zone (i.e. the reducing zone), or an alkaline or acidic portion thereof, can be highly localized to the surface of one or both of the electrodes 110. In some embodiments, only one of the first electrode 110a and the second electrode 110b might be configured to be biased at a negative voltage and serve as the cathode while the other electrode (e.g., the second electrode 110b) can be grounded (i.e., at or near zero volts) or coupled to an electrical ground (the latter case in which both electrodes 110 would be negative). In such embodiments, the electrolysis zone can be predominantly alkaline (i.e., basic). The second electrode 110b can consume the OH⁻ produced at the negatively charged first electrode 110a, and generate $O_2$ or any other oxidizing species like chlorine, iodine etc., but no $H^+$ ions are formed. Thus, the second electrode 110b does not produce an acidic environment around itself, and the alkaline zone produced by the first electrode 110a can spread the entire distance, or substantially all of the distance, between the electrodes 110, thereby providing a wide zone for electrolysis of the hair.

During use, a portion of the electrolyte 150 and a section of hair can be disposed between the first electrode 110a and the second electrode 110b. The section of hair can be placed in contact with the electrolyte 150 before, concurrently with, or after arranging said section of hair between the first electrode 110a and the second electrode 110b. The section of hair can be disposed between the first electrode 110a and the second electrode 110b such that when the electrodes are energized, the section of hair is disposed in, or at least contacts, the electrolysis zone. To style the hair, the first electrode 110a and the second electrode 110b can be moved relative to the section of hair disposed therebetween, along a substantially longitudinal axis thereof, such that the section of hair gradually advances out from between the electrodes 110 and an adjacent section of hair is introduced between the electrodes 110. By moving the section of hair through the electrolysis zone as described above, a change in style is imparted to the hair. Depending upon the embodiment, the change in style can comprise a transition from wavy to straight, a transition from straight to wavy, coloring, moisturizing, and/or thickening.

In some embodiments, the electrolyte can be formulated to contain any organic polymer molecules, for example, polyvinyl alcohol, polyethylene glycol, starch, dextran, sulfate, polypyrrolidone, Ficoll, any proteins, DNA, etc. In some embodiments, a non-aqueous salt solution can be used. For example, any one of the salts mentioned herein, or any other suitable salt can be dissolved in an organic solvent, for example, ethanol, methanol, acetone, isopropanol, tetrahydrofuran, dimethyl sulfoxide, or any other suitable organic solvent to form a non-aqueous salt solution. In such embodiments, the non-aqueous salt does not conduct electricity but when the non-aqueous salt solution contacts hair which has been moisturized with an aqueous moisturizer, the salt in the non-aqueous salt solution can dissolve in the moisturizer encapsulating the hair to form an aqueous electrolyte in situ. This aqueous electrolyte can subsequently be electrolyzed by the electrodes 110 for styling the hair. These components may have specific roles or general roles like altering the viscosity, conductivity and surface tension of the electrolyte.

In some embodiments, the electrolyte can include metallic, graphite, or any other conductive particles of varying dimension that improve conductivity and reduce the electrical resistance of the electrolyte solution. In some embodiments, the electrolyte can include acidic, basic or neutral buffer salts to modulate/fine tune the effect of electrolysis on the hair. In some embodiments, any kind of solution, an electrolyte or a powder of conducting material can be applied, for example, sprayed on or dusted, on the hair before using the hair styling device 100, to reduce the electrical resistance of the hair as well as to alter the moisture level in the hair. In some embodiments, the electrolyte can include additives, for example, a sulfhydryl group, such that the additives can be incorporated into the hair of the user U via oxidation to a disulfide bond by the electrolytic action of the hair styling device 100. For example, the electrolyte can include nanoparticles (e.g., fluorescent nanoparticles), dyes (e.g., one or more pigments), moisturizing polymers (e.g., polyvinyl alcohol with $OH^-$ groups), thickeners (e.g., polymer conjugated microparticles), frizz control agents (e.g., oils), glossiness agents (e.g., polyvinyl conjugated fatty acids), deodorants (e.g., polymer with multiple COOH groups), hair molding agents (e.g., castor oil and other long chain fatty acids), fragrance, or any combination thereof. In some embodiments, sodium chloride can be included as the salt in the electrolyte, such that chlorine is produced at the anode which can be used to bleach the hair. In some embodiments, only a portion of the electrodes 110 can be polarized to perform electrolysis such that the hair styling device 100 can be used for highlighting. In some embodiments, the hair styling device 100 can include a plurality of electrolyte reservoirs (or "containers") such that each of the plurality of reservoirs includes a different electrolyte formulated for a particular hair styling operation, as described herein.

In some embodiments, the electrolyte 150 can include a cross-linking compound formulated to allow cross-linking of free amine groups on the protein (i.e., keratin) molecules of the hair. Such cross-linking compounds can include, for example, phenols, enols, a compound that includes a benzene ring, a combination thereof, or any other compound configured to allow cross-linking of free amine groups on the hair. Any of the cross-linking compounds described herein can be formulated to transform into a cross-linking agent that includes multiple ketone groups when exposed to a highly alkaline pH, for example, a highly alkaline pH produced between the negatively biased first electrode 110a and the grounded second electrode 110b. The transformation of the cross-linking compound to the cross-linking agent that includes multiple ketone groups can make the cross-linking compound capable of cross-linking free amine groups on the protein (i.e., keratin) molecules, thus functioning as an active cross-linking agent produced from a relatively inert molecule. Inclusion of such cross-linking compounds can therefore, enable dynamic production of cross-linking agents in the electrolyte 150 during a hair styling operation. The cross-linking compounds can be included in the electrolyte formulation in different concentrations to achieve chemical modifications to the hair. In some embodiments, substrate multi-amine and/or multifunctional organic molecules can also be included in the electrolyte 150 formulation, for example, to provide a substrate for build-up of a cross-linked molecular matrix within the hair. The cross-linked molecular matrix can serve to style the hair (e.g., straighten hair or add curls to hair), or change its properties such as, for example, control frizz, alter glossiness, deodorize, augment the moldability, add fragrance, bleach, or highlight hair, or perform any other hair styling operation described herein.

In some embodiments, an electrolyte 150 formulation can include water, soluble salts, ascorbic acid (vitamin C), a surfactant, a lubricant, glycerol, and an acidic pH neutralizing salt. Each component of the electrolyte 150 formulation can have a specific function as described herein. The electrolyte 150 can also include water which can serve as the overall carrier of all the components of the electrolyte. Furthermore, water can also serve to generate the $OH^-$ and/or $H^+$ ions that produce the alkaline or acidic electrolysis zone, respectively between the first electrode 110a and the second electrode 110b.

The soluble salts can include sodium chloride, sodium iodide, sodium acetate, sodium citrate, or any other salt which can substantially ionize in water. Since water has poor electronic conductivity, the soluble salts can ionize in the water to produce ions that can raise the conductivity of the water and enables a higher current through the electrolyte 150. For example, the electrolyte 150 can include sodium iodide which can serve as an oxidizer. The sodium iodide can get oxidized at a ground electrode (e.g., the second electrode 110b) to form $I_2$ molecules which can combine with $I^-$ ions to form $I_3^-$ ionic complex which is readily soluble in water. The $I_3^-$ ionic complex can also penetrate deep into hair matrix and perform oxidation of the hair and/or any other compound included in the electrolyte 150.

The ascorbic acid can serve as a redox carrier molecule which is capable of being reduced or oxidized in a corresponding environment. The ascorbic acid is also capable of penetrating deep into the hair such that the redox environment can be carried deep into the hair. For example, the reducing or oxidizing reactions at the electrodes 110 produce gas molecules (e.g., hydrogen, oxygen, chlorine, etc.). Such gases generally have low solubility in water at atmospheric temperature and pressure and therefore do not penetrate deep into the hair. Hence, the reduction or oxidation environment produced by such gases only acts on the surface of the hair. Without being bound by any particular theory, the ascorbic acid can readily dissolve in the water and can be reduced or oxidized to carry the corresponding environment deep into the hair. In the reduced state, the ascorbic acid can reduce the disulfide bonds in the hair to sulfhydryl groups, and in the oxidized state, the ascorbic acid can oxidize a pair of sulfhydryl groups in the hair to form disulfide bonds. For example, as shown in equation (1) below, L-ascorbic acid can be oxidized to dehydroascorbic acid. Both of these are highly soluble in water, and can therefore effectively penetrate deep into the hair.

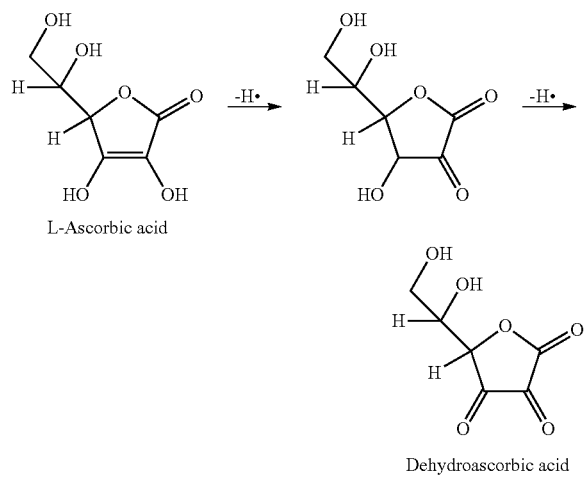

L-Ascorbic acid

Dehydroascorbic acid

In some embodiments, the electrolyte can be formulated to provide an acidic pH, for example, to enhance the acidic zone or facilitate the production of an acidic pH zone produced between a first positively charged electrode and a second electrode maintained at zero volts. In some embodiments, the electrolyte can be formulated to neutralize hair exposed to an alkaline zone, for example, to reform broken disulfide, ionic, or hydrogen bonds of the hair. Embodiments described herein can be used to straighten, curl, attach nanoparticles to, color, moisturize, thicken, control frizz, alter glossiness, deodorize, augment the moldability, add fragrance to, bleach, or highlight hair.

In some embodiments, the electrolyte 150 can be formulated to produce a relatively high acidic pH, for example, to enhance or facilitate the production of an acidic electrolysis zone generated between a positively charged electrode (e.g., the second electrode 110b) and a ground electrode (e.g., the first electrode 110a). For example, the electrolyte 150 can be formulated to produce a relatively low pH, for example a pH of less than about 6, about 4 to 5, or only about 1 or about 2. For example, metallic ions such as, for example, $Mg^{2+}$ or $Al^{3+}$ ions can combine with free $OH^-$ ions to neutralize the OFF ions and prevent their influence in raising the pH of the electrolyte 150. Neutral salts such as, for example, magnesium sulfate, aluminum sulfate, or any other suitable salt can readily dissolve in water or water based solutions to produce $Mg^{2+}$ or $Al^{3+}$ ions in the solution, thereby maintaining neutral pH. If an electrolyte 150 includes such salts, the salts can also neutralize the OFF ions. Thus the $H^+$ ions generated at a positively charged electrode (e.g., the second electrode 110b) can spread over the entire electrolysis zone between the electrodes 110 and thereby, produce a stronger and wider acidic zone between the electrodes 110. Such salts can also be provided in a hydrated form such as, for example, epsomite ($MgSO_4 \cdot 7H_2O$), aluminum sulfate hexadecahydrate ($Al_2(SO_4)_3 \cdot 16H_2O$), aluminum sulfate octadecahydrate ($Al_2(SO_4)_3 \cdot 18H_2O$), any other hydrated salt or combination thereof.

In some embodiments, the electrolyte can include nanoparticles or microparticles that can be incorporated into the hair during the electrolysis process. Microparticles can include, for example, cellulose microparticles, hydrogel microparticles, sol-gel microparticles, metallic microparticles, powdered natural hair microparticles, alginic acid microparticles, polyacrylic acid microparticles, cotton fiber microparticles, any other suitable microparticles or combination thereof. In some embodiments, the microparticles can be formed from a non-toxic material which is safe for human use. In some embodiments, the microparticles can be formed from a biodegradable material. The microparticles can be used to, for example, color the hair, add thickness to the hair, moisturize the hair, perform any other hair styling function or combination thereof. In some embodiments, the microparticles can be coupled to the hair by diffusion during the electrolysis process. In some embodiments, the microparticles can be formulated to include a linker, for example, avidin, streptavidin, 1-ethyl-3-(3-dimethylaminopropyl)carbodiimide (EDC), alkane thiol, alkene thiol, or any other suitable chemical or biochemical linker which can couple the microparticles to the hair or to nanoparticles (e.g., multifunctional polymer molecules) coated or incorporated in hair. In some embodiments, the microparticles can be formulated to include a charge, for example, a positive or a negative charge. In such embodiments, the microparticle can be incorporated into the hair by electrostatic coupling with oppositely charged nanoparticles (e.g., multifunctional polymer molecules) that were previously incorporated into the hair using electrolysis. In some embodiments, the microparticles can include sulfhydryl groups. In such embodiments, the microparticles can be coated or incorporated into the hair by forming disulfide bonds with multifunctional polymer molecules that were previously incorporated into hair using electrolysis and include sulfhydryl groups. In some embodiments, a plurality of microparticle layers can be coated on the hair to obtain the desired thickness. For example, alternate layers of positively and negatively charged microparticles can be coated on the hair using any process described herein until a desired thickness of the hair is achieved. Nanoparticles can be formulated to perform various styling functions such as, for example, color hair, make hair fluorescent, add thickness, and/or volume to hair.

In some embodiments, the electrolyte can include pigments or dyes formulated to color hair. In some embodiments, the electrolyte can include reducing or oxidizing agents. In some embodiments, the electrolyte can include colors, dyes, pigments, coloring agents, anti-frizz agents, oils, straighteners, moisturizers, shape memory materials or any other molecule used for styling hair. Any suitable dye or pigment can be used such as, for example, permanent hair color, demi-permanent hair color, semi-permanent hair color, temporary hair color, nigrosin, 1,3-diaminobenzene, phenols, naphthols (e.g., 3-aminophenol, 5-amino-2-methylphenol, 1-naphthol, etc.), 2,5-diaminotoluene coupled with 3-aminophenol, 2,5-diaminotoluene with 1-naphthol, resorcinol, 4-chlororesorcinol, benzodioxoles, any other suitable coloring agent, dye, pigment or combination thereof. In such embodiments, the coloring agents can be incorporated into the hair by electrolysis using the hair styling device 100 or any other hair styling device described herein. For example, an alkaline electrolysis zone can be produced in the electrolyte 150 between the electrodes 110 (e.g., the first electrode 110 biased at a negative voltage and the second electrode 110b maintained at a lower negative voltage.). When the hair is exposed to the alkaline electrolysis zone generated in the electrolyte 150, the sulfhydryl bonds can break and the dense keratin network can open up such that the dye, pigment, or otherwise coloring agent is able to penetrate the hair and is thereby incorporated into the hair. In some embodiments, the dye, pigment, or otherwise coloring agent can also include sulfhydryl groups such that the dye, pigment, or otherwise coloring agent can be coupled to the hair using disulfide bonds. In some embodiments, the electrolyte can include surfactants. In some embodiments, the electrolyte can include a lubricant. In some embodiment, the electrolyte can include a molecule, for example, glycerol formulated to prevent evaporation of the electrolyte.

In some embodiments, the electrolyte can include one or more additives for moisturizing hair. For example, the additives can include polymers (e.g., polyethylene glycol or polyvinyl alcohol) or nanoparticles which include multiple hydroxyl groups, such that polymers can get incorporated into the hair to moisturize the hair. The conventional methods of moisturizing hair simply add moisturizers to the surface which can be removed on washing. As described herein, the moisturizers are covalently linked to the surface of the hair and therefore the moisturizing effect lasts longer than conventional methods.

In some embodiments, the electrolyte can include one or more additives for thickening of the hair. For example, the additives can be polymers (e.g., polyethylene glycol or polyvinyl alcohol polymer) or nanoparticles which include a plurality of surface functional groups. Once the polymers are incorporated in the hair as described herein, micro-particles that include complimentary functional groups (e.g., oppositely charged groups) on their surface can be added to the treated hair. The complimentary functional groups of the micro-particles will couple to the functional groups of the polymers incorporated in the hair, such that the micro-particles are incorporated into the hair, rapidly adding thickness to the hair. Furthermore, dyes or pigments can also be added to the particles to simultaneously achieve thickening and coloring of the hair. Such micro-particles can be stripped on demand, for example, using a stripping solution that includes a high concentration of oppositely charged ions.

In some embodiments, the electrolyte can include one or more additives for frizz control of the hair. For example, the additive can include polymers or nanoparticles as described herein that include oil molecules that are incorporated into the hair as described herein. This can produce a long lasting non-sticky oil layer on the hair surface which is resistant to drying thereby, preventing frizz, or by adding a molecule with carboxylic groups which repel the hair by means of creating an identical charge on the entire hair surface. Furthermore, the covalently incorporated oil layer can resist stripping by washing with soap, thereby providing long lasting frizz control.

In some embodiments, the electrolyte can include one or more additives for altering the glossiness of the hair. For example, the additive can include polymers or nanoparticles as described herein, which include a fatty acid incorporated with the polymer. The polymer can be incorporated into the hair with the hydrophilic side of the fatty acid on the surface of the hair. The glossiness is produced by reflection of light from the hydrophilic molecule coated surface of the hair.

In some embodiments, the electrolyte can include one or more additives for deodorizing the hair. For example, the additive can include polymers or nanoparticles as described herein, which include multiple COOH groups. When the COOH groups are incorporated into the hair, they produce an acidic environment around the hair which prohibits bacterial growth. Moreover the COOH groups can also donate their $H^+$ ions to the volatile amines and keep them coupled to the surface prohibiting diffusion of odor producing molecules.

In some embodiments, the electrolyte can include one or more additives for augmenting the moldability of the hair. For example, the additive can include polymers or nanoparticles as described herein, which include a long saturated fatty acid (e.g., saturated castor oil). The hydrophobic long saturated fatty acid molecules can stick together by hydrophobic interactions and make it easier to adhere hair fibers together to produce various shaped hair bundles, for example, spiky styling of hair.

In some embodiments, the electrolyte can include a fragrance. The electrolysis process opens up and closes the hair protein matrix by breaking the disulfide bonds. Hence a fragrance molecule included in the electrolyte can diffuse deep into the hair protein matrix and thereby provide long lasting fragrance diffusing out from the hair.

In some embodiments, the hair styling device can be used for bleaching of the hair. If an oxidizing molecule, for example, hydrogen peroxide, sodium percarbonate, sodium perborate, or any other oxidizing molecule is included in the electrolyte, the electrolysis process can be shifted towards a more oxidizing process which can be exploited for bleaching of the hair. In addition, if the salt included in the electrolyte is sodium chloride, or any other chlorine based salt, the electrolysis process induces synthesis of chlorine at the anode. Therefore, by adjusting the amount of salt in the electrolyte, the quantity of chlorine generated at the anode can be controlled and can be used for bleaching the hair. In some embodiments, the electrolysis process can also be used for bleaching of the colors added previously to the surface of the hair.

The electrolyte 150 can be housed in a suitable reservoir or container (not shown), for example configured to fluidly communicate electrolyte to the electrodes 110. In some embodiments, an electrolyte container can include a channel in fluidic communication with a temporary reservoir for holding the electrolyte. The electrolyte container can be disposed such that the electrolyte is communicated the temporary reservoir through gravity and surface tension such that no active pumping is required. In some embodiments, a pump, for example, a micropump, a peristaltic pump, a syringe pump, or any other suitable pump can be used to facilitate communication of the electrolyte from the electrolyte container to the electrodes 110. In some embodiments, the electrolyte container can include clamps configured to latch onto corresponding grooves on the frame, such that the electrolyte container can be removably disposed on the frame. The electrolyte container can also include a lid. The electrolyte container can be made from any suitable insulating and light weight material, for example, plastics, polycarbonate, Teflon®, polymers, any other suitable material or combination thereof. In some embodiments, the electrolyte container can include a sponge. In some embodiments, the electrolyte container can include a cavity defined in a housing (not shown) of the hair styling device 100. In some embodiments, a pumping mechanism, for example, an air chamber or a pump, can be coupled to the electrolyte container and configured to pump electrolyte into the electrolyte container.

The control module 170 can be configured to control the operation of the electrodes, for example, the current flowing between the electrodes, the polarity of the electrodes, and/or the potential difference applied across the electrodes. The control module can include a knob, at least a portion of which can be disposed in a cavity defined by a cover portion. The knob can be configured to allow a user to turn the hair styling device ON or OFF, adjust the polarity of the electrodes (e.g., positive, negative, or zero), and or adjust the magnitude of the biasing voltage, for example, to adjust the intensity of the electrolysis.

Figure 2:
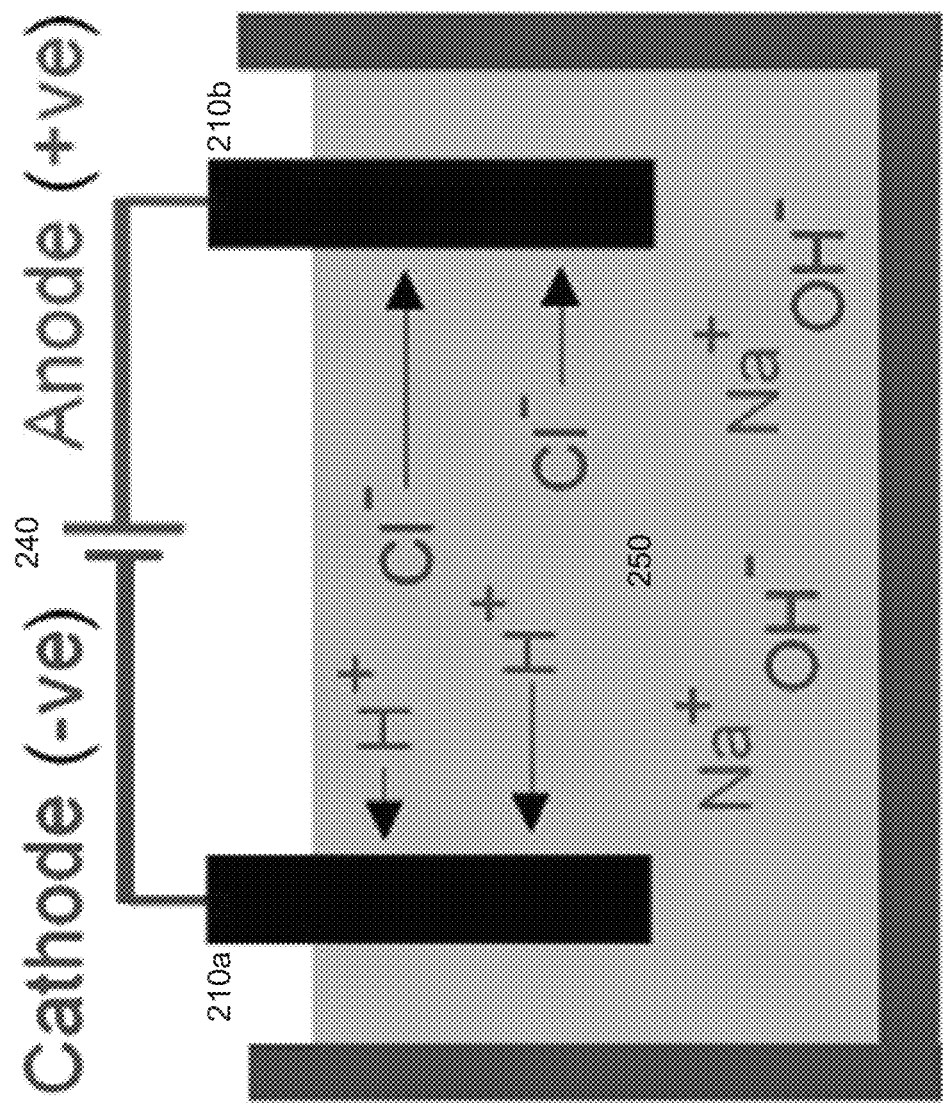
FIG. 2 shows a schematic view of an electrolysis apparatus.

Turning now to FIG. 2, a schematic view of a basic electrolysis cell is provided, depicting electrolysis of sodium chloride (NaCl). A cathode 210*a* and an anode 210*b* are connected to a voltage source 240. When electrolysis is performed using a dilute aqueous sodium chloride electrolyte, H+ and Na+ ions are attracted to the cathode (e.g., platinum), H+ ions gain electrons from the cathode 210a to form hydrogen gas. The hydrogen ions can accept electrons more readily than the sodium ions. As a result, H+ ions are discharged as hydrogen gas, which bubbles off, and Na+ ions remain in solution. (2H+(aq)+2 e-→H$_2$ (g)). Hydroxide (OH—) and chlorine (Cl-) are attracted to the anode 210b (e.g., platinum). OH— ions give up electrons to the anode to form water and hydrogen gas, and Cl- ions remain in solution. (4OH-(aq)→2H$_2$O(l)+O$_2$ (g)+4 e-). Thus, the overall reaction is 2H$_2$O(l)→2H$_2$ (g)+O$_2$ (g), and the concentration of NaCl increases in the electrolyte 250. On the other hand, when electrolysis is performed using a concentrated aqueous sodium chloride electrolyte, Cl- ions are more numerous than OH— ions at the anode. Consequently, Cl- ions are discharged as chlorine gas, which bubbles off, and the OH— ions remain in solution. (2Cl-(aq)→Cl$_2$ (g)+2 e-). One volume of hydrogen gas is given off at the cathode 210a and one volume of chlorine gas is produce at the anode 210b. The resulting solution becomes alkaline because there are more OH— than H+ ions left in the solution.

Figure 3:
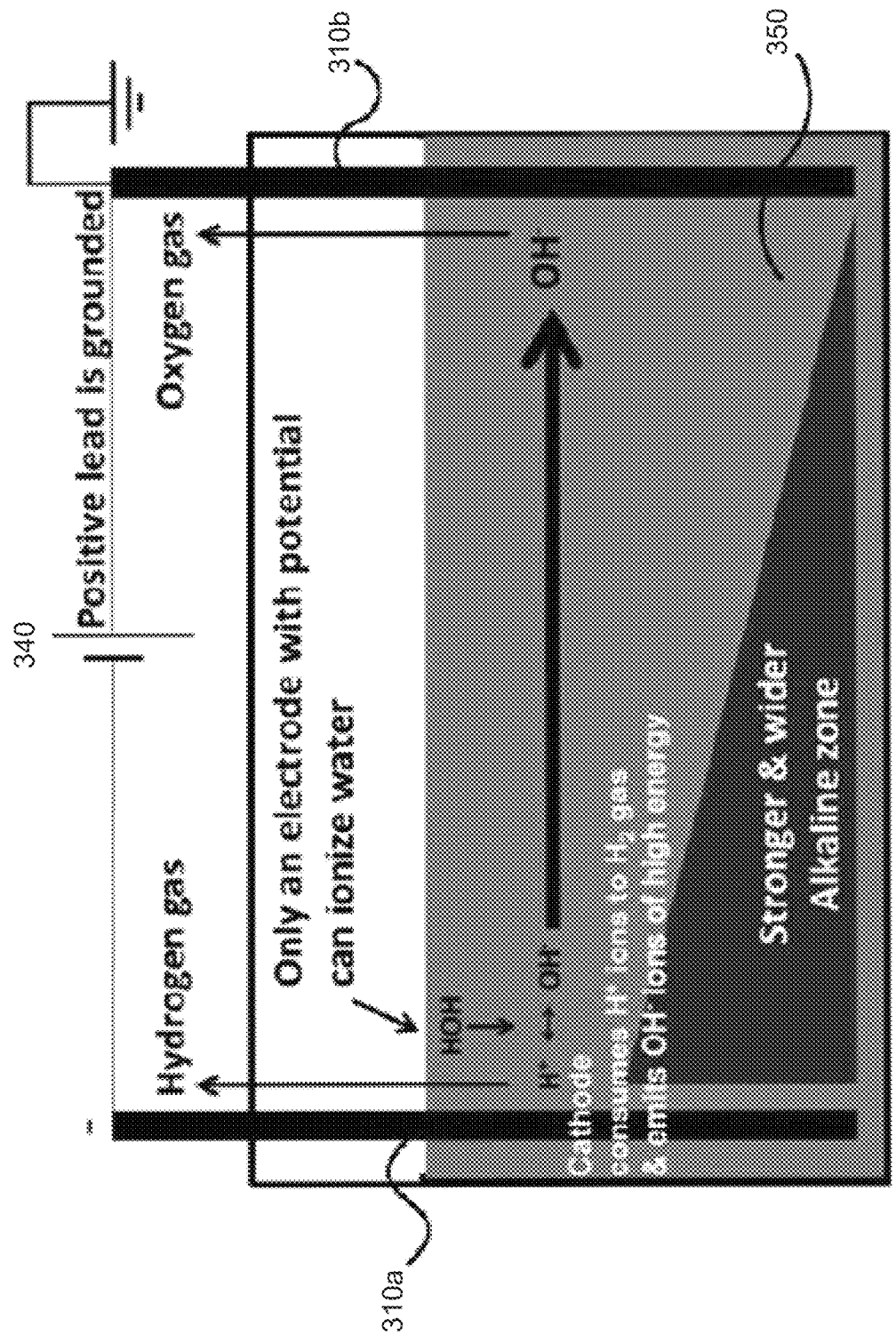
FIG. 3 shows a first electrode biased at a negative potential and a second electrode that is grounded, such that an alkaline electrolysis zone is produced in an electrolyte disposed between the first electrode and the second electrode.

FIG. 3 shows a first electrode 310a biased at a negative potential and a second electrode that is grounded, such that an alkaline electrolysis zone is produced in an electrolyte disposed between the first electrode and the second electrode. The first electrode 310a and the second electrode 310b can be in contact with the electrolyte 350, for example, an aqueous electrolyte. The first electrode 310a can be biased at a negative voltage, for example, -24 V and the second electrode 310b can also have a negative voltage (for example, -12 V) or can be configured to have a voltage near zero volts. The negative potential on the first electrode 310a can ionize the aqueous electrolyte 350 to generate H$^+$ and OH$^-$ ions. The negative potential of the first electrode can reduce the H$^+$ ions to hydrogen gas which can be released out of the electrolyte 350 as hydrogen bubbles. The negative potential on the first electrode 310a simultaneously repels the OFF ions towards the second electrode 310b. Since the second electrode 310b is at a negative or near zero volts (i.e., is connected to ground), it does not ionize the electrolyte 350. Therefore, there are no H$^+$ ions emitted from the second electrode 310 and the electrolyte 350 does not include any free H$^+$ ions which can neutralize the OFF ions. Thus, the OFF ions are free to travel towards the second electrode 310b and remain in high concentration across the entire distance between the first electrode and the second electrode. In this manner, a stronger and wider alkaline zone spanning from the first electrode 310a to the second electrode 310b is produced. The second electrode 310b consumes the OH$^-$ produced at the negatively charged first electrode 310a and generates O$_2$ or any other oxidizing species like chlorine, iodine etc. but no H$^+$ ions are formed. Thus, the second electrode 310b does not produce an acidic environment around itself, and the alkaline zone produced by the first electrode 310a can spread closer to the second electrode 310b. Furthermore, the consumption of the OH$^-$ ions at the second electrode 310b by the oxidizing species can also urge the pH towards neutral pH as well as generate an oxidizing environment proximate to the second electrode 310b.

In some embodiments, the electrodes 310 can be biased and/or configured to have the same polarity (i.e., both positive-valued or both negative-valued) to produce a wide alkaline or acidic electrolysis zone between the electrodes. For example, in some embodiments, a wide alkaline electrolysis zone can be produced by biasing the first electrode 310a at a first negative voltage such that the second electrode 310b has a second negative voltage. The first negative voltage can be substantially higher than the second negative voltage (e.g., -24 V at the first electrode and -12 V at the second electrode), such that a wide alkaline electrolysis zone that spans the entire distance between the first electrode 310a and the second electrode 310b is produced. Similarly, in some embodiments, a wide acidic electrolysis zone can be produced by biasing the second electrode 310b at a first positive voltage and connecting the first electrode 310a to ground. The first positive voltage can be substantially higher than any positive voltage at electrode 310a such that a wide acidic electrolysis zone that spans most of the distance between the first electrode and the second electrode is produced.

Figure 4:
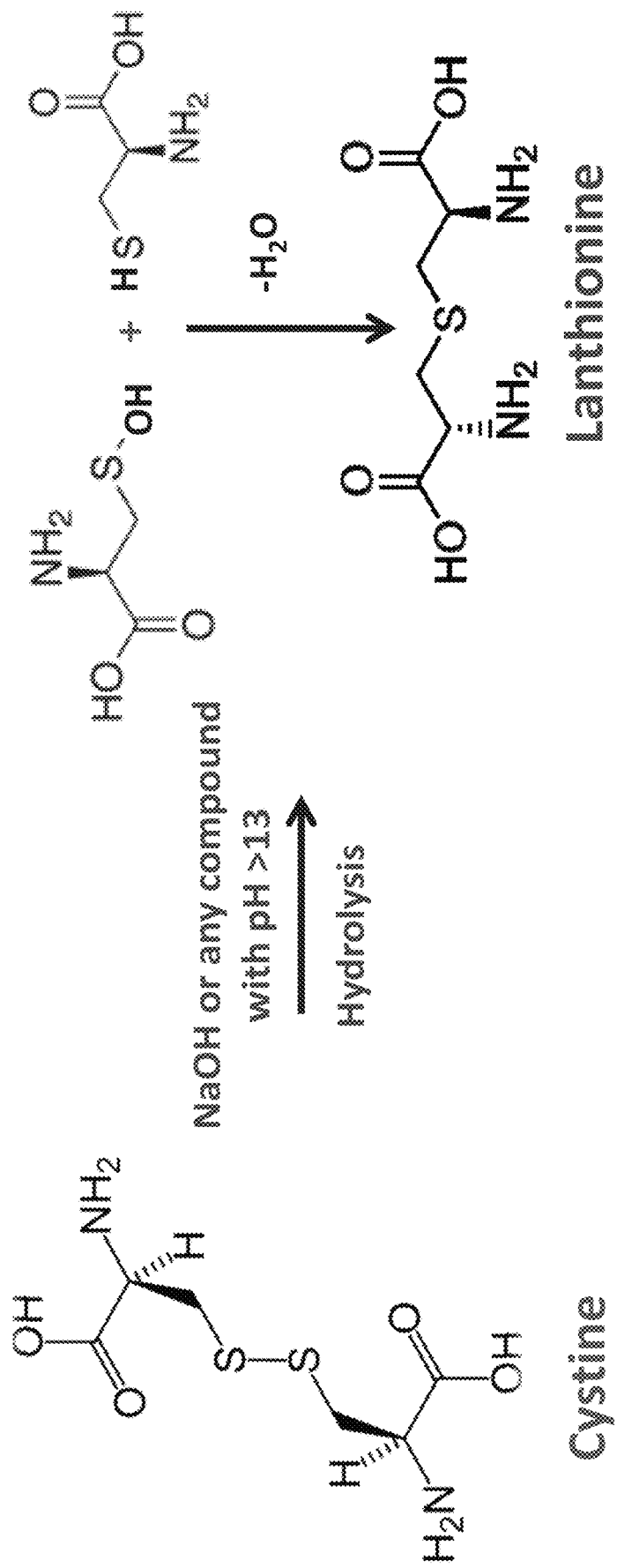
FIG. 4 shows a lanthionization process using hydroxide, according to an embodiment.

FIG. 4 shows a lanthionization process using hydroxide, according to an embodiment. A cystine molecule is shown on the left, comprising two cysteine residues linked together by disulfide bonds. A lanthionine is produced upon exposure of the cystine to sodium hydroxide (NaOH) or any compound with a pH of greater than 13 ("hydrolysis"), by breaking (i.e., "cleaving") the disulphide link (having a high bond energy of 200-300 kJ/mol), or the "S—S bonds."

Figure 5:
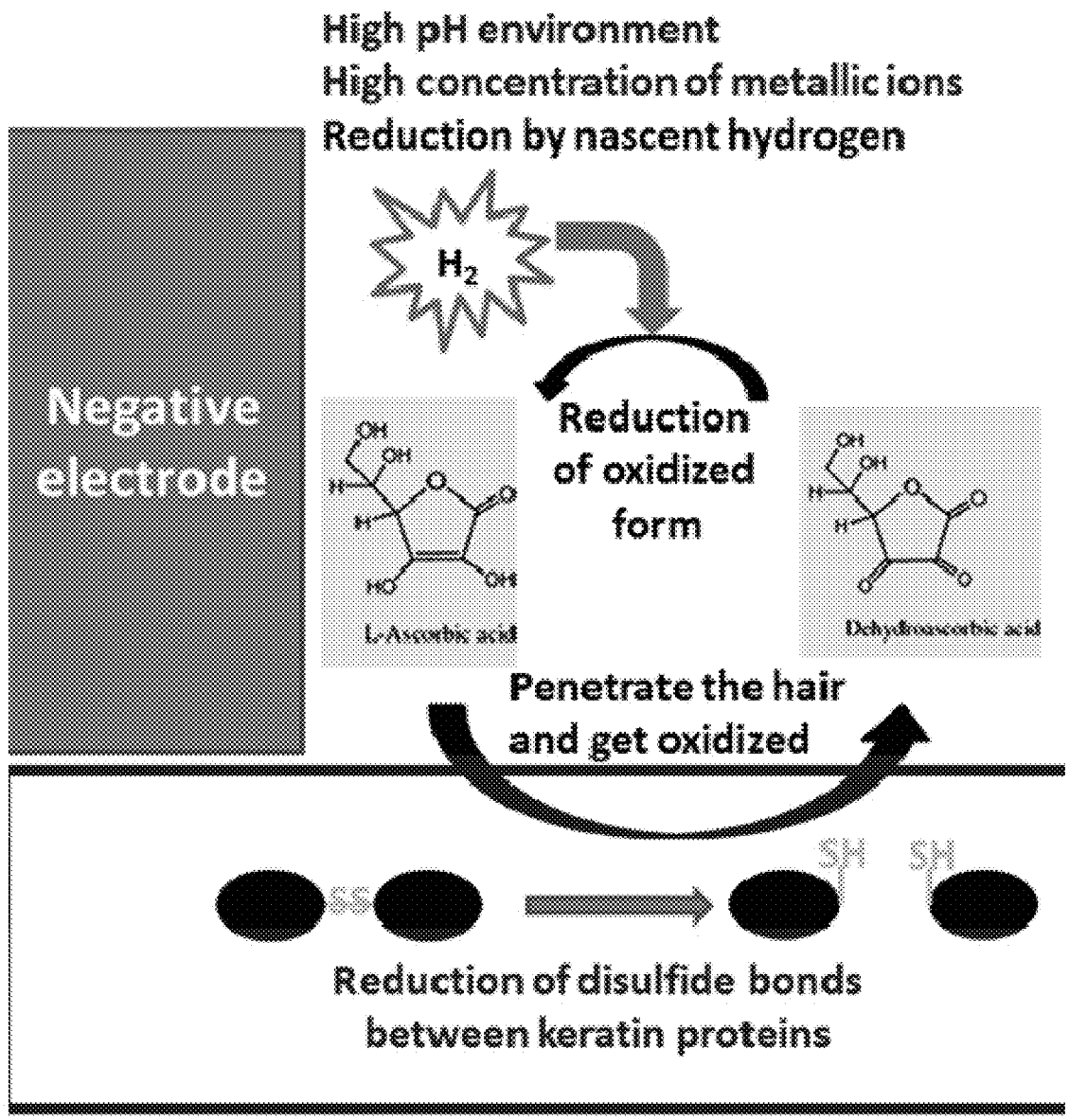
FIG. 5 shows a redox pathway of L-ascorbic acid included in an electrolyte at a negatively charged electrode in the presence of hair.

FIG. 5 shows the redox reaction of L-ascorbic acid included in an electrolyte at a negatively charged electrode (e.g., a "first" electrode). The alkaline environment rich in metallic ions produced by the negatively charged electrode converts the ascorbic acid into a powerful reducing agent. Due to the high solubility of ascorbic acid in water, it can penetrate deep into the hair matrix. Inside the hair matrix, the ascorbic acid can reduce the disulfide bonds of the hair to sulfhydryl groups and be oxidized to dehydroascorbic acid. Dehydroascorbic acid can diffuse back into the electrolyte and be reduced back to ascorbic acid by the nascent hydrogen produced near the negatively charge electrode. This forms a cycle which regenerates the ascorbic acid and sustains the process of reduction of the disulfide bonds. The reducing environment near the negatively charged electrode keeps the reduced form of ascorbic acid at a higher concentration than the oxidized form (i.e., dehydroascorbic acid). In this manner, reduction of disulfide bonds can be favored at the negatively charged electrode.

FIG. 6A shows the random distribution of disulfide, ionic, and hydrogen bonds in an untreated portion of hair. FIG. 6B shows the distribution of the bonds included in the portion of the hair after exposure to an alkaline electrolysis zone, for example, having a pH of about 13 or 14, produced by a cathode (i.e., a negatively charged electrode). The reducing environment of the alkaline electrolysis zone can open the cuticle of the hair and break a substantial portion of the disulfide bonds and, when coupled with mechanical stretching (e.g., straightening) of the portion of the hair by the electrodes, can achieve straightening of the hair. Many of the disulfide bonds can undergo lanthionization as well. A small portion of the disulfide bonds can however, persist. FIG. 6C shows distribution of the bonds in the portion of the hair on neutralization of the high pH. FIG. 7 shows a structure of a multifunctional polymer molecule that can be included in the electrolyte. The multifunctional polymer molecule can be formulated to include a carbon backbone which includes a plurality of sulfhydryl and amine groups coupled thereto. Furthermore, the multifunctional polymer molecule can also include biotin attached to the carbon backbone. The biotin can be used, for example, to couple any other nanoparticle, a microparticle, a pigment, a chemical molecule, a biochemical molecule, or any other agent using an avidin-biotin coupling mechanism, as is commonly known in the arts.

While shown as including biotin, the multifunctional polymer molecule can be formulated to include any other chemical or biochemical linker, such as, for example, thiols.

Turning now to FIG. 8 when the hair is exposed to the alkaline and reducing zone of a first electrode 410a and a second electrode 410b, at least a portion of the disulfide bonds present on the surface of the hair can be reduced to sulfhydryl groups. The electrolyte can also include additives that can include sulfhydryl groups conjugated with the additives (e.g., synthetic molecules). These additives can be incorporated into the surface of the hair or within the hair matrix via disulfide bonds when the oxidizing zone of the positive second electrode oxidizes the sulfhydryl groups to disulfide groups. In this manner, any additive can be incorporated into the hair by including a sulfhydryl group or ionic group or groups favoring hydrogen bonds on the hair in an additive.

FIG. 9 is a schematic illustration of a side view of a hair styling device 500 according to some embodiments. A first elongate member 502 and a second elongate member 504, comprising a first electrode 520a and a second electrode 520b, respectively, are movably coupled to one another at an apex or "hinge" point 506 (e.g., in a "flat-iron" type configuration). The first and second elongate members (502, 504) are movable relative to one another such that as an angle defined between them is increased, the distance between the first and second electrodes increases, and as the angle defined between them is decreased, the first and second electrodes (520a, 520b) are brought closer together, for example to clamp down onto a section of hair received therebetween.

FIG. 10 shows a schematic illustration of a DC voltage module 540 circuit for use with the hair styling device 500 of FIG. 9, according to some embodiments. An alternating current ("AC") source, for example a wall outlet or other external power supply, connects with an AC-to-DC adapter/converter having negative and positive DC output terminals (520a and 520b, respectively). The AC-to-DC adapter/converter converts the incoming AC voltage into a DC potential at the output terminals 520a and 520 (for example using a step-down transformer and a signal rectifying circuit), and may be selected to output a specified voltage level (e.g., +/−6 V, +/−12 V, +/−24 V or +/−50 V). A switch "S" is disposed between the negative DC output terminal and a first terminal of a circuit output (e.g., representing the first electrode), allowing a user to turn the circuit on and off. As shown, the positive DC output terminal and the second electrode are connected to electrical ground, here shown as a common ground. The second electrode is electrically connected to the ground via a resistor "R1" and through a fuse "F." As such, when the fuse F is closed, the second terminal of the circuit output is electrically coupled to ground via R1. As a result of the resistance between the second terminal of the circuit output and the ground, the voltage at the second terminal has the same polarity as that at the first terminal, but a smaller absolute value. In some embodiments, the resistance value of R1 is about 2 ohms. The value of the resistance R1 is selected to provide the desired potential difference and current between the first and second electrode. In some embodiments, the resistance value of R1 is selected such that a current between the first and the second electrode is about 5 A or about 8 A. In some embodiments, the resistance value of R1 is selected such that a current between the first and the second electrode is in a range of 5-6 A or 5-10 A. In some embodiments, the resistance value of R1 is selected such that the potential difference between the two electrodes is in the range of about 5 to about 20 volts, or is at least about 5 volts, or is at least about 10 volts, or is at least about 12 volts.

Another resistor, "R2," is disposed in parallel with the circuit output. This parallel resistor, R2, provides a second current path between the output terminals, for example providing a bypass path in the event of a power surge (e.g., when the first and second electrodes 510a and 510b of the styling device 500 are separated after use). In some embodiments, the resistance value of R2 is about 48 ohms.

The configuration of the DC voltage module and resistor R1 can be chosen based on an expected resistance between the first and second electrodes during use, for example as determined by the electrolyte chosen, the spacing between the first and second electrodes during use, and/or the type of hair that will be styled (and thus disposed between the first and second electrodes). In some embodiments, the resistance between the first and second electrodes during use is about 2 ohms. The circuit of FIG. 10 (i.e., the DC voltage module 540) is configured (e.g., through the selection of the AC-to-DC adapter/converter output voltage and/or the resistance (s)) to supply a current between the first and second electrodes, during use, of at least 1.5 amperes ("A") or about 1.5 amperes. In some embodiments, current above 12 A is avoided because it can be damaging to the hair. Acceptable ranges of current include approximately 5-6 A of current, about 2 A to about 12 A, about 2 A to about 10 A, about 5 A to about 8 A, about 5 A to about 7 A, about 4.5 A to about 6.5 A, and about 5.5 A to about 6.5 A. In some embodiments, the current is about 8 A. In some instances, the current flow between the first electrode and the second electrode can depend on at least one of: (i) the resistivity of the electrolyte; (ii) the voltage difference between the electrodes; (iii) the size of the electrodes; (iv) whether or note the electrodes are padded; and (v) the distance between the electrodes.

In some instances, heat is generated during use of the hair styling device, e.g., by virtue of the current flowing through the device (a product of the current, squared, and the resistance—"$I^2R$" heating). As the temperature increases, the rate of the chemical reaction can also increase and performance of the styling device can be enhanced. In some instances, the temperature of the electrodes during use is between about 50 degrees C. and 70 degrees C. In other embodiments, the DC output terminals may instead be terminals of a battery cell, thus precluding the need for an AC-to-DC adapter/converter.

FIG. 11 is a schematic illustration of a side view of the first electrode 520a and the second electrode 520b of a hair styling device 500 according to some embodiments, having no electrolyte disposed therebetween.

FIG. 12 is a schematic illustration of a side view of the first electrode and the second electrode of the hair styling device of FIG. 11, having an electrolyte and a segment of hair "H" disposed therebetween, and a current "I" flowing therebetween, according to some embodiments. A first alkaline/reducing electrolysis zone 552 is produced in the vicinity of the first electrode 520a, and extends therefrom in the direction of the second electrode 520b. The segment of hair H is disposed within the alkaline electrolysis zone 552. In come embodiments, an absorbent pad disposed on the second electrode 510b absorbs high-pH electrolyte (the high pH generated by the first electrode 110a), thereby causing it to be distributed on both sides of the hair H. A second electrolysis zone, 554, is produced in the vicinity of the second electrode, 520b, and extends therefrom in the direction of the first electrode 520a. The first electrode 520a is biased at a negative potential whose absolute value is greater than the absolute value of a e potential of the second electrode 520b.

In some embodiments, an electrolyte-containing pad (not shown) is disposed on the second electrode 520b, such that the entirety of the second electrolysis zone 554 is disposed within the pad. In such embodiments, the electrolyte-containing pad can be dimensionally stable such that it does not swell significantly upon introduction of the electrolytic solution. The pad can also be chemically inert such that it does not degrade in the presence of the highly alkaline or acidic conditions created during electrolysis. The pad can be substantially uniform in dimension. FIG. 13 is a sectional view of the region marked "S" in FIG. 12, showing exemplary relative locations of the first electrode 520a, the second electrode 520b, the alkaline zones 552 and 554, and the segment of hair H.

Electrolysis Zones Generated by Various Configurations of Electrode Polarity

FIG. 14 shows acidic and alkaline zoned produced between a first electrode labeled 1 (also referred to as "electrode 1") and a second electrode labeled 2 (also referred to as "electrode 2") at various voltages and polarities. The electrodes 1 and 2 included flat plates which were about 100 mm long, about 25 mm wide and about 3 mm thick, and formed from stainless steel 304. An electrolyte including sodium sulfate in water at a concentration of 5 g/100 ml mixed with anthocyanin based pH indicator solution was disposed between the electrodes 1 and 2 such that the electrolyte was in contact with both the electrodes. The electrode 1 and 2 were coupled to the variable voltage outputs of an electric circuit that included a potentiometer, (e.g., a voltage divider, a rheostat, and/or a variable resistance). The electrical circuit was powered by a power supply of direct current of about 50 V and 7.5 A capacity. The power supply was a either a full wave rectifier or an AC to DC converter. The midpoint of the electrical circuit was grounded. The outputs from the electrical circuit having different potentials were applied to the electrodes by pressing two male plug terminals on the surface of the stainless steel electrodes. The change in pH was indicated by the color change of the anthocyanin based pH indicator dissolved in the electrolyte. This pH indicator gives violet color for neutral pH, green color for pH of 13, red color for pH of 3 and dark violet/dull red color for low acidic pH close to neutral pH.

FIG. 14 panel A-D show the electrolysis zone produced between the electrodes in a first configuration (also referred to as "the conventional configuration") in which electrode 1 was biased at a negative voltage and electrode 2 was biased at a positive voltage such that potential difference between the electrodes was about 20 V. At 0 seconds after biasing, the alkaline and acidic zones are barely visible (panel A). At about 10 seconds (panel B), a highly alkaline zone is produced proximate to electrode 1 and a highly acidic zone is produced proximate to electrode 2. The highly alkaline and highly acidic zones grow larger at about 20 seconds (panel C) until at about 30 seconds (panel D) a highly alkaline zone is present proximate to electrode 1 and a highly acidic zone is produced proximate to electrode 2, which are separated by a wide neutral pH zone.

FIG. 14 panels E-H show the electrolysis zone produced between the electrodes in a second configuration (also referred to as the "MES1 configuration") in which electrode 1 was biased at a negative voltage (−20 V) and electrode 2 was grounded (i.e., at or near 0 volts) such that potential difference between the electrodes was about 20 V. At 0 seconds after biasing, the alkaline and acidic zones are barely visible (panel E). At about 10 seconds (panel F), a highly alkaline zone is produced proximate to electrode 1 and a low acidic zone is produced proximate to electrode 2. The highly alkaline and low acidic zones grow larger at about 20 seconds (panel G) until at about 30 seconds (panel H) a highly alkaline zone is present proximate to electrode 1 and a low acidic zone is produced proximate to electrode 2, which are separated by a neutral pH zone.

FIG. 14 panels I-L show the electrolysis zone produced between the electrodes in a second configuration (also referred to as the "MES2 configuration") in which electrode 1 was biased at a first negative voltage (−5 V) and electrode 2 was at a second negative voltage (−25 V), such that the potential difference between the electrodes was about 20 V. At 0 seconds after biasing, the alkaline and acidic zones are barely visible (panel I). At about 10 seconds (panel J), a highly alkaline zone is produced proximate to electrode 1 and a low acidic zone is produced proximate to electrode 2. The highly alkaline and low acidic zones grow larger at about 20 seconds (panel K) until at about 30 seconds (panel L) a highly alkaline zone is present proximate to electrode 1 and a low acidic zone is produced proximate to electrode 2, which are separated by a neutral pH zone. The highly alkaline zone was substantially larger than the low acidic zone after 30 seconds of electrolysis. Furthermore, the alkaline zone produced by the electrode 1 in the MES2 configuration was substantially larger than the alkaline zones produced by the electrode 1 in conventional electrolysis configuration or the MES 1 configuration, clearly showing that a wider alkaline electrolysis zone is produced in the MES2 configuration.

FIG. 15 is a further side view of the hair styling device of FIG. 9, in a second, closed configuration and having a section of hair disposed and clamped therebetween. FIG. 16 is an end view of the hair styling device of FIG. 9, in the second configuration (i.e., of FIG. 15) and in use. The arrow indicates an exemplary direction of travel, in which the styling device slides across the received section of hair, thereby inducing a change, via electrolysis as described herein, in the style of the hair.

FIG. 17 shows a schematic illustration of a further DC voltage module 640 circuit, according to some embodiments. An alternating current ("AC") source, for example a wall outlet or other external power supply, connects with an AC-to-DC converter having negative and positive DC output terminals (620a and 620b, respectively). A switch "S" is disposed between the negative DC output terminal 620a and a first terminal of a circuit output (e.g., representing the first electrode). The positive DC output terminal 620b is connected to electrical ground. A second terminal of the circuit output (e.g., representing the second electrode) is also electrically coupled, via a resistor "R1," to electrical ground. Another resistor, "R2", is disposed in parallel with the circuit output.

FIG. 18 shows various configurations of biasing voltages and polarity that the control module can be used to generate on the electrodes. Here, "M" or "L" refers to biasing voltage configurations of the electrodes that do not include a ground electrode (e.g., the first electrode or the second electrode), and "$M_g$" refers to biasing voltage configurations of the electrodes that include a ground electrode. As shown in FIG. 18, a power supply, for example, a power supply included in the DC voltage module, as described herein, can be configured to provide a predetermined voltage, for example, a voltage of about 50 V to the control module. In a first configuration, the first electrode can be biased at a voltage M1 of about 25 V, and the second electrode can be biased at a voltage M4 of about −25 V (or vice versa). This is the configuration used in conventional electrochemical cells which produces an acidic electrolysis zone proximate to the anode, and an alkaline electrolysis zone proximate to the cathode, and a neutral zone at an intermediate distance between the electrodes.

In a second configuration, the first electrode can be biased at a voltage $M_g1$ of greater than about 0 V and up to about 50 V, and the second electrode can be biased at a voltage $M_g0$ which is ground (or vice versa). This generates a stronger and wider acidic zone which spans the entire distance between the first electrode and the second electrode.

In a third configuration, the first electrode can be biased at the voltage $M_g2$ of less than about 0 volts and up to about −50 V, and the second electrode can be biased at a voltage $M_g0$ which is ground (or vice versa). This generates a stronger and wider alkaline zone which spans the entire distance between the first electrode and the second electrode.

In a fourth configuration, the first electrode can be biased at the voltage M1 of greater than about 0 V and up to about 50 V, and the second electrode can be biased at a voltage M2 greater than about 0 V but less than M1 (or vice versa). Said another way, the first electrode is biased at the positive voltage M1 and the second electrode is biased at the positive voltage M2 which is substantially smaller than M1. In this manner, a stronger and wider acidic zone, which spans the entire distance between the first electrode and the second electrode can be generated.

In a fifth configuration, the first electrode can be biased at the voltage M4 of less than about 0 V and up to about −50 V, and the second electrode can be biased at a voltage M3 less than about 0 V but greater than M4. Said another way, the first electrode is biased at the negative voltage M4 and the second electrode is biased at the negative voltage M3 such that M4 is biased at a substantially larger negative voltage in magnitude than M3. In this manner, a stronger and wider alkaline zone, which spans the entire distance between the first electrode and the second electrode can be generated.

FIG. 19 is a hair styling device kit according to some embodiments. The kit can comprise the styling device, a holder for the styling device, a DC voltage module (optionally including a control module), at least one electrolyte formulation, and/or at least one neutralizing formulation.

FIG. 20 shows a hair styling device 700, having a first elongate member 702 and a second elongate member 704 and with a second electrode 710b visible, according to one implementation, in a first, open configuration. FIG. 21 is a partial view of the hair styling device of FIG. 20, also in the first, open (i.e., "unclamped") configuration. FIG. 22 is a partial view of the hair styling device of FIG. 20, in a second, closed (i.e., "clamped") configuration. In the closed configuration, the two elongate portions (702, 704) of the hair styling device 700 may be squeezed together (in some embodiments, "squeezing" hair disposed therebetween and/or a pad disposed therebetween). This squeezing motion brings the first electrode 710a and the second electrode 710b (e.g., including a pad 755, as shown in FIG. 22) into proximity with one another, thereby inducing the formation of the electrolysis zone described above. Furthermore, the squeezing motion may result in a dynamic variation of the current as the user presses the flat electrodes together.

FIG. 23A is a partial view of the hair styling device of FIG. 20, also in the second, closed configuration and indicating the positioning of the cathode and the anode, according to some embodiments. FIG. 23B is a partial view of the hair styling device of FIG. 20, in the first, open configuration and having a portion of electrolyte formulation disposed thereon. A pH strip is shown, indicating a high pH (i.e., "alkaline") content. FIG. 23 is a partial view of the hair styling device of FIG. 20, in the second, closed configuration, having electrolyte formulation and a segment of hair disposed therein, and during use. FIG. 25 is a further partial view of the hair styling device of FIG. 20, in the second configuration and in use. In FIG. 25, a section of straightened hair is shown in the top half of the figure (i.e., the direction of travel of the sliding hair styling device is downward).

Electrolytic Straightening of Hair

FIG. 26 shows results of various straightening treatments used to straighten samples of naturally wavy hair, according to some embodiments. Each hair sample included a bundle of naturally wavy Indian hair having substantially the same texture and physical properties. Furthermore, the electrolyte and biasing voltage used for straightening the samples using electrolysis was substantially the same for all samples. Sample 1 was a control sample. Sample 2 was straightened by treating sample 2 with an alkaline electrolysis zone produced in an electrolyte between a cathode and a ground. Sample 3 was straightened by treating sample 3 with an alkaline electrolysis zone produced by a cathode and an acidic electrolysis zone produced by an anode. Sample 4 was straightened by treating sample 4 with an alkaline electrolysis zone produced by a cathode and oxidizing with a 3% hydrogen peroxide solution.

Sample 1 shows a control bundle of hair that was not subjected to any straightening treatment. Sample 2 shows a bundle of hair that was treated with an alkaline electrolysis zone produced in an electrolyte in contact with the sample 2 hair using a cathode and a second electrode. Each electrode was masked with a piece of cloth having a thickness of about 400 microns on the cathode and about 5,000 microns on the grounded electrode so that the hair is exposed to a high pH zone near the cathode without being exposed to the surface of the electrodes. A total of 10 combing strokes were applied to sample 2. The sample 2 hair was washed and dried. As shown in FIG. 26, substantially all of the curls in the sample 2 bundle of hair are removed and the sample 2 is substantially straight.

Sample 3 shows a bundle of hair treated with an alkaline electrolysis zone produced by a cathode and an acidic electrolysis zone produced by an anode. The sample 3 was subjected to 5 strokes on the surface of the cathode and followed by 5 strokes on the surface of the anode such that the sample 3 was in direct contact with the bare electrode surface. The sample 3 hair was washed and dried. As shown in FIG. 26, the sample 3 had substantially less curls than the control sample 1 but includes substantially more curls as compared to the sample 2.

Sample 4 shows a bundle of hair that was treated with an alkaline electrolysis zone produced by an unmasked cathode. The hair was subjected to 10 combing strokes of the unmasked cathode. The sample 4 was then exposed to an oxidizing solution of 3% hydrogen peroxide for 30 minutes, washed and dried. As shown in FIG. 26, the sample 4 seems to have fewer curls than the sample 1, but substantially more curls than the sample 2 and sample 3 bundle of hair.

FIG. 27 shows various samples of bundles of naturally wavy hair straightened using a hair styling device according to an embodiment of the present disclosure, using an applied voltage at the cathode of −24 V, as compared with a control sample (the rightmost bundle), arranged according to the number of treatment strokes. FIG. 28A shows a bundle of unstraightened hair, FIG. 28B shows the hair straightened using the hair styling device of FIG. 1, with an applied voltage at the first electrode of −48 V, and FIG. 28C shows the bundle of straightened hair after drying.

Turning now to FIGS. 29-40, results of testing the hair styling device of the present disclosure are provided. Subjects were treated as described below, with sections of hair being (1) left untreated, (2) treated with a device of, and according to a method of, the present disclosure, with an applied voltage at the cathode of −24 V, (3) washed/dried, and/or (4) straightened with a regular "flat iron." These examples are only for illustrative purposes and are not intended to limit the scope of the present disclosure.

FIG. 29A shows a user's hair prior to treatment; FIG. 29B shows the user's hair immediately after treatment, with three regions indicated: (1) untreated (left ⅓ of the user's hair), (2) treated with the hair styling device of the disclosure (middle ⅓ of the user's hair), and (3) treated with a flat iron (right ⅓ of the user's hair); FIG. 29C shows the user's hair after one wash-and-dry cycle.

FIG. 30A shows a user's hair prior to treatment; FIG. 30B shows the user's hair immediately after treatment, with three regions indicated: (1) untreated (left ⅓ of the user's hair), (2) treated with the hair styling device of the disclosure (middle ⅓ of the user's hair), and (3) treated with a flat iron (right ⅓ of the user's hair); FIG. 30C shows the user's hair after one wash-and-dry cycle.

Figure 31A:
Figure 31B:
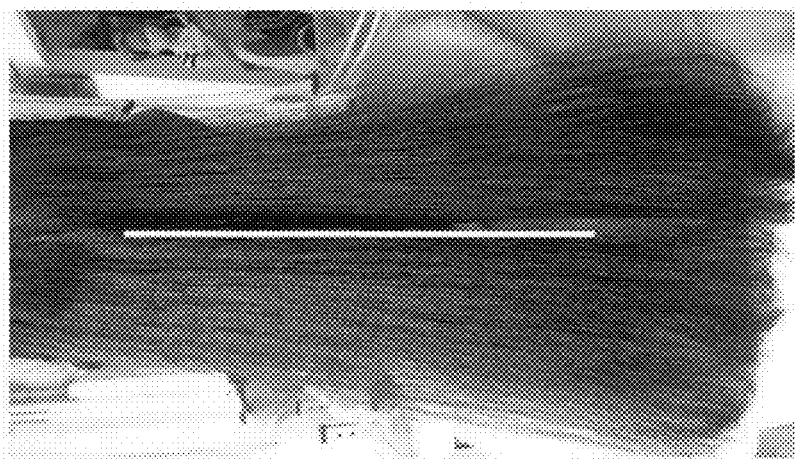
Figure 31C:
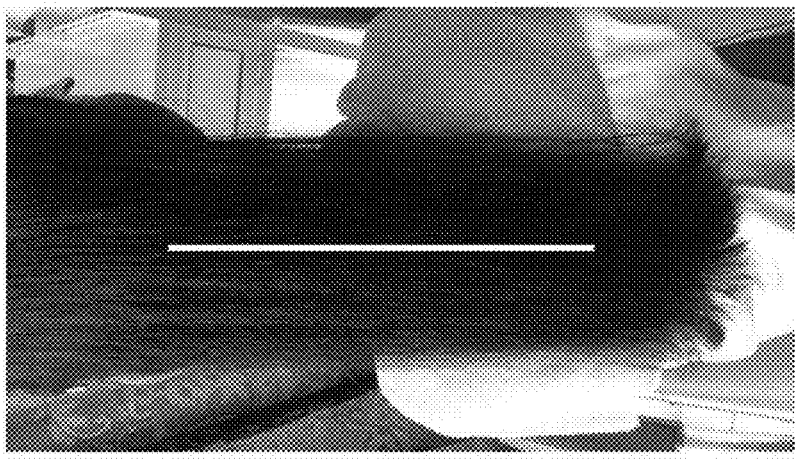

FIG. 31A shows a user's hair prior to treatment; FIG. 31B shows the user's hair immediately after treatment, with two regions indicated: (1) treated with chemical relaxer (left ½ of the user's hair), and (2) treated with the hair styling device of the disclosure (right ½ of the user's hair).

FIG. 32A shows a user's hair prior to treatment; FIG. 32B shows the user's hair immediately after treatment with chemical relaxer (left ½ of the user's hair) and with the hair styling device of the disclosure (right ½ of the user's hair); FIG. 32C shows the user's hair after one month.

FIG. 33A shows a user's hair prior to treatment; FIG. 33B shows the user's hair immediately after treatment with chemical relaxer (left ½ of the user's hair) and with the hair styling device of the disclosure (right ½ of the user's hair), and after one wash-dry cycle; FIG. 33C shows the user's hair after one week.

FIG. 34A shows a user's hair prior to treatment; FIG. 34B shows the user's hair immediately after treatment with chemical relaxer (left ½ of the user's hair) and with the hair styling device of the disclosure (right ½ of the user's hair), and after one wash-dry cycle; FIG. 34C shows the user's hair after one week.

FIG. 35A shows a user's hair prior to treatment; FIG. 35B shows the user's hair immediately after treatment with chemical relaxer (left ½ of the user's hair) and with the hair styling device of the disclosure (right ½ of the user's hair), and after one wash-dry cycle; FIG. 35C shows the user's hair after one week.

FIG. 36A shows a user's hair prior to treatment; FIG. 36B shows the user's hair immediately after treatment with chemical relaxer (left ½ of the user's hair) and with the hair styling device of the disclosure (right ½ of the user's hair), and after one wash-dry cycle; FIG. 36C shows the user's hair after one week.

FIG. 37A shows a user's hair prior to treatment; FIG. 37B shows the user's hair immediately after treatment with chemical relaxer (left ½ of the user's hair) and with the hair styling device of the disclosure (right ½ of the user's hair), and after one wash-dry cycle; FIG. 37C shows the user's hair after one week.

Figures 38A, 38B, 38C:

FIG. 38A shows a user's hair prior to treatment; FIG. 38B shows the user's hair immediately after treatment with chemical relaxer (left ½ of the user's hair) and with the hair styling device of the disclosure (right ½ of the user's hair), and after one wash-dry cycle; FIG. 38C shows the user's hair after one week.

FIG. 39A shows a user's hair prior to treatment; FIG. 39B shows the user's hair immediately after treatment with chemical relaxer (left ½ of the user's hair) and with the hair styling device of the disclosure (right ½ of the user's hair), and after one wash-dry cycle; FIG. 39C shows the user's hair after one week.

FIG. 40A shows a user's hair prior to treatment; FIG. 40B shows the user's hair immediately after treatment with chemical relaxer (left ½ of the user's hair) and with the hair styling device of the disclosure (right ½ of the user's hair), and after one wash-dry cycle; FIG. 40C shows the user's hair after one week.

Exposing Hair to an Alkaline Electrolysis Zone

FIG. 41A shows a scanning electron microscopy (SEM) image of a strand of hair that has not been treated by electrolysis. The cuticles of the hair can be seen closely packed together. The strand of hair was then disposed on a cathode and exposed to the alkaline environment around the cathode (with an applied voltage at the first electrode of −48 V) for about five minutes. The strand of hair was then fixed with paraformaldehyde to fix the cuticles and an SEM image of the electrolysed hair was taken again shown in FIG. 41B. Compared to the untreated hair, the cathode treatment opens up the scales of the cuticle layers on the surface of hair. Furthermore, the strand of hair swelled up indicating that that the dense protein network forming the hair had opened up, which can be attributed to breaking of the disulfide bonds.

FIG. 42 shows a cellulose microparticle that can be included in the electrolyte. A plurality of carboxylic groups are conjugated to the cellulose microparticle. The carboxylic groups can provide a negative charge on the cellulose microparticle. In this manner, the cellulose microparticle can be incorporated in the hair by electrostatic coupling with oppositely charged nanoparticles (e.g., multifunctional polymer molecules) or microparticles that were previously incorporated into the hair using electrolysis. In some embodiments, a plurality of the cellulose microparticles can be incorporated into the hair to increase the thickness of the hair. Furthermore, in some embodiments, the cellulose microparticles coated on the hair can absorb a coloring agent in contact with the hair, for example, a dye, or a pigment thereby coloring the hair.

Incorporating Multifunctional Polymer Molecules in Hair Using Electrolysis

Biotinylated Multifunctional PAA(CAD-PEG-CAG)$_n$ polymer molecules were prepared according to the following protocol. The protocol explains the quantity of different chemicals used in terms of 'X' and 'Y' moles. The value of 'X' and 'Y' can be any number depending on how much of the final product is required for the application. Hence explaining the different amounts of chemicals in different proportion of X and Y allows the freedom to choose any arbitrary amount of starting chemicals and following the proportion of X and Y for the chemicals added or used downstream in the protocol. X moles of polyethylene glycol (PEG) having an average molecular weight 3000 were dissolved in dimethyl sulfoxide (DMSO) and 2× moles of 1,1'-carbonyldiimidazole (CDI) were added to activate all the —OH groups on the PEG. The CDI was activated by shaking the mixture and incubating the mixture for about 3 hours at room temperature. 2× moles of cadaverine (CAD) which is a diamine, were added to the activated PEG to form a conjugate CAD-PEG-CAD which had free amine groups at its ends and a concentration of X moles. The mixture was incubated for 2 hours at room temperature after shaking. Y moles of polyacrylic acid (PAA) of average molecular weight 1800 and having a total of X moles of carboxylic acid groups in Y moles of the PAA were dissolved in DMSO and activated with X moles of CDI. The X moles of CAD-PEG-CAD were added to the activated Y moles of PAA to form the conjugate PAA (CAD-PEG-CAD)$_n$ in DMSO. The mixture was incubated for 12 hours at room temperature after shaking. To couple biotin to the multifunctional polymer molecule, X/2 moles of mercaptoethanol (ME) were dissolved in DMSO and activated by X/2 moles of CDI. X/10 moles of biotin dissolved in DMSO were activated by X/10 moles of CDI. The activated biotin solution was added first to the PAA (CAD-PEG-CAD)$_n$ solution in DMSO. After a gap of 30 minutes, the activated ME was added to the biotin solution. The mixture was incubated for 3 hours at room temperature after shaking. The formed multifunctional polymer molecule that includes multiple free amine groups, sulfhydryl groups, and biotin tags was precipitated from the DMSO by adding equal volume of acetone to the mixture and incubating at minus 20 degrees Celsius for 5 hours. The precipitate was isolated and vacuum dried. The multifunctional polymer molecule had a high solubility of about 30% w/w in water.

A first strand of hair (also referred to as "the test strand") was disposed on an electrode included in an electrolysis unit that included an electrolyte (3M sodium chloride in water) in contact with the electrode. The electrode was biased at a negative voltage (−48 V) against a ground electrode to produce an alkaline electrolysis zone and electrolysis was performed on the test strand for about 2 minutes. The electrode with the test strand disposed thereon was then immersed in a 30% w/w solution of the PAA (CAD-PEG-CAD)$_n$ multifunctional polymer molecule and incubated for about 1 minute. The electrode and the test strand disposed on the electrode were again disposed in the electrolysis unit and brought in contact with the electrolyte. The electrode was biased at a positive voltage to produce an acidic electrolysis zone and electrolysis was performed on the test strand for about 2 minutes. The test strand was removed from the electrode and washed in running water for about 1 minute.

Separately a second strand of hair (also referred to as "the control strand") which had not been subjected to electrolysis was incubated in the multifunctional polymer solution for about 1 minute and then washed in running water for about 1 minute. Both the control strand and the test strand were incubated in a 20 nm gold nanoparticle conjugated streptavidin solution for about 30 minutes at room temperature and then washed in running water for about 1 minute. If the biotinylated multifunctional polymer were incorporated in the hair, the gold nanoparticle conjugated streptavidin would bind with the biotin and also be incorporated in the hair via the biotinylated multifunctional polymer molecules. The gold nanoparticles can be viewed under an SEM to confirm the presence or absence of the multifunctional polymer molecules. FIG. 43A shows an SEM image of the control strand. No gold nanoparticles are present in the hair indicating that the multifunctional polymer molecules are not incorporated into hair by incubating in the polymer solution. FIG. 43B shows an SEM image of the test strand. Gold nanoparticles can be seen disposed on the test strand (white dots within the white circles). This shows that multifunctional polymer molecules, and therefore nanoparticles can be incorporated into hair by electrolysis.

Electrolytic Addition of Microparticles to Hair

Cellulose microparticles were synthesized according to the following protocol. Tissue paper soaked in water for about 3 hours was blended for about 5 minutes in a blender to from cellulose microparticles. The suspension of cellulose microparticles was transferred to a bottom sealed vertical tube and allowed to stand still for about 5 minutes. This allowed the larger cellulose particles to settle down at the base of the tube such that only fine microparticles of the cellulose remain suspended in the supernatant. An upper portion of the supernatant which included the fine cellulose microparticles was separated and the microparticles were separated from the solution by centrifugation. The microparticles were removed and vacuum dried.

The protocol explains the quantity of different chemicals used in terms of 'X' and 'Y' moles or milligrams. The value of 'X' and 'Y' can be any number depending on how much of the final product is required for the application. Hence explaining the different amounts of chemicals in different proportion of X and Y allows the freedom to choose any arbitrary amount of starting chemicals and following the proportion of X and Y for the chemicals added or used downstream in the protocol. X milligrams of the cellulose microparticles that include about Y moles of total hydroxyl group content were resuspended in DMSO to which Y/50 moles of CDI was added to activate the hydroxyl groups on the cellulose microparticles. Activation was performed by incubating the cellulose microparticle solution including the CDI for about 3 hours at 37 degrees Celsius under constant shaking. The activated cellulose microparticles in DMSO were then incubated with Y/50 moles of cadaverine for about 3 hours at 37 degrees Celsius under constant shaking.

Separately, Y/25 moles of citric acid in DMSO was activated by adding 3Y/25 moles of CDI to the citric acid solution and incubating at room temperature for about 2 hours after shaking the mixture. The activated citric acid solution was added to the cadaverine conjugated cellulose microparticle solution and incubated for about 3 hours at 37 degrees Celsius under constant shaking. This couples the citric acid to the cellulose microparticles through diamine bridges. The citric acid moieties on the cellulose microparticles provide multiple free carboxylic acid groups on the surface of the cellulose microparticles which generates a negative charge on the microparticles in water. The cellulose microparticles suspended in the DMSO were isolated by centrifugation. The precipitate was washed twice in acetone and then vacuum dried.

A third strand of hair (also referred to as "the third strand") and a fourth strand of hair (also referred to as "the fourth strand") were electrolytically coated with positively charged PAA (CAD-PEG-CAD)$_n$ using substantially the same process described above with reference to FIGS. 43A and 43B, but with an electrode bias of −45 V. Each of the third strand and the fourth strand had a natural white color. The third strand and the fourth strand were immersed in the cellulose microparticle solution and incubated for a predetermined period of time. The negatively charged cellulose microparticles are attracted to the positively charged multifunctional polymer molecules and are electrostatically coupled to the multifunctional polymer molecules such that the cellulose microparticles are disposed on the hair. FIG. 44 shows a light microscopy image of the third strand with a plurality of cellulose microparticles disposed thereon and adding substantially to the thickness of the hair. The fourth strand was further immersed in a green dye after coating with the cellulose microparticles. The cellulose microparticles absorb the green dye and thereby impart color to the hair. FIG. 45 shows a light microscopy image of the cellulose microparticles disposed on the fourth strand and colored with the green dye (the coloration being represented by cross-hatching). In this way, cellulose or any other microparticles can be coated on the hair using electrolytically incorporated multifunctional nanoparticles (e.g., multifunctional polymer molecules) and be used to impart thickening and/or color to the hair.

Electrolytic Addition of Colors to Hair

A fifth strand of hair (also referred to as "the fifth strand") which was naturally white in color, was disposed on an electrode included in an electrolysis cell and in contact with an electrolyte. The electrode was biased at a negative voltage to produce an alkaline electrolysis zone in the electrolyte. The fifth strand was exposed to the electrolysis zone for about 2 minutes. The fifth strand was removed from the electrolytic cell and the disposed in a nigrosin solution having a neutral pH for about 30 seconds. The fifth strand was removed from the nigrosin solution and was again disposed on the electrode in the electrolytic cell. The electrode was biased at a positive voltage to produce an acidic alkaline zone. The hair was exposed to the acidic alkaline zone for about 2 minutes. The hair was remove from the electrolysis cell and rinsed in running water for about 1 minute.

Separately a sixth strand of hair (also referred to as "the sixth strand") having a naturally white color was immersed in the nigrosin solution for about 2 minutes and then rinsed with running water. FIG. 46A shows a light microscopy image of the sixth strand (i.e., the control strand). The sixth strand appears white under the microscope indicating that negligible amount of nigrosin is incorporated or otherwise coated on the hair by immersing the control strand in nigrosin. In contrast, FIG. 46B shows a light microscope image of the fifth strand of hair. The fifth strand was heavily stained by the pigment clearly indicating that hair can be efficiently colored using electrolysis.

While various embodiments of the system, methods and devices have been described above, it should be understood that they have been presented by way of example only, and not limitation. Where methods and steps described above indicate certain events occurring in a certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

The invention claimed is:

1. A method for styling hair, comprising:
arranging a section of hair between a first electrode and a second electrode;
contacting the section of hair with an electrolyte;
causing the first electrode to have a first negative potential; and
causing the second electrode to have a second negative potential, the absolute value of the first negative potential being greater than the absolute value of the second negative potential, the difference in electrical potential between the first electrode and the second electrode creating an electrolysis zone between the first electrode and the second electrode,
wherein the absolute value of the second negative potential is less than half the absolute value of the first negative potential.

2. The method of claim 1, wherein the difference in electrical potential between the first electrode and the second electrode is at least about 5 volts.

3. The method of claim 2, wherein the difference in electrical potential between the first electrode and the second electrode is at least about 10 volts.

4. The method of claim 1, wherein the first negative potential is in the range of about −6 volts to about −50 volts.

5. The method of claim 4, wherein the difference in electrical potential between the first electrode and the second electrode is in the range of about 5 volts to about 20 volts.

6. The method of claim 1, further comprising:
producing a pH of at least about 10 in the electrolyte contacting the section of hair.

7. A method for styling hair, the method comprising:
arranging a section of hair between a first electrode and a second electrode;
contacting the section of hair with an electrolyte;
causing the first electrode to have a first negative potential; and
causing the second electrode to have a second negative potential, the absolute value of the first negative potential being greater than the absolute value of the second negative potential, the difference in electrical potential between the first electrode and the second electrode creating an electrolysis zone between the first electrode and the second electrode,
wherein the absolute value of the second negative potential is less than 1 volt.

8. A method of styling hair using a hair styling device, the hair styling device including a first electrode electrically coupled to a DC power module and a second electrode electrically coupled to the DC power module, and a second electrode, the method comprising:
disposing hair between the first electrode and the second electrode;
disposing an electrolyte on the hair;
causing the first electrode to have a first negative potential and the second electrode to have a second negative potential, the absolute value of the first negative potential being different than the absolute value of the second negative potential; and
producing a current between the first electrode and the second electrode of at least about 1.5 amperes,
wherein the absolute value of the second negative potential is less than half the absolute value of the first negative potential.

9. The method of claim 8, wherein the current between the first electrode and the second electrode is in the range of about 2 amperes to about 12 amperes.

10. The method of claim 8, wherein the electrolyte includes a salt at a concentration from about 1M to about 5M.

11. The method of claim 8, wherein the electrolyte includes a solvent, a salt, and at least one of: a chlorine formation inhibitor, an electrolysis foam booster, a wetting agent, a humectant, a hydrophobic agent, and a surfactant.

12. The method of claim 8, wherein the electrolyte includes at least one of: water, ascorbic acid, a humectant, sodium iodide (NaI), cocamidopropyl betaine, glycerol, coconut oil, mineral oil, silicone oil, petroleum jelly and/or PEG 40-hydrogenated castor oil.

13. The method of claim 8, wherein the electrolyte includes conductive particles.

14. The method of claim 8, wherein the method produces a change in style to the hair that is disposed between the first electrode and the second electrode.

15. The method of claim 14, wherein the change in style comprises at least one of straightening, coloring, moisturizing and thickening.

16. The method of claim 1, wherein the electrolyte includes a salt at a concentration from about 1M to about 5M.

17. The method of claim 1, wherein the electrolyte includes a solvent, a salt, and at least one of: a chlorine formation inhibitor, an electrolysis foam booster, a wetting agent, a humectant, a hydrophobic agent, and a surfactant.

18. The method of claim 1, wherein the electrolyte includes at least one of: water, ascorbic acid, a humectant, sodium iodide (NaI), cocamidopropyl betaine, glycerol, coconut oil, mineral oil, silicone oil, petroleum jelly and/or PEG 40-hydrogenated castor oil.

19. The method of claim 1, wherein the electrolyte includes conductive particles.

20. The method of claim 1, wherein at least one of the first electrode or the second electrode is in contact with an electrolyte reservoir for containing a volume of the electrolyte.

21. The method of claim 20, wherein the electrolyte reservoir comprises at least one of an absorbent pad, a sponge, or a porous material.

22. The method of claim 7, wherein the difference in electrical potential between the first electrode and the second electrode is at least about 5 volts.

23. The method of claim 22, wherein the difference in electrical potential between the first electrode and the second electrode is at least about 10 volts.

24. The method of claim 7, wherein the first negative potential is in the range of about −6 volts to about −50 volts.

25. The method of claim 24, wherein the difference in electrical potential between the first electrode and the second electrode is in the range of about 5 volts to about 20 volts.

26. The method of claim 7, further comprising:
producing a pH of at least about 10 in the electrolyte contacting the section of hair.

27. The method of claim 7, wherein the absolute value of the second negative potential is less than half the absolute value of the first negative potential.

* * * * *